United States Patent
Eis et al.

(10) Patent No.: US 8,003,787 B2
(45) Date of Patent: Aug. 23, 2011

(54) SULPHOXIMINE-SUBSTITUTED QUINOLINE AND QUINAZOLINE DERIVATIVES AS KINASE INHIBITORS

(75) Inventors: Knut Eis, Berlin (DE); Olaf Prien, Berlin (DE); Ulrich Lücking, Berlin (DE); Judith Günther, Berlin (DE); Dieter Zopf, Berlin (DE); Dirk Brohm, Mettmann (DE); Verena Vöhringer, Wuppertal (DE); Elisabeth Woltering, Hilden (DE); Hartmut Beck, Köln (DE); Mario Lobell, Wuppertal (DE); Volkhart Min-Jian Li, Velbert (DE); Susanne Greschat, Düsseldorf (DE)

(73) Assignee: Bayer Schering Pharma AG, Berlin (DE)

( * ) Notice: Subject to any disclaimer, the term of this patent is extended or adjusted under 35 U.S.C. 154(b) by 0 days.

(21) Appl. No.: 12/126,437

(22) Filed: May 23, 2008

(65) Prior Publication Data

US 2009/0226377 A1 Sep. 10, 2009

Related U.S. Application Data

(60) Provisional application No. 60/940,233, filed on May 25, 2007, provisional application No. 61/020,908, filed on Jan. 14, 2008.

(30) Foreign Application Priority Data

May 24, 2007 (DE) .......................... 10 2007 024 470
Dec. 20, 2007 (EP) ..................................... 07076116

(51) Int. Cl.
C07D 239/86 (2006.01)
(52) U.S. Cl. ........................................ 544/287; 544/293
(58) Field of Classification Search .................. 544/287, 544/293
See application file for complete search history.

(56) References Cited

U.S. PATENT DOCUMENTS

| 5,457,105 A | 10/1995 | Barker |
| 5,747,498 A | 5/1998 | Schnur |
| 7,825,128 B2 | 11/2010 | Lucking |

FOREIGN PATENT DOCUMENTS

| CA | 2592009 A1 | 6/2006 |
| DE | 10 2005 062 742 A1 | 6/2007 |
| WO | 9730034 A | 8/1997 |
| WO | 2006066955 A | 6/2006 |
| WO | PCTEP2008004378 R | 8/2008 |

OTHER PUBLICATIONS

West, Anthony R., Solid State Chemistry and its Applications, Wiley, New York, 1988, pp. 358 and 365.*
International Preliminary Report on Patentability of International Application PCT/EP2008/004378, filed May 23, 2008.

* cited by examiner

*Primary Examiner* — James O Wilson
*Assistant Examiner* — Brian McDowell
(74) *Attorney, Agent, or Firm* — Millen, White, Zelano & Branigan, P.C.

(57) ABSTRACT

The present invention relates to a quinoline or quinazoline derivative having the general formula (A):

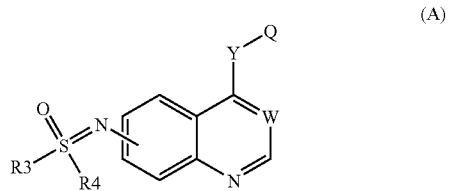

(A)

in which $R^3$, $R^4$, W, Y and Q are indicated in the description and the claims, the use of the compounds of the general formula (A) for the treatment of various disorders, and the preparation of compounds of the general formula (A).

21 Claims, No Drawings

SULPHOXIMINE-SUBSTITUTED QUINOLINE AND QUINAZOLINE DERIVATIVES AS KINASE INHIBITORS

This application claims the benefit of the filing date of U.S. Provisional Application Ser. No. 60/940,233 filed May 25, 2007, and U.S. Provisional Application Ser. No. 61/020,908 filed Jan. 14, 2008.

The invention relates to certain quinoline and quinazoline derivatives, their preparation and use as inhibitor of protein kinases, in particular of Eph (erythropoetin-producing hepatoma amplified sequence) receptors for the treatment of various disorders.

Protein tyrosine kinases catalyze the phosphorylation of specific tyrosine residues in various proteins. Such phosphorylation reactions play a part in a large number of cellular processes which are involved in the regulation of growth and differentiation of cells. Protein tyrosine kinases are divided into receptor and non-receptor tyrosine kinases. The family of receptor tyrosine kinases (RTKs) consists of 58 kinases (Manning G. et al. 2002, *Science* 298, 1912-1934). RTKs have an extracellular ligand binding domain, a transmembrane domain and an intracellular domain which usually comprises the tyrosine kinase activity. RTKs mediate signal transduction from extracellular stimulators such as, for example, growth factors. The ligand binding leads to dimerization of the RTKs and reciprocal autophosphorylation of their intracellular domains. Depending on the cell type, specific intracellular binding proteins are recruited thereby (inter alia non-receptor tyrosine kinases), via which signal processing takes place in the cell (Schlessinger J. 2000, *Cell* 103, 211-225). These include receptor families of growth factors such as EGF (epidermal growth factor), VEGF (vascular endothelial growth factor), FGF (fibroblast growth factor), PDGF (platelet derived growth factor) and NGF (nerve growth factor), and of the insulin receptors, and the large family of ephrin receptors and others.

The ephrin (Eph) receptors constitute the largest family within the RTKs. They are divided according to their sequential relationship and their ligand specificity into the group of EphA receptors (9 members) and of EphB receptors (6 members) (Kullander K. and Klein R. 2002, *Nat. Rev. Mol. Cell Biol.* 3, 475-486; Cheng N. et al. 2002, Cyt. and growth factor Rev. 13, 75-85.). Eph receptors are activated by membrane-associated ligands of the EphrinA or EphrinB family. EphrinAs are anchored in the cell membrane via glycolipids (GPI), whereas EphrinBs have a transmembrane region and an intracellular domain. The interaction between Ephrins and the Eph receptors leads to a bidirectional signal transmission in the ephrin-expressing and in the Eph-receptor-carrying cells. Ephrins and Eph receptors play a part in a large number of morphogenetic processes in embryonic development and in the adult organism. They are involved in embryo patterning, in the development of the blood vessel system (Gerety S. S: et al 1999, *Mol. Cell.* 4, 403-414) and in the establishment of neuronal interconnections (Flanagan, J. G. and Vanderhaeghen, P., 1998, *Annu. Rev. Neurosci.* 21, 306-354). In the adult organism, they are involved in neovascularization processes, e.g. in tumour development and in endometriosis, and in the morphogenesis of the intestinal epithelium (Battle E. et al. 2002, *Cell* 111:251-63.). At the cellular level, they mediate migration, adhesion and juxtacrine cell contacts. Elevated expression of Eph receptors such as, for example, EphB2 and EphB4 has also been observed in various tumour tissues such as, for example, breast and bowel tumours (Nakamoto M. and Bergemann A. D. 2002, *Mic. Res. Tech.* 59, 58-67). EphB2, EphB3 and EphB4 knockout mice show defects in the formation of the blood vessel system. The embryonic lethality of EphB4 −/− mice in embryonic stage d14 shows the special role of EphB4 in this process (Gerety S. S: et al 1999, *Mol. Cell.* 4, 403-414). Modulation of these receptors, e.g. by inhibiting their kinase activity, leads for example to suppression of tumour growth and/or tumour metastasis either through a direct antitumour or through an indirect antiangiogenic effect.

Non-receptor tyrosine kinases occur in soluble form inside cells and are involved in the processing of extracellular signals (e.g. from growth factors, cytokines, antibodies, adhesion molecules) inside the cell. They include inter alia the families of src(sarcoma) kinases, of Tec(tyrosine kinase expressed in hepatocellular carcinoma) kinases, of Abl(Abelson) kinases and of Brk(breast tumor kinase) kinases, and the focal adhesion kinase (FAK).

An altered activity of these protein tyrosine kinases may lead to a wide variety of physiological disorders in the human body and thus cause for example inflammatory, neurological and oncological disorders.

WO 01/19828 A discloses a wide variety of kinase inhibitors.

US 2004116388 A discloses triazine compounds which inhibit receptor tyrosine kinases.

WO 03/089434 A discloses imidazo[1,2a]pyrazin-8-ylamines, and WO 04/00820 A discloses various aromatic monocycles, which inhibit receptor tyrosine kinases.

EP 0 187 705 A2 describes imidazo[4,5f]quinolines which exhibit an immunomodulating effect in infectious diseases. Likewise, U.S. Pat. No. 5,506,235 A describes imidazo[4,5f]quinolines with an immunostimulating effect.

WO 04/006846 A discloses various quinazoline derivatives which inhibit receptor tyrosine kinases.

WO 03/053960 describes substituted 3-cyanoquinoline derivatives as MEK inhibitors.

US2005/0026933 claims quinolinecarbonitriles as ERFG inhibitors.

WO 01/68186 describes cyanoquinolines for the treatment of bowel polyps.

However, no Eph receptor inhibitors are described among the receptor tyrosine kinase inhibitors.

It is an object of the present invention to provide compounds which inhibit receptor tyrosine kinases, especially Eph receptors.

The object is achieved by quinoline or quinazoline derivatives having the general formula (A), a process for preparing the quinoline or quinazoline derivative, the uses of the quinoline or quinazoline derivative, and a medicament comprising the quinoline or quinazoline derivative, according to the following description and the claims.

The present invention relates to a quinoline or quinazoline derivative having the general formula (A):

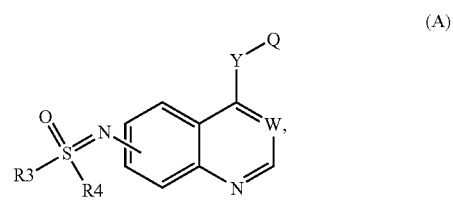

where
w is CH or N;
Y-Q is $NR^1R^2$ or $OR^1$;

$R^1$ and $R^2$ are identical or different and are selected one or more times independently of one another from the group comprising hydrogen, —$C_1$-$C_6$-alkyl, —$C_1$-$C_4$-hydroxyalkyl, —$C_2$-$C_6$-alkenyl, —$C_2$-$C_6$-alkynyl, —$C_3$-$C_{10}$-cycloalkyl, —$C_3$-$C_{12}$-heterocycloalkyl, —$C_6$-$C_{12}$-aryl, —$C_5$-$C_{18}$-heteroaryl, —$C_1$-$C_6$-alkoxy, —$C_1$-$C_6$-alkoxy-$C_1$-$C_6$-alkoxy, —$C_1$-$C_6$-alkoxy-$C_1$-$C_6$-alkyl, —$C_1$-$C_6$-alkoxy-$C_1$-$C_6$-alkoxy-$C_1$-$C_6$-alkyl, —$(CH_2)_n$—$C_6$-$C_{12}$-aryl, —$(CH_2)_n$—$C_5$-$C_{18}$-heteroaryl, —$(CH_2)_n$—$C_3$-$C_{10}$-cycloalkyl, —$(CH_2)_n$—$C_3$-$C_{12}$-heterocycloalkyl, -phenylene-$(CH_2)_p$—$R^6$, —$(CH_2)_p PO_3(R^6)_2$, —$(CH_2)_p$—$NR^5R^6$, —$(CH_2)_p$—$NR^4COR^5$, —$(CH_2)_p$—$NR^4CSR^5$, —$(CH_2)_p$—$NR^4S(O)R^5$, —$(CH_2)_p$—$NR^4S(O)_2R^5$, —$(CH_2)_p$—$NR^4CONR^5R^6$, —$(CH_2)_p$—$NR^4COOR^5$, —$(CH_2)_p$—$NR^4C(NH)NR^5R^6$, —$(CH_2)_p$—$NR^4CSNR^5R^6$, —$(CH_2)_p$—$NR^4S(O)NR^5R^6$, —$(CH_2)_p$—$NR^4S(O)_2NR^5R^6$, —$(CH_2)_p$—$COR^5$, —$(CH_2)_p$—$CSR^5$, —$(CH_2)_p$—$S(O)R^5$, —$(CH_2)_p$—$S(O)(NH)R^5$, —$(CH_2)_p$—$S(O)_2R^5$, —$(CH_2)_p$—$S(O)_2NR^5R^6$, —$(CH_2)_p$—$SO_2OR^5$, —$(CH_2)_p$—$CO_2R^5$, —$(CH_2)_p$—$CONR^5R^6$, —$(CH_2)_p$—$CSNR^5R^6$, —$OR^5$, —$CHR^5R^6$, —$(CH_2)_p$—$SR^5$ and —$CR^5(OH)$—$R^6$, where —$C_1$-$C_6$-alkyl, —$C_2$-$C_6$-alkenyl, —$C_2$-$C_6$-alkynyl, —$C_3$-$C_{10}$-cycloalkyl, —$C_3$-$C_{12}$-heterocycloalkyl, —$C_6$-$C_{12}$-aryl, —$C_5$-$C_{18}$-heteroaryl or —$C_1$-$C_6$-alkoxy are unsubstituted or are substituted one or more times independently of one another by hydroxy, halogen, nitro, cyano, —$C_1$-$C_6$-alkyl, —$C_1$-$C_6$-haloalkyl, —$NR^5R^6$, —$C(O)NR^5R^6$, —$S(O)_2NR^5R^6$, —$NR^5S(O)_2R^6$, —$NR^5C(O)R^6$, —$SR^5$, —$R^5$, or —$OR^5$, where the carbon framework of the —$C_3$-$C_{10}$-cycloalkyl and of the —$C_1$-$C_{10}$-alkyl may comprise one or more times independently of one another nitrogen, oxygen, sulphur atoms, —$NR^4$ or C=O groups or one or more double bonds, or $R^1$ and $R^2$ optionally form together a bridge of 3-10 methylene units, where up to two methylene units are optionally replaced by O, S or —$NR^4$, and where the phenyl radical is optionally substituted one or more times independently of one another by hydroxy, halogen, nitro, cyano, phenyl, —$NR^5R^6$, alkyl or —$OR^5$;

$R^3$ and $R^4$ are selected independently of one another from the group comprising hydrogen, —$C_1$-$C_{10}$-alkyl, —$C_2$-$C_6$-alkenyl, —$C_2$-$C_6$-alkynyl, —$C_3$-$C_{10}$-cycloalkyl, —$C_3$-$C_{12}$-heterocycloalkyl, —$C_6$-$C_{12}$-aryl or —$C_1$-$C_{10}$-alkanoyl, where —$C_1$-$C_{10}$-alkyl, —$C_2$-$C_6$-alkenyl, —$C_2$-$C_6$-alkynyl, —$C_3$-$C_{10}$-cycloalkyl, —$C_3$-$C_{12}$-heterocycloalkyl, —$C_6$-$C_{12}$-aryl or —$C_1$-$C_{10}$-alkanoyl is unsubstituted or is substituted one or more times independently of one another by hydroxy, halogen, nitro, cyano, phenyl, —$NR^5R^6$, —$C_1$-$C_{10}$-alkyl, —$SR^5$ or —$OR^5$, or $R^3$ and $R^4$ may, via the respective sulphur atom to which they are attached, form a ring, the size of the ring being 5, 6, 7, 8, 9 or 10 ring atoms, optionally consisting of carbon, nitrogen, oxygen or sulphur atoms;

$R^5$ and $R^6$ are identical or different and are selected independently of one another from the group comprising hydrogen, —$C_1$-$C_{10}$-alkyl, —$C_2$-$C_{10}$-alkenyl, —$C_2$-$C_{10}$-alkynyl, —$C_1$-$C_6$-alkoxy, —C(=O)—$C_1$-$C_6$-alkyl, —$C_3$-$C_{10}$-cycloalkyl, —$C_3$-$C_{12}$-heterocycloalkyl, —$C_6$-$C_{12}$-aryl and —$C_5$-$C_{18}$-heteroaryl, where —$C_1$-$C_{10}$-alkyl, —$C_2$-$C_{10}$-alkenyl, —$C_2$-$C_{10}$-alkynyl, —$C_1$-$C_6$-alkoxy, —$C_3$-$C_{10}$-cycloalkyl, —$C_3$-$C_{12}$-heterocycloalkyl, —$C_6$-$C_{12}$-aryl or —$C_5$-$C_{18}$-heteroaryl are unsubstituted or are substituted one or more times independently of one another by hydroxy, halogen, cyano, nitro, —$OR^7$, —$NR^7R^8$, —$C(O)NR^7R^8$, —$C(O)OR^7$ or —$C_1$-$C_6$-alkyl, where —$C_1$-$C_6$-alkyl is unsubstituted or is substituted one or more times independently of one another by halogen, hydroxy, cyano, —$NR^7R^8$, —$OR^7$ or phenyl; or $R^5$ and $R^6$ optionally together form a bridge of 3-10 methylene units, where up to two methylene units are optionally replaced by O, S or $NR^4$;

$R^7$, $R^8$ are identical or different and are selected independently of one another from the group comprising hydrogen, —$C_1$-$C_4$-alkyl, —$C_6$-$C_{12}$-aryl and —$C_5$-$C_{18}$-heteroaryl, where alkyl, aryl, heteroaryl is unsubstituted or is substituted one or more times independently of one another by halogen or alkoxy, or $R^7$ and $R^8$ optionally together form a bridge of 3-10 methylene units, where up to two methylene units are optionally replaced by O, S or —$NR^4$;

n=1, 2, 3, 4, 5, or 6, p=0, 1, 2, 3, 4, 5, or 6, and the N-oxides, solvates, hydrates, stereoisomers, diastereomers, enantiomers and salts thereof.

It is to be understood that the R3(R3)S(=O)=N— group according to the invention may be bonded to any available carbon atom in the quin(az)oline ring, in particular the carbon atoms in position 2, 5, 6, 7 or 8 of said quin(az)oline ring.

A preferred subgroup are compounds in which:

W is CH or N;

Y-Q is $NR^1R^2$;

$R^1$ and $R^2$ are identical or different and are selected one or more times independently of one another from the group comprising hydrogen, —$C_1$-$C_6$-alkyl, —$C_1$-$C_4$-hydroxyalkyl, —$C_2$-$C_6$-alkenyl, —$C_2$-$C_6$-alkynyl, —$C_3$-$C_{10}$-cycloalkyl, —$C_3$-$C_{12}$-heterocycloalkyl, —$C_6$-$C_{12}$-aryl, —$C_5$-$C_{18}$-heteroaryl, —$C_1$-$C_6$-alkoxy, —$C_1$-$C_6$-alkoxy-$C_1$-$C_6$-alkoxy, —$C_1$-$C_6$-alkoxy-$C_1$-$C_6$-alkyl, —$C_1$-$C_6$-alkoxy-$C_1$-$C_6$-alkoxy-$C_1$-$C_6$-alkyl, —$(CH_2)_n$—$C_6$-$C_{12}$-aryl, —$(CH_2)_n$—$C_5$-$C_{18}$-heteroaryl, —$(CH_2)_n$—$C_3$-$C_{10}$-cycloalkyl, —$(CH_2)_n$—$C_3$-$C_{12}$-heterocycloalkyl, -phenylene-$(CH_2)_p$—$R^6$, —$(CH_2)_p$—$NR^5R^6$, —$(CH_2)_p$—$NR^4COR^5$, —$(CH_2)_n$—$NR^4CSR^5$, —$(CH_2)_p$—$NR^4S(O)R^5$, —$(CH_2)_p$—$NR^4S(O)_2R^5$, —$(CH_2)_p$—$NR^4CONR^5R^6$, —$(CH_2)_p$—$NR^4COOR^5$, —$(CH_2)_p$—$NR^4C(NH)NR^5R^6$, —$(CH_2)_p$—$NR^4CSNR^5R^6$, —$(CH_2)_p$—$NR^4S(O)NR^5R^6$, —$(CH_2)_p$—$NR^4S(O)_2NR^5R^6$, —$(CH_2)_p$—$COR^5$, —$(CH_2)_p$—$CSR^5$, —$(CH_2)_p$—$S(O)R^5$, —$(CH_2)_p$—$S(O)(NH)R^5$, —$(CH_2)_p$—$S(O)_2R^5$, —$(CH_2)_p$—$S(O)_2NR^5R^6$, —$(CH_2)_n$—$SO_2OR^5$, —$(CH_2)_p$—$CO_2R^5$, —$(CH_2)_p$—$CONR^5R^6$, —$(CH_2)_p$—$CSNR^5R^6$, —$OR^5$, —$CHR^5R^6$, —$(CH_2)_p$—$SR^5$ and —$CR^5(OH)$—$R^6$, where —$C_1$-$C_6$-alkyl, —$C_2$-$C_6$-alkenyl, —$C_2$-$C_6$-alkynyl, —$C_3$-$C_{10}$-cycloalkyl, —$C_3$-$C_{12}$-heterocycloalkyl, —$C_6$-$C_{12}$-aryl, —$C_5$-$C_{18}$-heteroaryl or —$C_1$-$C_6$-alkoxy are unsubstituted or are substituted one or more times independently of one another by hydroxy, halogen, nitro, cyano, —$C_1$-$C_6$-alkyl, —$C_1$-$C_6$-haloalkyl, —$NR^5R^6$, —$C(O)NR^5R^6$, —$S(O)_2NR^5R^6$, —$NR^5S(O)_2R^6$, —$NR^5C(O)R^6$, —$SR^5$, —$R^5$ or —$OR^5$ where the carbon framework of the —$C_3$-$C_{10}$-cycloalkyl and of the —$C_1$-$C_{10}$-alkyl may comprise one or more times independently of one another nitrogen, oxygen, sulphur atoms, —$NR^4$ or C=O groups or one or more double bonds, or $R^1$ and $R^2$ optionally together form a bridge of 3-10 methylene units, where up to two methylene units are optionally replaced by O, S or —$NR^4$, and where the phenyl radical is optionally substituted one or more times independently of one another by hydroxy, halogen, nitro, cyano, phenyl, —$NR^5R^6$, alkyl or —$OR^5$;

$R^3$ and $R^4$ are selected independently of one another from the group comprising hydrogen, —$C_1$-$C_{10}$-alkyl, —$C_2$-$C_6$-alkenyl, —$C_2$-$C_6$-alkynyl, —$C_3$-$C_{10}$-cycloalkyl, —$C_3$-$C_{12}$-heterocycloalkyl, —$C_6$-$C_{12}$-aryl or —$C_1$-$C_{10}$-alkanoyl, where —$C_1$-$C_{10}$-alkyl, —$C_2$-$C_6$-alkenyl, —$C_2$-

$C_6$-alkynyl, —$C_3$-$C_{10}$-cycloalkyl, —$C_3$-$C_{12}$-heterocycloalkyl, —$C_6$-$C_{12}$-aryl or —$C_1$-$C_{10}$-alkanoyl is unsubstituted or is substituted one or more times independently of one another by hydroxy, halogen, nitro, cyano, phenyl, —$NR^5R^6$, —$C_1$-$C_{10}$-alkyl, —$SR^5$ or —$OR^5$, or $R^3$ and $R^4$ may, via the respective sulphur atom to which they are attached, form a ring, the size of the ring being 5, 6, 7, 8, 9 or 10 ring atoms, optionally consisting of carbon, nitrogen, oxygen or sulphur atoms;

$R^5$ and $R^6$ are identical or different and are selected independently of one another from the group comprising hydrogen, —$C_1$-$C_{10}$-alkyl, —$C_2$-$C_{10}$-alkenyl, —$C_2$-$C_{10}$-alkynyl, —$C_1$-$C_6$-alkoxy, —$C(=O)$—$C_1$-$C_6$-alkyl, —$C_3$-$C_{10}$-cycloalkyl, —$C_3$-$C_{12}$-heterocycloalkyl, —$C_6$-$C_{12}$-aryl and —$C_5$-$C_{18}$-heteroaryl, where —$C_1$-$C_{10}$-alkyl, —$C_2$-$C_{10}$-alkenyl, —$C_2$-$C_{10}$-alkynyl, —$C_1$-$C_6$-alkoxy, —$C_3$-$C_{10}$-cycloalkyl, —$C_3$-$C_{12}$-heterocycloalkyl, —$C_6$-$C_{12}$-aryl or —$C_5$-$C_{18}$-heteroaryl are unsubstituted or are substituted one or more times independently of one another by hydroxy, halogen, cyano, nitro, —$OR^7$, —$NR^7R^8$, —$C(O)NR^7R^8$, —$C(O)OR^7$ or —$C_1$-$C_6$-alkyl, where —$C_1$-$C_6$-alkyl is unsubstituted or is substituted one or more times independently of one another by halogen, hydroxy, cyano, —$NR^7R^8$, —$OR^7$ or phenyl; or $R^5$ and $R^6$ optionally together form a bridge of 3-10 methylene units, where up to two methylene units are optionally replaced by O, S or $NR^4$;

$R^7$, $R^8$ are identical or different and are selected independently of one another from the group comprising hydrogen, —$C_1$-$C_4$-alkyl, —$C_6$-$C_{12}$-aryl and —$C_5$-$C_{18}$-heteroaryl, where alkyl, aryl, heteroaryl is unsubstituted or is substituted one or more times independently of one another by halogen or alkoxy, or $R^7$ and $R^8$ optionally together form a bridge of 3-10 methylene units, where up to two methylene units are optionally replaced by O, S or —$NR^4$;

n=1, 2, 3, 4, 5, or 6, p=0, 1, 2, 3, 4, 5, or 6, and the N-oxides, solvates, hydrates, stereoisomers, diastereomers, enantiomers and salts thereof.

A particularly preferred subgroup are compounds in which:

W is CH or N;

Y-Q is $NR^1R^2$;

$R^1$ is selected from the group comprising hydrogen, —$C_1$-$C_6$-alkyl, —$C_1$-$C_4$-hydroxyalkyl, —$C_2$-$C_6$-alkenyl, —$C_2$-$C_6$-alkynyl, —$C_3$-$C_{10}$-cycloalkyl, —$C_3$-$C_{12}$-heterocycloalkyl, —$C_6$-$C_{12}$-aryl, —$C_5$-$C_{18}$-heteroaryl, —$C_1$-$C_6$-alkoxy, —$C_1$-$C_6$-alkoxy-$C_1$-$C_6$-alkoxy, —$C_1$-$C_6$-alkoxy-$C_1$-$C_6$-alkyl, —$C_1$-$C_6$-alkoxy-$C_1$-$C_6$-alkoxy-$C_1$-$C_6$-alkyl, —$(CH_2)_n$—$C_6$-$C_{12}$-aryl, —$(CH_2)_n$—$C_5$-$C_{18}$-heteroaryl, —$(CH_2)_n$—$C_3$-$C_{10}$-cycloalkyl, —$(CH_2)_n$—$C_3$-$C_{12}$-heterocycloalkyl, -phenylene-$(CH_2)_p$—$R^6$, —$(CH_2)_p$—$NR^5R^6$, —$(CH_2)_p$—$NR^4COR^5$, —$(CH_2)_p$—$NR^4CSR^5$, —$(CH_2)_p$—$NR^4S(O)R^5$, —$(CH_2)_p$—$NR^4S(O)_2R^5$, —$(CH_2)_p$—$NR^4CONR^5R^6$, —$(CH_2)_p$—$NR^4COOR^5$, —$(CH_2)_p$—$NR^4C(NH)NR^5R^6$, —$(CH_2)_p$—$NR^4CSNR^5R^6$, —$(CH_2)_p$—$NR^4S(O)NR^5R^6$, —$(CH_2)_p$—$NR^4S(O)_2NR^5R^6$, —$(CH_2)_p$—$COR^5$, —$(CH_2)_p$—$CSR^5$, —$(CH_2)_p$—$S(O)R^5$, —$(CH_2)_p$—$S(O)(NH)R^5$, —$(CH_2)_p$—$S(O)_2R^5$, —$(CH_2)_p$—$S(O)_2NR^5R^6$, —$(CH_2)_p$—$SO_2OR^5$, —$(CH_2)_p$—$CO_2R^5$, —$(CH_2)_p$—$CONR^5R^6$, —$(CH_2)_p$—$CSNR^5R^6$, —$OR^5$, —$CHR^5R^6$, —$(CH_2)_p$—$SR^5$ and —$CR^5(OH)$—$R^6$, where —$C_1$-$C_6$-alkyl, —$C_2$-$C_6$-alkenyl, —$C_2$-$C_6$-alkynyl, —$C_3$-$C_{10}$-cycloalkyl, —$C_3$-$C_{12}$-heterocycloalkyl, —$C_6$-$C_{12}$-aryl, —$C_5$-$C_{18}$-heteroaryl or —$C_1$-$C_6$-alkoxy are unsubstituted or are substituted one or more times independently of one another by hydroxy, halogen, nitro, cyano, —$C_1$-$C_6$-alkyl, —$C_1$-$C_6$-haloalkyl, —$NR^5R^6$, —$C(O)NR^5R^6$, —$S(O)_2NR^5R^6$, —$NR^5S(O)_2R^6$, —$NR^5C(O)R^6$, —$SR^5$, —$R^5$ or —$OR^5$ where the carbon framework of the —$C_3$-$C_{10}$-cycloalkyl and of the —$C_1$-$C_{10}$-alkyl may comprise one or more times independently of one another nitrogen, oxygen, sulphur atoms, —$NR^4$ or C=O groups or one or more double bonds, or $R^1$ and $R^2$ optionally together form a bridge of 3-10 methylene units, where up to two methylene units are optionally replaced by O, S or —$NR^4$, and where the phenyl radical is optionally substituted one or more times independently of one another by hydroxy, halogen, nitro, cyano, phenyl, —$NR^5R^6$, alkyl or —$OR^5$;

$R^2$ is a hydrogen atom;

$R^3$ and $R^4$ are selected independently of one another from the group comprising hydrogen, —$C_1$-$C_{10}$-alkyl, —$C_2$-$C_6$-alkenyl, —$C_2$-$C_6$-alkynyl, —$C_3$-$C_{10}$-cycloalkyl, —$C_3$-$C_{12}$-heterocycloalkyl, —$C_6$-$C_{12}$-aryl or —$C_1$-$C_{10}$-alkanoyl, where —$C_1$-$C_{10}$-alkyl, —$C_2$-$C_6$-alkenyl, —$C_2$-$C_6$-alkynyl, —$C_3$-$C_{10}$-cycloalkyl, —$C_3$-$C_{12}$-heterocycloalkyl, —$C_6$-$C_{12}$-aryl or —$C_1$-$C_{10}$-alkanoyl is unsubstituted or is substituted one or more times independently of one another by hydroxy, halogen, nitro, cyano, phenyl, —$NR^5R^6$, —$C_1$-$C_{10}$-alkyl, —$SR^5$ or —$OR^5$, or $R^3$ and $R^4$ may, via the respective sulphur atom to which they are attached, form a ring, the size of the ring being 5, 6, 7, 8, 9 or 10 ring atoms, optionally consisting of carbon, nitrogen, oxygen or sulphur atoms;

$R^5$ and $R^6$ are identical or different and are selected independently of one another from the group comprising hydrogen, —$C_1$-$C_{10}$-alkyl, —$C_2$-$C_{10}$-alkenyl, —$C_2$-$C_{10}$-alkynyl, —$C_1$-$C_6$-alkoxy, —$C(=O)$—$C_1$-$C_6$-alkyl, —$C_3$-$C_{10}$-cycloalkyl, —$C_3$-$C_{12}$-heterocycloalkyl, —$C_6$-$C_{12}$-aryl and —$C_5$-$C_{18}$-heteroaryl, where —$C_1$-$C_{10}$-alkyl, —$C_2$-$C_{10}$-alkenyl, —$C_2$-$C_{10}$-alkynyl, —$C_1$-$C_6$-alkoxy, —$C_3$-$C_{10}$-cycloalkyl, —$C_3$-$C_{12}$-heterocycloalkyl, —$C_6$-$C_{12}$-aryl or —$C_5$-$C_{18}$-heteroaryl are unsubstituted or are substituted one or more times independently of one another by hydroxy, halogen, cyano, nitro, —$OR^7$, —$NR^7R^8$, —$C(O)NR^7R^8$, —$C(O)OR^7$ or —$C_1$-$C_6$-alkyl, where —$C_1$-$C_6$-alkyl is unsubstituted or is substituted one or more times independently of one another by halogen, hydroxy, cyano, —$NR^7R^8$, —$OR^7$ or phenyl; or $R^5$ and $R^6$ optionally together form a bridge of 3-10 methylene units, where up to two methylene units are optionally replaced by O, S or $NR^4$;

$R^7$, $R^8$ are identical or different and are selected independently of one another from the group comprising hydrogen, —$C_1$-$C_4$-alkyl, —$C_6$-$C_{12}$-aryl and —$C_5$-$C_{18}$-heteroaryl, where alkyl, aryl, heteroaryl is unsubstituted or is substituted one or more times independently of one another by halogen or alkoxy, or $R^7$ and $R^8$ optionally together form a bridge of 3-10 methylene units, where up to two methylene units are optionally replaced by O, S or —$NR^4$;

n=1, 2, 3, 4, 5, or 6, p=0, 1, 2, 3, 4, 5, or 6, and the N-oxides, solvates, hydrates, stereoisomers, diastereomers, enantiomers and salts thereof.

Another preferred subgroup are compounds in which:

w is CH or N;

Y-Q is $OR^1$;

$R^1$ is selected from the group comprising hydrogen, —$C_1$-$C_6$-alkyl, —$C_1$-$C_4$-hydroxyalkyl, —$C_2$-$C_6$-alkenyl, —$C_2$-$C_6$-alkynyl, —$C_3$-$C_{10}$-cycloalkyl, —$C_3$-$C_{12}$-heterocycloalkyl, —$C_6$-$C_{12}$-aryl, —$C_5$-$C_{18}$-heteroaryl, —$C_1$-$C_6$- alkoxy, —$C_1$-$C_6$-alkoxy-$C_1$-$C_6$-alkoxy, —$C_1$-$C_6$-alkoxy-$C_1$-$C_6$-alkyl, —$C_1$-$C_6$-alkoxy-$C_1$-$C_6$-alkoxy-$C_1$-$C_6$-alkyl, —$(CH_2)_n$—$C_6$-$C_{12}$-aryl, —$(CH_2)_n$—$C_5$-$C_{18}$-heteroaryl, —$(CH_2)_n$—$C_3$-$C_{10}$-cycloalkyl, —$(CH_2)_n$—$C_3$-$C_{12}$-heterocycloalkyl, -phenylene-$(CH_2)_p$—$R^6$, —$(CH_2)_p$—$NR^5R^6$, —$(CH_2)_p$—$NR^4COR^5$, —$(CH_2)_p$—$NR^4CSR^5$, —$(CH_2)_p$—$NR^4S(O)R^5$, —$(CH_2)_p$—$NR^4S(O)_2R^5$, —$(CH_2)_p$—$NR^4CONR^5R^6$, —$(CH_2)_p$—$NR^4COOR^5$, —$(CH_2)_p$—$NR^4C(NH)NR^5R^6$, —$(CH_2)_p$—$NR^4CSNR^5R^6$, —$(CH_2)_p$—$NR^4S(O)NR^5R^6$, —$(CH_2)_p$—$NR^4S(O)_2NR^5R^6$, —$(CH_2)_p$—$COR^5$, —$(CH_2)_p$—$CSR^5$, —$(CH_2)_p$—$S(O)R^5$, —$(CH_2)_p$—$S(O)(NH)R^5$, —$(CH_2)_p$—$S(O)_2R^5$, —$(CH_2)_p$—$S(O)_2NR^5R^6$, —$(CH_2)P$—$SO_{20}R^5$, —$(CH_2)P$—$CO_2R^5$, —$(CH_2)_p$—$CONR^5R^6$, —$(CH_2)_p$—$CSNR^5R^6$, —$OR^5$, —$CHR^5R^6$, —$(CH_2)_p$$SR^5$ and —$CR^5(OH)$—$R^6$, where —$C_1$-$C_6$-alkyl, —$C_2$-$C_6$-alkenyl, —$C_2$-$C_6$-alkynyl, —$C_3$-$C_{10}$-cycloalkyl, —$C_3$-$C_{12}$-heterocycloalkyl, —$C_6$-$C_{12}$-aryl, —$C_5$-$C_{18}$-heteroaryl or —$C_1$-$C_6$-alkoxy are unsubstituted or are substituted one or more times independently of one another by hydroxy, halogen, nitro, cyano, —$C_1$-$C_6$-alkyl, —$C_1$-$C_6$-haloalkyl, —$NR^5R^6$, —$C(O)NR^5R^6$, —$S(O)_2NR^5R^6$, —$NR^5S(O)_2R^6$, —$NR^5C(O)R^6$, —$SR^5$, —$R^5$ or —$OR^5$ where the carbon framework of the —$C_3$-$C_{10}$-cycloalkyl and of the —$C_1$-$C_{10}$-alkyl may comprise one or more times independently of one another nitrogen, oxygen, sulphur atoms, —$NR^4$ or C=O groups or one or more double bonds, or $R^1$ and $R^2$ optionally together form a bridge of 3-10 methylene units, where up to two methylene units are optionally replaced by O, S or —$NR^4$, and where the phenyl radical is optionally substituted one or more times independently of one another by hydroxy, halogen, nitro, cyano, phenyl, —$NR^5R^6$, alkyl or —$OR^5$;

$R^3$ and $R^4$ are selected independently of one another from the group comprising hydrogen, —$C_1$-$C_{10}$-alkyl, —$C_2$-$C_6$-alkenyl, —$C_2$-$C_6$-alkynyl, —$C_3$-$C_{10}$-cycloalkyl, —$C_3$-$C_{12}$-heterocycloalkyl, —$C_6$-$C_{12}$-aryl or —$C_1$-$C_{10}$-alkanoyl, where —$C_1$-$C_{10}$-alkyl, —$C_2$-$C_6$-alkenyl, —$C_2$-$C_6$-alkynyl, —$C_3$-$C_{10}$-cycloalkyl, —$C_3$-$C_{12}$-heterocycloalkyl, —$C_6$-$C_{12}$-aryl or —$C_1$-$C_{10}$-alkanoyl is unsubstituted or is substituted one or more times independently of one another by hydroxy, halogen, nitro, cyano, phenyl, —$NR^5R^6$, —$C_1$-$C_{10}$-alkyl, —$SR^5$ or —$OR^5$, or $R^3$ and $R^4$ may, via the respective sulphur atom to which they are attached, form a ring, the size of the ring being 5, 6, 7, 8, 9 or 10 ring atoms, optionally consisting of carbon, nitrogen, oxygen or sulphur atoms;

$R^5$ and $R^6$ are identical or different and are selected independently of one another from the group comprising hydrogen, —$C_1$-$C_{10}$-alkyl, —$C_2$-$C_{10}$-alkenyl, —$C_2$-$C_{10}$-alkynyl, —$C_1$-$C_6$-alkoxy, —C(=O)—$C_1$-$C_6$-alkyl, —$C_3$-$C_{10}$-cycloalkyl, —$C_3$-$C_{12}$-heterocycloalkyl, —$C_6$-$C_{12}$-aryl and —$C_5$-$C_{18}$-heteroaryl, where —$C_1$-$C_{10}$-alkyl, —$C_2$-$C_{10}$-alkenyl, —$C_2$-$C_{10}$-alkynyl, —$C_1$-$C_6$-alkoxy, —$C_3$-$C_{10}$-cycloalkyl, —$C_3$-$C_{12}$-heterocycloalkyl, —$C_6$-$C_{12}$-aryl or —$C_5$-$C_{18}$-heteroaryl are unsubstituted or are substituted one or more times independently of one another by hydroxy, halogen, cyano, nitro, —$OR^7$, —$NR^7R^8$, —$C(O)NR^7R^8$, —$C(O)OR^7$ or —$C_1$-$C_6$-alkyl, where —$C_1$-$C_6$-alkyl is unsubstituted or is substituted one or more times independently of one another by halogen, hydroxy, cyano, —$NR^7R^8$, —$OR^7$ or phenyl; or $R^5$ and $R^6$ optionally together form a bridge of 3-10 methylene units, where up to two methylene units are optionally replaced by O, S or —$NR^4$;

$R^7$, $R^8$ are identical or different and are selected independently of one another from the group comprising hydrogen, —$C_1$-$C_4$-alkyl, —$C_6$-$C_{12}$-aryl and —$C_5$-$C_{18}$-heteroaryl, where alkyl, aryl, heteroaryl is unsubstituted or is substituted one or more times independently of one another by halogen or alkoxy, or $R^7$ and $R^8$ optionally together form a bridge of 3-10 methylene units, where up to two methylene units are optionally replaced by O, S or —$NR^4$;

n=1, 2, 3, 4, 5, or 6,
p=0, 1, 2, 3, 4, 5, or 6, and
the N-oxides, solvates, hydrates, stereoisomers, diastereomers, enantiomers and salts thereof.

A very particularly preferred subgroup are compounds in which: W, Y-Q, $R^1$, $R^2$, $R^4$, $R^5$, $R^6$, $R^7$, $R^8$, n and p are as defined above, and $R^3$ is a —$C_1$-$C_{10}$-alkyl group; the N-oxides, solvates, hydrates, stereoisomers, diastereomers, enantiomers and salts thereof.

The following compounds are even more preferred:

N-(1-methylethyl)-6-[[(S)-methyloxidophenyl-$\lambda^4$-sulphanylidene]amino]-4-quinazolinamine;

6-[(dimethyloxido-$\lambda^4$-sulphanylidene)amino]-N-(1-methylethyl)-4-quinazolin-amine;

4-fluoro-2-methyl-5-[[6-[(R)-(methyloxido-phenyl-$\lambda^4$-sulphanylidene]amino]-4-quinazolinyl]amino]-phenol;

4-fluoro-2-methyl-5-[[6-[(S)-(methyloxido-phenyl-$\lambda^4$-sulphanylidene]amino]-4-quinazolinyl]amino]-phenol;

5-[[6-[(dimethyloxido-$\lambda^4$-sulphanylidene)amino]-4-quinazolinyl]amino]-4-fluoro-2-methylphenol;

4-methyl-3-[[6-[(R) — (methyloxidophenyl-$\lambda^4$-sulphanylidene)amino]-4-quinazolinyl]amino]-phenol;

4-methyl-3-[[6-[(S)-(methyloxidophenyl-$\lambda^4$-sulphanylidene)amino]-4-quinazolinyl]amino]-phenol;

3-[[6-[(dimethyloxido-$\lambda^4$-sulphanylidene)amino]-4-quinazolinyl]amino]-4-methyl-phenol 4-methyl-3-[[6-[[(R)-methyloxidophenyl-$\lambda^4$-sulphanylidene]amino]-4-quinolinyl]amino]phenol;

4-methyl-3-[[6-[[(S)-methyloxidophenyl-$\lambda^4$-sulphanylidene]amino]-4-quinolinyl]amino]phenol;

3-[[6-[[(R)-methyloxidophenyl-$\lambda^4$-sulphanylidene]amino]-4-quinolinyl]amino]-phenol;

3-[[6-[[(S)-methyloxidophenyl-$\lambda^4$-sulphanylidene]amino]-4-quinolinyl]amino]-phenol;

3-[[6-[(dimethyloxido-$\lambda^4$-sulphanylidene)amino]-4-quinolinyl]amino]-4-methyl-phenol;

3-methoxy-5-[[6-[[(R)-methyloxidophenyl-$\lambda^4$-sulphanylidene]amino]-4-quinolinyl]amino]phenol;

3-methoxy-5-[[6-[[(S)-methyloxidophenyl-$\lambda^4$-sulphanylidene]amino]-4-quinolinyl]amino]phenol;

3-[[6-[(dimethyloxido-$\lambda^4$-sulphanylidene)amino]-4-quinolinyl]amino]-5-methoxyphenol;

3-methoxy-5-[(6-{[oxido(diphenyl)-$\lambda^4$-sulphanylidene]amino}quinolin-4-yl)amino]phenol;

3-[(6-{[dimethyl(oxido)-$\lambda^4$-sulphanylidene]amino}quinolin-4-yl)amino]-4-methylphenol;

4-chloro-3-[(6-{[dimethyl(oxido)-$\lambda^4$-sulphanylidene]amino}quinolin-4-yl)amino]phenol;

4-chloro-3-[(6-{[(R)-methyl(oxido)phenyl-$\lambda^4$-sulphanylidene]amino}quinolin-4-yl)amino]phenol;

4-methyl-3-[(6-{[oxido(diphenyl)-$\lambda^4$-sulphanylidene]amino}quinolin-4-yl)amino]phenol;

3-[(6-{[diethyl(oxido)-$\lambda^4$-sulphanylidene]amino}quinolin-4-yl)amino]-5-methoxyphenol;

3-[(6-{[ethyl(methyl)oxido-$\lambda^4$-sulphanylidene]amino}quinolin-4-yl)amino]-5-methoxyphenol;

3-methoxy-5-[(6-{[oxido(dipropyl)-$\lambda^4$-sulphanylidene]amino}quinolin-4-yl)amino]phenol;

3-[(6-{[cyclohexyl(methyl)oxido-λ$^4$-sulphanylidene]
  amino}quinolin-4-yl)amino]-5-methoxyphenol;
3-methoxy-5-({6-[(1-oxidotetrahydro-1H-1λ$^4$-thiophen-1-
  ylidene)amino]quinolin-4-yl}amino)phenol;
3-[(6-{[ethyl(oxido)phenyl-λ$^4$-sulphanylidene]
  amino}quinolin-4-yl)amino]-5-methoxyphenol;
3-[(6-{[(2-fluorophenyl)(methyl)oxido-λ$^4$-sulphanylidene]
  amino}quinolin-4-yl)amino]-5-methoxyphenol;
3-[(6-{[(4-fluorophenyl)(methyl)oxido-λ$^4$-sulphanylidene]
  amino}quinolin-4-yl)amino]-5-methoxyphenol;
3-[(6-{[(4-chlorophenyl)(methyl)oxido-λ$^4$-sulphanylidene]
  amino}quinolin-4-yl)amino]-5-methoxyphenol;
3-[(6-{[(4-methylphenyl)(methyl)oxido-λ$^4$-sulphanylidene]
  amino}quinolin-4-yl)amino]-5-methoxyphenol;
3-[(6-{[(3-methylphenyl)(methyl)oxido-λ$^4$-sulphanylidene]
  amino}quinolin-4-yl)amino]-5-methoxyphenol;
3-[(6-{[(4-methoxyphenyl)(methyl)oxido-λ$^4$-sulpha-
  nylidene]amino}quinolin-4-yl)amino]-5-methoxyphenol;
3-methoxy-5-{[6-({methyl[4-(1-methylethyl)phenyl]oxido-
  λ$^4$-sulphanylidene}amino]quinolin-4-yl}amino)phenol;
3-[(6-{[(2,4-dimethylphenyl)(methyl)oxido-λ$^4$-sulpha-
  nylidene]amino}quinolin-4-yl)amino]-5-methoxyphenol;
3-methoxy-5-[(6-{[methyl(naphthalene-2-yl)oxido-λ$^4$-sul-
  phanylidene]amino}quinolin-4-yl)amino]phenol;
N-[3-(N-{4-[(3-hydroxy-5-methoxyphenyl)amino]quinolin-
  6-yl}-S-methylsulphonimidoyl)phenyl]acetamide;
3-[(6-{[tert-butyl(methyl)oxido-λ$^4$-sulphanylidene]
  amino}quinolin-4-yl)amino]-5-methoxyphenol;
3-methoxy-5-[(6-{[methyl(naphthalen-1-yl)oxido-λ$^4$-sul-
  phanylidene]amino}quinolin-4-yl)amino]phenol;
3-bromo-5-[[6-[[(R)-methyloxidophenyl-λ$^4$-sulpha-
  nylidene]amino]quinolin-4-yl]amino]phenol;
3-methyl-5-[[6-[[(R)-methyloxidophenyl-λ$^4$-sulpha-
  nylidene]amino]quinolin-4-yl]amino]phenol;
3-[(6-{[(R)-methyl(oxido)phenyl-λ$^4$-sulphanylidene]
  amino}quinolin-4-yl)amino]-5-(trifluoromethyl)phenol;
N-(6-chloro-1H-indazol-4-yl)-6-{[(R)-methyl(oxido)phe-
  nyl-λ$^4$-sulphanylidene]amino}quinolin-4-amine; and
3-[(6-{[dimethyl(oxido)-λ$^4$-sulphanylidene]
  amino}quinolin-4-yl)oxy]-5-methoxyphenol.

It has been found that the compounds according to the invention are able to inhibit receptor tyrosine kinases, especially Eph receptors.

Alkyl means in each case a straight-chain or branched alkyl radical such as, for example, methyl, ethyl, propyl, isopropyl, butyl, isobutyl, sec-butyl, tert-butyl, pentyl, isopentyl, hexyl, heptyl, octyl, nonyl and decyl.

Alkoxy means in each case a straight-chain or branched alkoxy radical such as, for example, methyloxy, ethyloxy, propyloxy, isopropyloxy, butyloxy, isobutyloxy, sec butyloxy, pentyloxy, isopentyloxy, hexyloxy, heptyloxy, octyloxy, nonyloxy or decyloxy.

—$C_1$-$C_6$-Haloalkyl means an alkyl group which is substituted one, two, three or at most as many times as it has carbon atoms, by halogen atom, such as, for example, trifluoromethyl or pentafluoroethyl.

The alkenyl substituents are in each case straight-chain or branched, with the following radicals being meant for example: vinyl, propen-1-yl, propen-2-yl, but-1-en-1-yl, but-1-en-2-yl, but-2-en-1-yl, but-2-en-2-yl, 2-methylprop-2-en-1-yl, 2-methylprop-1-en-1-yl, but-1-en-3-yl, but-3-en-1-yl, allyl.

Alkynyl means in each case a straight-chain or branched alkynyl radical which comprises two to six, preferably two to four, C atoms. Examples of suitable radicals are the following: ethynyl, propyn-1-yl, propyn-3-yl, but-1-yn-1-yl, but-1-yn-4-yl, but-2-yn-1-yl, but-1-yn-3-yl.

Cycloalkyl means monocyclic alkyl rings such as cyclopropyl, cyclobutyl, cyclopentyl, cyclohexyl or cycloheptyl, but also bicyclic rings or tricyclic rings such as, for example, adamantanyl. The cycloalkyl rings may be unsubstituted or substituted one or more times. Cycloalkyls according to this invention comprise $C_3$-$C_{12}$ carbon atoms; cycloalkyls having $C_3$-$C_{10}$ carbon atoms are preferred, and cycloalkyls having $C_3$-$C_6$ carbon atoms are particularly preferred.

An aryl radical has 6-12 carbon atoms in each case: "—$C_6$-$C_{12}$-aryl". The radical may be mono- or bicyclic, for example naphthyl, biphenyl and, in particular, phenyl.

The heteroaryl radical includes an aromatic ring system which comprises in each case 5-18 ring atoms, preferably 5 to 10 ring atoms and particularly preferably 5 to 7 ring atoms and, instead of the carbon, one or more identical or different heteroatoms from the group of oxygen, nitrogen or sulphur. The radical may be mono-, bi- or tricyclic and additionally in each case benzo-fused. However, only those combinations which are sensible in the view of a skilled person, especially in relation to the ring tension, are meant.

The heteroaryl rings may be unsubstituted or substituted one or more times. Examples which may be mentioned are: thienyl, furanyl, pyrrolyl, oxazolyl, thiazolyl, imidazolyl, pyrazolyl, isoxazolyl, isothiazolyl, oxadiazolyl, triazolyl, thiadiazolyl, pyridyl, pyridazinyl, pyrimidinyl, pyrazinyl, triazinyl and benzo derivatives of these radicals such as, for example, 1,3-benzodioxolyl, benzofuranyl, benzothienyl, benzoxazolyl, benzimidazolyl, indazolyl, indolyl, isoindolyl, oxepinyl, azocinyl, indolizinyl, indolyl, isoindolyl, indazolyl, benzimidazolyl, purinyl, quinolinyl, isoquinolinyl, cinnolinyl, phthalazinyl, quinazolinyl, quinoxalinyl, naphthyridinyl, pteridinyl, carbazolyl, acridinyl, phenazinyl, phenothiazinyl, phenoxazinyl, xanthenyl etc.

Halogen means in each case fluorine, chlorine, bromine or iodine.

$C_3$-$C_{12}$-Heterocycloalkyl stands for an alkyl ring, which is not aromatic or only partially aromatic, including 3-12 carbon atoms, preferably including 3 to 10 carbon atoms and particularly preferably including 3 to 6 carbon atoms, which is interrupted by at least one of the following atoms nitrogen, oxygen and/or sulphur in the ring and which may optionally be interrupted by one or more identical or different —(CO)—, —SO— or —SO$_2$— groups in the ring and optionally comprises one or more double bonds in the ring. However, only those combinations which are sensible in the view of a skilled person, especially in relation to the ring tension, are meant. $C_3$-$C_{12}$-Heterocycloalkyls according to this invention are monocyclic, but also bicyclic or tricyclic. Examples of monocyclic heterocyclyls which may be mentioned are: oxiranyl, oxetanyl, aziridinyl, azetidinyl, tetrahydrofuranyl, pyrrolidinyl, dioxolanyl, imidazolidinyl, pyrazolidinyl, dioxanyl, piperidinyl, morpholinyl, dithianyl, thiomorpholinyl, piperazinyl, trithianyl, quinuclidinyl etc.

As used in this application, "$C_1$-$C_{10}$" refers, for example in connection with the definition of "$C_1$-$C_{10}$-alkyl", to an alkyl group having a finite number of 1 to 10 carbon atoms, i.e. 1, 2, 3, 4, 5, 6, 7, 8, 9 or 10 carbon atoms. The definition of "$C_1$-$C_{10}$" is further interpreted to mean that every possible sub-range such as, for example, $C_1$-$C_{10}$, $C_2$-$C_9$, $C_3$-$C_8$, $C_4$-$C_7$, $C_5$-$C_6$, $C_1$-$C_2$, $C_1$-$C_3$, $C_1$-$C_4$, $C_1$-$C_5$, $C_1$-$C_6$, $C_1$-$C_7$, $C_1$-$C_8$, $C_1$-$C_9$, $C_1$-$C_{10}$, preferably $C_1$-$C_2$, $C_1$-$C_3$, $C_1$-$C_4$, $C_1$-$C_5$, $C_1$-$C_6$; preferably $C_1$-$C_4$ is also included in the definition.

In analogy thereto "$C_2$-$C_{10}$" refers, for example in connection with the definition of "$C_2$-$C_{10}$-alkenyl" and "$C_2$-$C_{10}$-alkynyl", to an alkenyl group or alkynyl group having a finite number of 2 to 10 carbon atoms, i.e. 2, 3, 4, 5, 6, 7, 8, 9 or 10 carbon atoms. The definition of "$C_2$-$C_{10}$" is interpreted to mean that every possible sub-range such as, for example, $C_2$-$C_{10}$, $C_3$-$C_9$, $C_4$-$C_8$, $C_5$-$C_7$, $C_2$-$C_3$, $C_2$-$C_4$, $C_2$-$C_5$, $C_2$-$C_6$, $C_2$-$C_7$, $C_2$-$C_8$, $C_2$-$C_9$, preferably $C_2$-$C_4$, is also included in the definition.

Furthermore, "$C_1$-$C_6$" refers, for example in connection with the definition of "$C_1$-$C_6$-alkoxy" to an alkoxy group having a finite number of 1 to 6 carbon atoms, i.e. 1, 2, 3, 4, 5 or 6 carbon atoms. The definition of "$C_1$-$C_6$" is interpreted to mean that every possible sub-range such as, for example, $C_1$-$C_6$, $C_2$-$C_5$, $C_3$-$C_4$, $C_1$-$C_2$, $C_1$-$C_3$, $C_1$-$C_4$, $C_1$-$C_5$, $C_1$-$C_6$; preferably $C_1$-$C_4$, is also included in the definition.

All statements of ranges in the application which are not explicitly mentioned here are defined analogously like the ranges "$C_1$-$C_{10}$", "$C_2$-$C_{10}$" and "$C_1$-$C_6$" mentioned above as examples.

Isomers mean chemical compounds of the same molecular formula but different chemical structure. A distinction is made in general between constitutional isomers and stereoisomers. Constitutional isomers have the same molecular formula but differ through the mode of linkage of their atoms or atomic groups. Included herein are functional isomers, positional isomers, tautomers or valence isomers. Stereoisomers have fundamentally the same structure (constitution) and thus also the same molecular formula, but differ through the spatial arrangement of the atoms. In general, configurational isomers and conformational isomers are distinguished. Configurational isomers are stereoisomers which can be interconverted only by breaking bonds. These include enantiomers, diastereomers and E/Z (cis/trans) isomers. Enantiomers are stereoisomers which are related to one another as image and mirror image and have no plane of symmetry, for example, the compounds of the invention may exist either as (R)- or (S)-sulphoximine, or as a mixture of (R)- and (S)-sulphoximine. All stereoisomers which are not enantiomers are referred to as diastereomers. E/Z (cis/trans) isomers at double bonds are a special case. Conformational isomers are stereoisomers which can be interconverted by rotation of single bonds. To distinguish the types of isomerism from one another, see also the IUPAC rules section E (*Pure Appl. Chem.* 1976, 45, 11-30).

The quinoline and quinazoline derivatives according to the invention having the general formula (A) also encompass the possible tautomeric forms and include the E or Z isomers or, if a chiral centre is present, also the racemates and enantiomers. By these are also meant double-bond isomers.

The quinoline and quinazoline derivatives according to the invention may also exist in the form of solvates, in particular of hydrates, in which case the compounds according to the invention accordingly comprise polar solvents, in particular water, as structural element of the crystal lattice of the compounds according to the invention. The proportion of polar solvent, in particular water, may be in a stoichiometric or else non-stoichiometric ratio. Terms used in connection with stoichiometric solvates, hydrates are also hemi-, (semi-), mono-, sesqui-, di-, tri-, tetra-, penta-, etc. solvates or hydrates.

N-Oxides means that at least one nitrogen of the compounds according to the invention of the general formula (A) may be oxidized.

If an acidic function is present, suitable salts are the physiologically tolerated salts of organic and inorganic bases such as, for example, the readily soluble alkali metal and alkaline earth metal salts, and salts of N-methylglucamine, dimethylglucamine, ethylglucamine, lysine, 1,6-hexandiamine, ethanolamine, glucosamine, sarcosine, serinol, trishydroxymethylaminomethane, aminopropanediol, Sovak base, 1-amino-2,3,4-butanetriol.

If a basic function is present, the physiologically tolerated salts of organic and inorganic acids are suitable, such as hydrochloric acid, hydrobromic acid, sulphuric acid, phosphoric acid, oxalic acid, malonic acid, maleic acid, citric acid, succinic acid, tartaric acid and others.

Functional groups may be protected where appropriate by protective groups during the reaction sequence. Such protective groups may be inter alia esters, amides, ketals/acetals, nitro groups, carbamates, alkyl ethers, allyl ethers, benzyl ethers or silyl ethers. Compounds which may occur as constituent of silyl ethers inter alia are such as, for example, trimethylsilyl (TMS), tert-butyldimethylsilyl (TBDMS), tert-butyldiphenylsilyl (TBDPS), triethylsilyl (TES), etc. The preparation of selected intermediates provided with protective groups is described in the experimental section.

The quinoline and quinazoline derivatives according to the invention having the general formula (A) inhibit receptor tyrosine kinases, especially Eph kinases, on which their effect is also based, for example in the treatment of disorders in which angiogenesis, lymphangiogenesis or vasculogenesis are involved, of disorders of the blood vessels, disorders caused by hyperproliferation of body cells, or chronic or acute neurodegenerative disorders. The present quinoline and quinazoline derivatives having the general formula (A) can accordingly be used as medicaments.

Treatments are preferably carried out on humans, but also on related mammalian species such as, for example, dog and cat.

Angiogenic and/or vasculogenic disorders can be treated by the growth of blood vessels being inhibited (antiangiogenic) or promoted (proangiogenic). Antiangiogenic uses take place for example in tumour angiogenesis, endometriosis, in diabetes-related or other retinopathies or in age-related macular degeneration. Proangiogenic uses take place for example in myocardial infarction or acute neurodegenerative disorders due to ischaemias of the brain or neurotraumata.

Blood vessel disorders mean stenoses, arterioscleroses, restenoses or inflammatory diseases such as rheumatoid arthritis.

Hyperproliferative disorders mean solid tumours, non-solid tumours or non-carcinogenic hyperproliferation of cells in the skin, where solid tumours mean inter alia tumours of the breast, colon, kidney, lung and/or brain. Non-solid tumours mean inter alia leukaemias, and non-carcinogenic hyperproliferation of cells in the skin means inter alia psoriasis, eczemas, scleroderma or benign prostatic hypertrophy.

Chronic neurodegenerative disorders mean inter alia Huntington's disease, amyotrophic lateral sclerosis, Parkinson's disease, AIDS-induced dementia or Alzheimer's disease.

The quinoline and quinazoline derivatives having the general formula (A) can likewise be used for diagnostic purposes in vitro or in vivo for identifying receptors in tissues by means of autoradiography and/or PET.

The substances can in particular for diagnostic purposes also be radiolabelled. For use of the quinoline and quinazoline derivatives according to the invention as medicaments, they are converted into the form of a pharmaceutical product which, besides the active ingredient, comprises pharmaceutical, organic or inorganic inert carrier materials which are suitable for enteral or parenteral administration, such as, for example, water, gelatin, gum arabic, lactose, starch, magnesium stearate, talc, vegetable oils, polyalkylene glycols etc. The pharmaceutical products may be in solid form, for example as tablets, coated tablets, suppositories, capsules or in liquid form, for example as solutions, suspensions or emulsions. They additionally comprise where appropriate excipients such as preservatives, stabilizers, wetting agents or emulsifiers; salts to modify the osmotic pressure or buffers.

The present invention likewise relates to these pharmaceutical products.

Suitable for parenteral use are in particular solutions for injection or suspensions, especially aqueous solutions of the active compounds in polyhydroxyethoxylated castor oil.

Carrier systems which can also be used are surface-active excipients such as salts of bile acids or animal or vegetable phospholipids, but also mixtures thereof, and liposomes or their constituents.

Suitable for oral use are, in particular, tablets, coated tablets or capsules with talc and/or hydrocarbon carriers or binders, such as, for example, lactose, maize starch or potato starch. Use can also take place in liquid form, for example as solution, to which a sweetener is added where appropriate.

The present invention likewise relates to the enteral, parenteral and oral administrations.

The dosage of the active ingredients may vary depending on the route of administration, age and weight of the patient, nature and severity of the disorder to be treated and similar factors. The daily dose is 0.5-1000 mg, it being possible to give the dose as a single dose to be administered once or divided into two or more daily doses.

The present invention likewise relates to medicaments for the treatment of the abovementioned disorders, which comprise at least one quinoline or quinazoline derivative having the general formula (A), where the medicaments may where appropriate comprise suitable formulation substances and carriers.

Where no description is given for the preparation of the starting compounds, they are known to the skilled person or can be prepared in analogy to known compounds or to processes described herein. It is likewise possible to carry out all the reactions described herein in parallel reactors or using combinatorial operating techniques.

The mixtures of isomers can be fractionated by conventional methods such as, for example, crystallization, chromatography or salt formation into the enantiomers or E/Z isomers.

Salts are prepared in a conventional way by mixing a solution of the compound having the general formula (A) with the equivalent amount or an excess of a base or acid, which is in solution where appropriate, and removing the precipitate or working up the solution in a conventional way.

The present invention likewise relates to the process for preparing the quinoline and quinazoline derivatives according to the invention.

The intermediates preferably used for preparing the quinoline and quinazoline derivatives according to the invention having the general formula (A) are the following compounds having the general formulae (I) to (VII).

General Description of the Preparation of the Compounds According to the Invention:

Scheme 1 a)

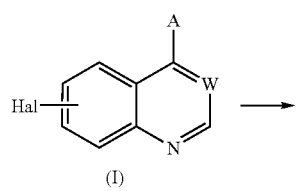

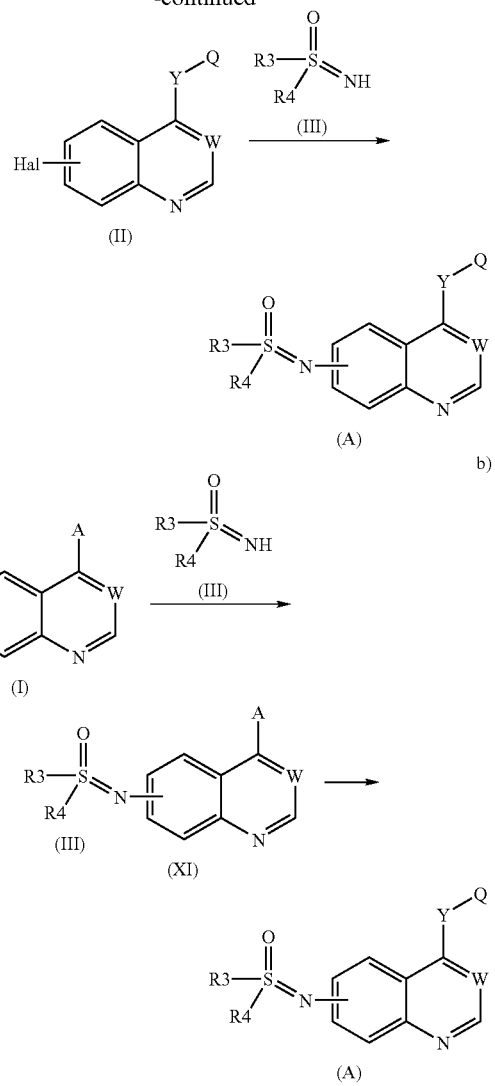

Quinoline and quinazoline derivatives according to the invention having the general formula (A) can be prepared for example by the route shown in scheme 1a), in which the radical A can be for example halogen or —OS(O)$_2$C$_n$F$_{2n+1}$ with n=1-3, Hal is a halogen atom such as chloride, bromide or iodide and the radicals R3 and R4 may be as described in the claims, and the radicals W and Y-Q have the same meaning as in the general formula (A). The required starting materials are either commercially available or are prepared by processes disclosed in the literature, or in analogy to processes disclosed in the literature, or as described below.

Compounds having the general formula (II) are formed by substituting a suitable functional group A by a nucleophile such as primary or secondary amines or alcohols which are provided where appropriate with protective groups of a compound having the general formula (I) (e.g. *J. Med. Chem.*, 2005, 48, 3354-3363; *J. Med. Chem.*, 1995, 38, 3482-3287). The addition of bases may be necessary in some circumstances for this reaction (*J. Med. Chem.*, 2001, 44, 3031-3038). Compounds of the (II) type are then converted by using sulphoximines e.g. having the general formula (III) in the presence of suitable transition metal catalysts into compounds having the general formula (A). Introduction of the sulphoximines via the imine nitrogen on the aromatic and heteroaromatic rings can be achieved by palladium-, nickel- or copper-catalysed cross-coupling reactions. Reactions of this type are described for example in (a) C. Bolm, J. P. Hildebrandt, *Tetrahedron Lett.* 1998, 39, 5731-5734; b) M. Harmata, N. Parvi, Angew. Chemie 1999, 38, 2577-2579; c) C. Bolm, J. P. Hildebrandt, *J. Org. Chem.* 2000, 65, 169; d) C. Bolm, J. P. Hildebrand, J. Rudolph, *Synthesis* 2000, 911-913; e) C. Bolm, M. Verrucci, O. Simic, P. G. Cozzi, G. Raabe, H. Okamura, *Chem. Commun.* 2003, 22, 2826-2827; f) G. Y. Cho, P. Rémy, J. Jansson, C. Moessner, C. Bolm, *Org. Lett.* 2004, 6, 3293-3296).

It is also possible as an alternative firstly to react compounds having the general formula (I) with sulphoximines of the general formula (III) under the abovementioned reaction conditions to give compounds of the general formula (XI). The latter can then be reacted by substitution of a suitable functional group A by a nucleophile such as primary or secondary amines or alcohols, which are provided where appropriate with protective groups, under the conditions detailed above to give compounds having the general formula (A) (scheme 1b).

Scheme 2

General description of the preparation of sulphoximine building blocks
A) via sulphoxide

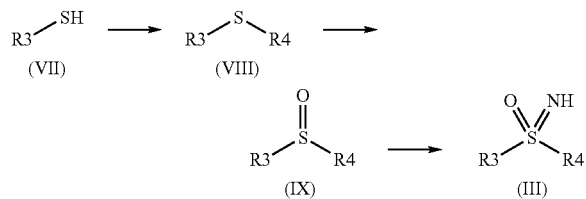

B) via (substituted) sulphoximine

Scheme 3

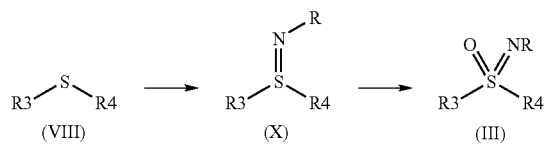

Scheme 2 shows possible ways of preparing the sulphoximine building blocks with sulphoxides as intermediates. Thioethers of the (VIII) type can be prepared starting from thiols of the (VII) type (e.g. *J. Med. Chem.*, 2002, 45, 3972-3978; *Tetrahedron Lett.*, 2006, 47, 5781-5784). These thioethers can be converted for example by oxidation with hydrogen peroxide (*Synthesis,* 2004, 227-232) into sulphoxides of the (IX) type. Sulphoxides of the (IX) type can then be converted for example by reaction with sodium azide in oleum into the sulphoximines (III) (M. Reggelin, C. Zur, *Synthesis,* 2000, 1, 1). The reaction can be carried out in organic solvents such as, for example, chloroform. Alternative ways of preparing sulphoximines from sulphoxides are likewise described, e.g. using the following reagents
a) TsN₃ ((a) R. Tanaka, K. Yamabe, *J. Chem. Soc. Chem. Commun.* 1983, 329; (b) H. Kwart, A. A. Kahn, *J. Am. Chem. Soc.* 1967, 89, 1959))
b) N-tosyliminophenyliodinane and cat. amounts of copper (I) triflate (J. F. K. Müller, P. Vogt, *Tetrahedron Lett.* 1998, 39, 4805)
c) Boc azide and cat. amounts of iron(II) chlorides (T. Bach, C. Korber, *Tetrahedron Lett.* 1998, 39, 5015)
d) o-mesitylenesulphonylhydroxylamine (MSH) (C. R. Johnson, R. A. Kirchhoff, H. G. Corkins, *J. Org. Chem.* 1974, 39, 2458).
e) [N-(2-(trimethylsilyl)ethanesulphonyl)imino]phenyliodinane (PhI=NSes) (S. Cren, T. C. Kinahan, C. L. Skinner and H. Tye, *Tetrahedron Lett.* 2002, 43, 2749).
f) trifluoroacetamide, iodobenzene diacetate, magnesium oxide and [Rh₂(OAc)₄] (H. Okamura and C. Bolm, *Org. Lett.* 2004, 6, 1305).
g) chloramineT (C. R. Johnson, R. A. Kirchhoff, R. J. Reischer, G. F. Katekar, *J. Am. Chem. Soc.* 1973, 95, 13, 4287-4291)

Scheme 3 shows possible ways of preparing the sulphoximine building blocks with sulphimines as intermediates. Thioethers of the type (VIII) can be reacted with chloramineT (A. L. Marzinzik, K. B. Sharpless, *J. Org. Chem.* 2001, 66, 594-596) or with other reagents mentioned in the preceding paragraph to give sulphimines of the type (X). In the case of chloramineT, tosylated sulphimines are obtained. These can be reacted by oxidation, e.g. with hydrogen peroxide, meta-chloroperbenzoic acid, sodium periodate or the like (C. R. Johnson, O. Lavergne, *J. Org. Chem.* 1989, 54, 986-988) to give sulphoximines of the type (III). Elimination of the tosyl group can be carried out either before or after the oxidation, e.g. with acid or with sodium anthracenide (C. R. Johnson, O. Lavergne, *J. Org. Chem.* 1989, 54, 986-988).

In relation to structure and configuration, sulphoximines generally have high stability (C. Bolm, J. P. Hildebrand, *J. Org. Chem.* 2000, 65, 169). These properties of the functional group often permit drastic conditions for subsequent reactions. Enantiomer pure sulphoximines are also employed as auxiliaries in the diastereoselective synthesis ((a) S. G. Pyne, *Sulfur Reports* 1992, 12, 57; (b) C. R. Johnson, *Aldrichchimica Acta* 1985, 18, 3). The preparation of enantiomer pure sulphoximines is likewise described, e.g. by racemate resolution using enantiomer pure camphor-10-sulphonic acid ((a) C. R. Johnson, C. W. Schroeck, *J. Am. Chem. Soc.* 1973, 95, 7418; (b) C. S. Shiner, A. H. Berks, *J. Org. Chem.* 1988, 53, 5543). A further method for preparing optically active sulphoximines is the stereoselective imination of optically active sulphoxides using MSH ((a) C. Bolm, P. Müller, K. Harms, *Acta Chem. Scand.* 1996, 50, 305; (b) Y. Tamura, J. Minamikawa, K. Sumoto, S. Fujii, M. Ikeda, *J. Org. Chem.* 1973, 38, 1239) or trifluoroacetamide, iodobenzene diacetate, magnesium oxide and [Rh₂(OAc)₄] (H. Okamura and C. Bolm, *Org. Lett.* 2004, 6, 1305).

Experimental Description of the Preparation of the Intermediates and of The Products According to the Invention of the General Formula (A).
General Part
The naming of the chemical structures took place using the software tool Autonom 2000 for ISIS/Draw [MDL Information Systems Inc. (Elsevier MDL)].
Description of the Preparation of Selected Intermediates
Intermediates whose preparation is not described in detail below are commercially available, can be obtained in analogy to the described methods or according to literature procedures.
Preparation of Intermediates of the HNR1R2 Type
Building blocks of the HNR1R2 type which have both NH and OH functionalities can be employed protected in a suitable manner. For example the tert-butyldimethylsilyl protective group (TBDMS) is used for the alcohol functions. The respective protective groups are introduced by using conventional methods (e.g. T. W. Greene, P. G. M. Wuts, Protective groups in organic synthesis, 4th edition, 2006, Wiley-VCH (Weinheim) and references cited therein).

Intermediate 1

Preparation of 3-(tert-butyldimethylsilanyloxy)phenylamine

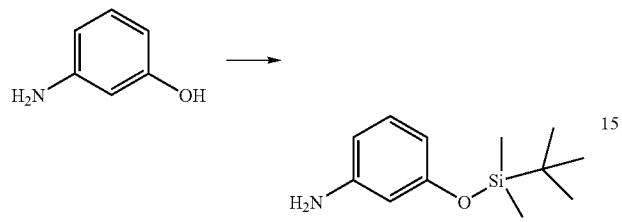

6.81 g (100 mmol) of imidazole and 9.04 g (60 mmol) of tert-butyl-dimethylsilyl chloride are added to a solution of 5.46 g (50 mmol) of 3-aminophenol in 13.5 ml of N,N-dimethylformamide. The resulting reaction mixture is stirred at room temperature for 12 h. After addition of a saturated aqueous sodium chloride solution, the mixture is extracted with ethyl acetate. The organic phase is dried over sodium sulphate. The crude product obtained after removal of the solvent by distillation is purified by flash chromatography. 7.62 g (34 mmol, 68%) of the desired product are obtained.

$^1$H-NMR (400 MHz, D6-DMSO): δ=0.16 (s, 6H); 0.94 (s, 9H); 5.01 (s, 2H); 5.98 (dd, 1H); 6.09 (t, 1H); 6.16 (dt, 1H); 6.85 (t, 1H).

Preparation of Sulphoximines

Sulphoximines can be prepared starting from commercially available sulphoxides for example as follows. The preparation of sulphoxides starting from thiols or sulphides has been described many times in the literature (see above). In the text below, in each case, one example is described for the reaction sequence according to scheme 2 (method E) and according to scheme 3 (method F)

Method E

Intermediate 2

Preparation of 5,5-dimethylsulphoximine

60 g (768 mmol) of dry dimethyl sulphoxide and 46 g (705 mmol) of sodium azide in 500 ml of dichloromethane are cooled to 0° C. Over a period of 1 h at 0° C., 160 ml of concentrated sulphuric acid are added. The resulting reaction mixture is cautiously warmed to 42° C. and stirred at this temperature for 24 h. The reaction mixture is then cooled and ice is added until all the solid residues have dissolved. The organic phase is separated off and the aqueous phase is adjusted to pH 10 by adding 40% strength aqueous sodium hydroxide solution. The solution is concentrated by evaporating part of the aqueous phase. The resulting residue is stirred with 1 l of ethanol at 50° C. The remaining solid is filtered off, and the resulting solution is again concentrated as far as possible. The residue is stirred with 500 ml of dichloromethane. The remaining solid is filtered off and washed with dichloromethane. The filtrate is freed of solvent. 25 g (268 mmol, 38%) of the desired product are finally obtained by vacuum distillation.

Boiling point: 100-106° C. at 0.2 torr; melting point: 52° C.

Method F

Intermediate 3 a) Preparation of N-(diethyl-λ$^4$-sulphanylidene)-4-methylbenzene-sulphonamide

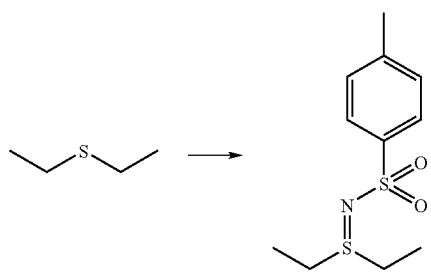

1.87 g (6.65 mmol) of chloramineT trihydrate are added to 500 mg (5.54 mmol) of diethyl sulphide in 15 ml of acetonitrile at room temp. After stirring overnight, 20 ml of dichloromethane are added, and the solid is filtered off. The solvent is removed from the filtrate under reduced pressure. 10 ml of 2:1 cyclohexane:ethyl acetate are added to the residue, and the solid is filtered off with suction. 1.42 g (99%) of the title compound are obtained.

$^1$H-NMR (400 MHz, D6-DMSO): δ=1.03 (t, 6H), 2.77-2.88 and 2.90-3.01 (2 m, AB signal, 4H), 2.35 (s, 3H), 7.30 (d, 2H), 7.61 (d, 2H). MS (ESpos): 260.6 [M+H]$^+$.

b) Preparation of N-[diethyl(oxido)-λ$^4$-sulphanylidene-4-methylbenzene-sulphonamide

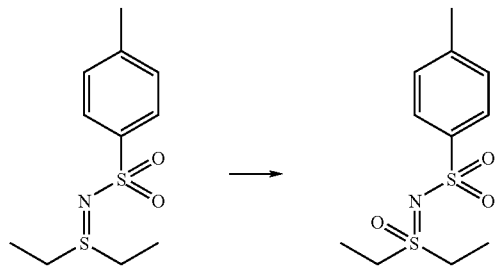

3.1 ml (3.5 g, 31 mmol) of a 30% strength hydrogen peroxide solution and 1.6 g (12 mmol) of potassium carbonate are added to 1.40 g (5.40 mmol) of N-(diethyl-λ$^4$-sulphanylidene)-4-methylbenzenesulphonamide in 15 ml of ethanol and 3 ml of acetonitrile. After stirring overnight, 50 ml of water and 50 ml of dichloromethane are added. The organic phase is dried over magnesium sulphate and freed of solvent under reduced pressure. 1.48 g (100%) of the title compound are obtained as residue.

$^1$H-NMR (400 MHz, D6-DMSO): δ=1.27 (t, 6H), 2.37 (s, 3H), 3.54 (m$_c$, 4H), 7.34 (d, 2H), 7.71 (d, 2H). MS (ESpos): 276.2 [M+H]$^+$.

c) Preparation of S,S-diethylsulphoximine

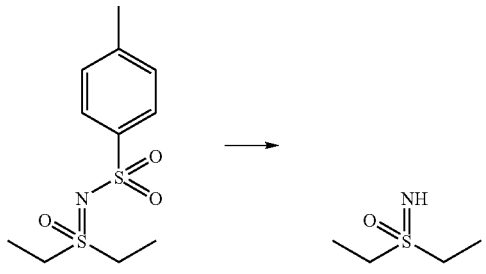

Sodium anthracenide solution (prepared by adding 0.68 g of sodium to 5.4 g of anthracene in 30 ml of 1,2-dimethoxyethane and subsequently stirring at room temp. for 3 h) is added to 500 mg (1.82 mmol) of N-[diethyl(oxido)-λ$^4$-sulphanylidene-4-methylbenzenesulphonamide in 5.5 ml of 1,2-dimethoxy-ethane until decolourization no longer occurs. The pH is then made acidic with 1 N hydrochloric acid, and extractions are carried out successively with 10 ml of dichloromethane and 10 ml of diethyl ether. The aqueous phase is basified with sodium carbonate. The water is removed under reduced pressure, and the residue is stirred with dichloromethane. After filtration, the solvent is removed from the filtrate under reduced pressure, and the residue is dried under high vacuum. 204 mg (93%) of the title compound are obtained. $^1$H-NMR (400 MHz, D6-DMSO): δ=1.20 (t, 6H), 2.95 (q, 4H), 3.49 (br. s, 1H). MS (ESpos): 122.2 [M+H]$^+$.

Table of the synthesized sulphoximines either by method E or F

| Structure | Synthesis by method | MS: |
|---|---|---|
| diphenyl sulphoximine | F | 218.4 [M + H]$^+$ |
| ethyl methyl sulphoximine | F | 150.2 [M + H]$^+$ |
| cyclohexyl methyl sulphoximine | F | 146 [M – 15] |
| cyclic sulphoximine (tetrahydrothiophene) | F | 119.1 [M$^+$] |
| phenyl ethyl sulphoximine | E | 170 [M + H]$^+$ |
| 2-fluorophenyl methyl sulphoximine | E | 174 [M + H]$^+$ |
| 4-fluorophenyl methyl sulphoximine | E | 174 [M + H]$^+$ |
| 4-chlorophenyl methyl sulphoximine | E | 190 [M + H]$^+$ |
| 4-methylphenyl methyl sulphoximine | E | 170 [M + H]$^+$ |
| 3-methylphenyl methyl sulphoximine | E | 170 [M + H]$^+$ |
| 4-methoxyphenyl methyl sulphoximine | E | 186 [M + H]$^+$ |
| 4-isopropylphenyl methyl sulphoximine | E | 198 [M + H]$^+$ |
| 2,4-dimethylphenyl methyl sulphoximine | E | 184.0 [M + H]$^+$ |
| 2-naphthyl methyl sulphoximine | E | 206.0 [M + H]$^+$ |

| Structure | Synthesis by method | MS: |
|---|---|---|
| (acetamido phenyl sulfoximine) | E | 213.0 [M + H]+ |
| (tert-butyl methyl sulfoximine) | F | 136 [M + H]+ |
| (naphthyl methyl sulfoximine) | E | 206 [M + H]+ |
| (thiomorpholine S-oxide imine) | E | 136 [M + H]+ |

Preparation of Compounds of the (II) Type

Method A: Note: all Compounds Prepared According to Method H Result as Hydrochlorides Intermediate 3: Preparation of 3-(6-bromoquinolin-4-ylamino)phenol

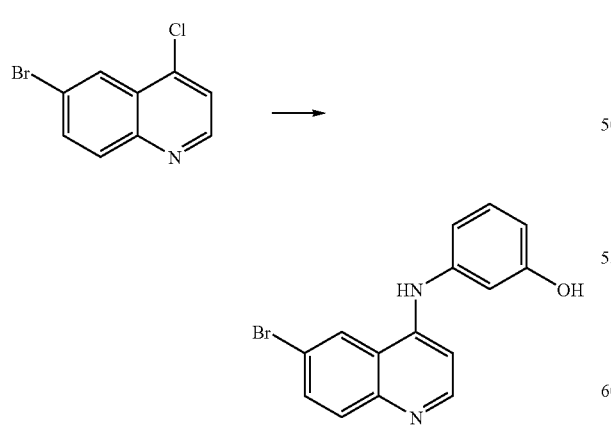

66 mg (0.54 mmol) of 3-aminophenol are added to a suspension of 100 mg (0.41 mmol) of 6-bromo-4-chloroquinoline in 2.7 ml of isopropanol. The resulting mixture is refluxed for 12 h.

The precipitate is filtered off and washed with methyl tert-butyl ether. 119 mg (0.38 mmol, 91%) of the desired product are obtained.

¹H-NMR (300 MHz, D6-DMSO): δ=6.82-6.92 (m, 4H); 7.36 (t, 1H); 8.06 (d, 1H); 8.18 (dd, 1H); 8.53 (d, 1H); 9.12 (d, 1H); 10.01 (s, 1H); 10.96 (s, 1H). MS (ES): 314.

Intermediate 4: Preparation of 3-(6-bromoquinolin-4-ylamino)-4-methyl-phenol

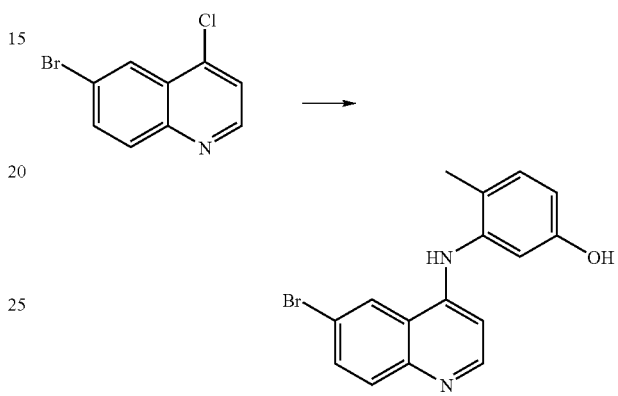

The reaction takes place as described in method A. 97 mg (0.28 mmol, 72%) of the desired product are obtained.

¹H-NMR (300 MHz, D6-DMSO): δ=2.11 (s, 3H); 6.25 (d, 1H); 6.80 (dd, 1H); 6.87 (d, 1H); 7.14 (d, 1H); 8.04 (d, 1H); 8.16 (d, 1H); 8.45 (d, 1H); 9.11 (s, 1H), 9.84 (s, 1H); 10.72 (s, 1H). MS (ES): 328.

Intermediate 5: Preparation of 3-(6-bromoquinolin-4-ylamino)-5-methoxy-phenol

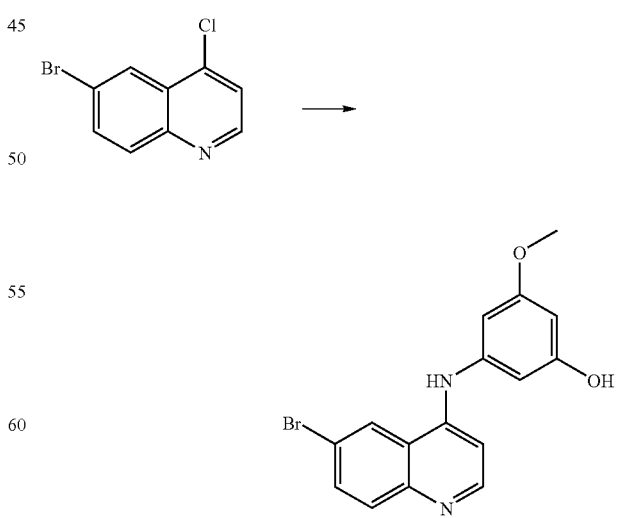

The reaction takes place as described in method A. 128 mg (0.37 mmol, 90%) of the desired product are obtained.

¹H-NMR (300 MHz, D6-DMSO): δ=3.75 (s, 3H); 6.42 (s, 1H); 6.50 (s, 1H); 6.94 (d, 1H); 8.06 (d, 1H); 8.17 (d, 1H); 8.54 (d, 1H); 9.11 (s, 1H); 10.05 (s, 1H); 10.91 (s, 1H). MS (ES): 344.

Intermediate 6: Preparation of (6-bromoquinolin-4-yl)-[3-(tert-butyl-dimethylsilanyloxy)phenyl]amine

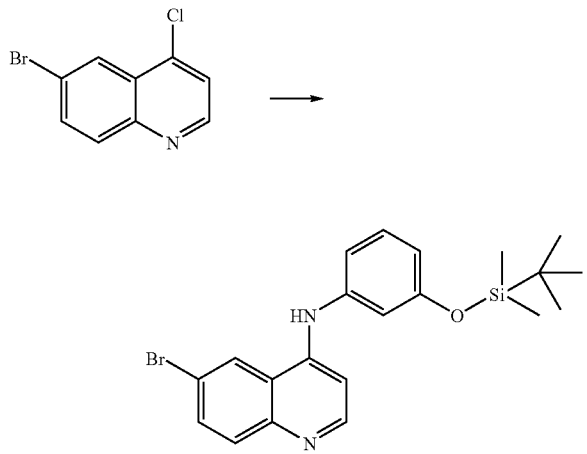

6.26 g (25.8 mmol) of 6-bromo-4-chloroquinoline are reacted by method A with 7.5 g (33.6 mmol) of 3-(tert-butyldimethylsilanyloxy)phenylamine. 8.9 g (20.7 mmol, 80%) of the desired product are obtained.

¹H-NMR (300 MHz, D6-DMSO): δ=0.24 (s, 6H); 0.97 (s, 9H); 6.85 (d, 1H); 6.93 (dd, 1H); 6.98 (t, 2H); 7.46 (t, 1H); 8.09 (d, 1H); 8.18 (dd, 1H); 8.55 (d, 1H); 9.15 (s, 1H); 11.04 (s, 1H). MS (ES): 428.

Intermediate 7: Preparation of (6-bromoquinolin-4-yl)-[5-(tert-butyl-dimethylsilanyloxy)-2-methylphenyl]amine

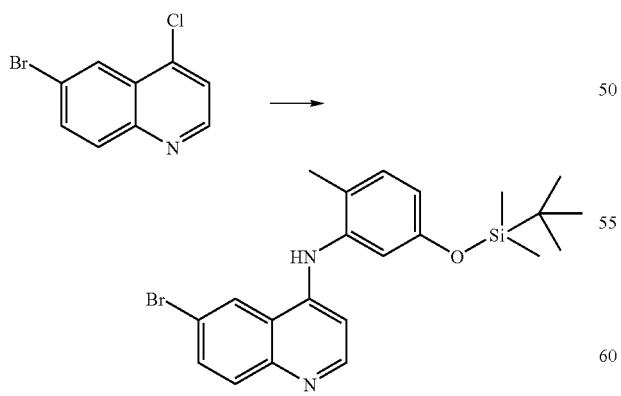

5.52 g (22.8 mmol) of 6-bromo-4-chloroquinoline are reacted by method A with 7.04 g (29.7 mmol) of 4-amino-3-(tert-butyldimethylsilanyloxy)-2-methyl-phenylamine. 9.22 g (20.8 mmol, 91%) of the desired product are obtained.

¹H-NMR (300 MHz, D6-DMSO): δ=0.24 (s, 6H); 0.99 (s, 9H); 2.13 (s, 3H); 6.10 (d, 1H); 6.82 (dd, 1H); 6.91 (d, 1H); 7.17 (d, 1H); 7.85 (d, 1H); 7.91 (dd, 1H); 8.39 (d, 1H); 8.81 (s, 1H). MS (ES): 443.

Intermediate 8: Preparation of (6-bromoquinolin-4-yl)-[5-(tert-butyl-dimethylsilanyloxy)-3-methoxyphenyl]amine

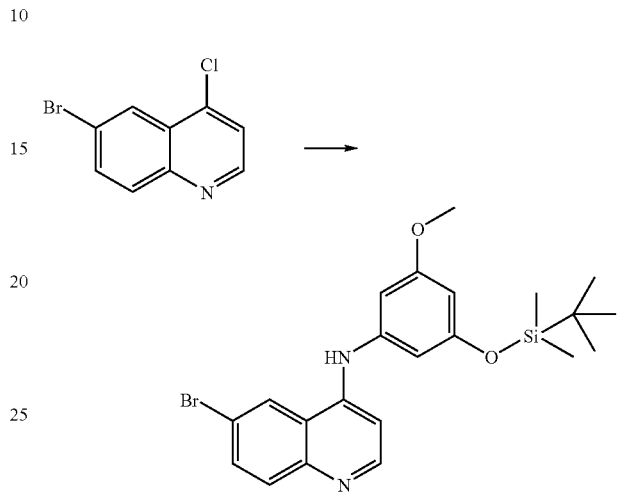

3.68 g (15.2 mmol) of 6-bromo-4-chloroquinoline are reacted by method A with 5.0 g (19.7 mmol) of 4-amino-3-(tert-butyldimethylsilanyloxy)-3-methoxyphenylamine. 6.88 g (14.9 mmol, 76%) of the desired product are obtained.

¹H-NMR (300 MHz, D6-DMSO): δ=0.18 (s, 6H); 0.92 (s, 9H); 3.70 (s, 3H); 6.13 (t, 1H); 6.40 (t, 1H); 6.52 (t, 1H); 7.03 (d, 1H); 7.78 (s, 2H); 8.47 (d, 1H); 8.57 (s, 1H); 8.94 (s, 1H). MS (ES): 459.

Intermediate 9: Preparation of 3-(6-bromoquinolin-4-ylamino)-4-chloro-phenol hydrochloride

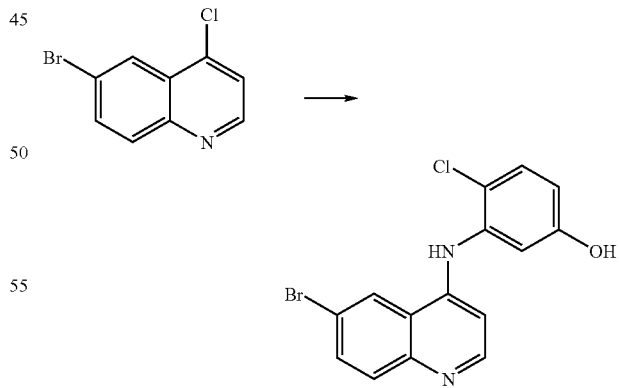

500 mg (2.06 mmol) of 6-bromo-4-chloroquinoline in 20 ml acetonitrile are mixed with 325 mg (2.27 mmol) of 3-amino-4-chlorophenol and 0.5 ml of 1 M HCl solution in dioxane and heated under reflux for 3 days. The crystals which have separated out are filtered off with suction and dried under high vacuum. 700 mg (70%) of the title compound are obtained as hydrochloride.

$^1$H-NMR (400 MHz, D6-DMSO): δ=6.40 (d, 1H), 6.95 (d, 1H), 6.96 (s, 1H), 7.52 (d, 1H), 8.00 (d, 1H), 8.19 (d, 1H), 8.56 (d, 1H), 9.04 (s, 1H), ca. 10.3 (br. s, 1H), 10.87 (br. s, 1H), ca. 14.57 (br. s, 1H). MS (ESpos): 349 and 351 [M+H]$^+$.

Preparation of Compounds of the (XI) Type

Intermediate 10: Preparation of 4-chloro-6-{[methyl(oxido)phenyl-λ$^4$-sulphanylidene]amino}quinoline

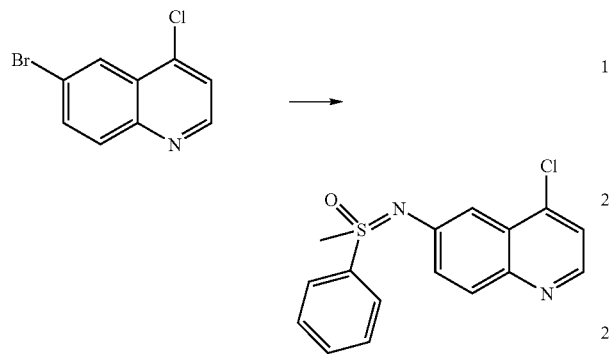

960 mg (6.19 mmol) of R-(−)—S-methyl-S-phenylsulphoximine, 142 mg (0.16 mmol) of tris(dibenzylideneacetone)dipalladium, 215 mg (0.37 mmol) of 9,9-dimethyl-4,5-bis(diphenylphosphino)xanthene and 543 mg (7.42 mmol) of sodium tert-butoxide are added to 1.5 g (6.19 mmol) of 6-bromo-4-chloroquinoline in 64 ml of 1,4-dioxane under argon. After stirring at 110° C. overnight, the mixture is cooled and filtered through Celite. The solvent is removed from the filtrate under reduced pressure, and the residue is purified by chromatography on a silica gel column (mobile phase: dichloromethane:methanol 100:1). 1.43 g (73%) of the title compound are obtained.

$^1$H-NMR (500 MHz, D6-DMSO): δ=3.52 (s, 3H), 7.4-7.46 (m, 2H), 7.53-7.7 (m, 4H), 7.86 (d, 1H), 8.0 (d, 2H), 8.56 (d, 1H). MS (ESpos): 317.1 [M+H]$^+$.

Intermediate 11: Preparation of 4-chloro-6-{[dimethyl(oxido)-λ$^4$-sulphanylidene]amino}quinoline

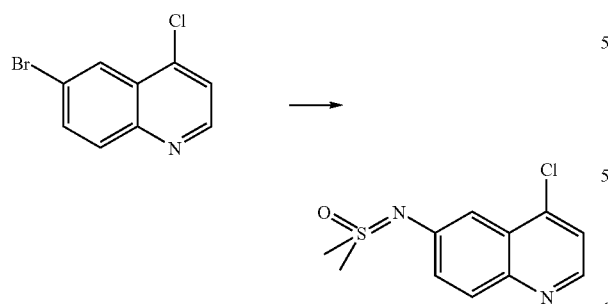

768 mg (8.25 mmol) of S,S-dimethylsulphoximine, 189 mg (0.21 mmol) of tris(dibenzylideneacetone)dipalladium, 286 mg (0.5 mmol) of 9,9-dimethyl-4,5-bis(diphenylphosphino)xanthene and 724 mg (9.9 mmol) of sodium tert-butoxide are added to 2 g (8.25 mmol) of 6-bromo-4-chloroquinoline in 85 ml of 1,4-dioxane under argon. After stirring at 110° C. overnight, the mixture is cooled and filtered through Celite. The filtrate is washed with water and sat. NaCl solution, and the org. phase is dried and concentrated under reduced pressure. The residue is purified by chromatography on a silica gel column (mobile phase: dichloromethane:methanol 100:2). 1.41 g (67%) of the title compound are obtained.

$^1$H-NMR (400 MHz, D6-DMSO): δ=3.35 (s, 6H), 7.47 (dd, 1H), 7.60 (d, 1H), 7.65 (d, 1H), 7.92 (d, 1H), 8.60 (d, 1H). MS (ESpos): 255.0 [M+H]$^+$.

Intermediate 12: Preparation of N'-(4-bromo-2-cyanophenyl)-N,N-dimethyl-formamidine

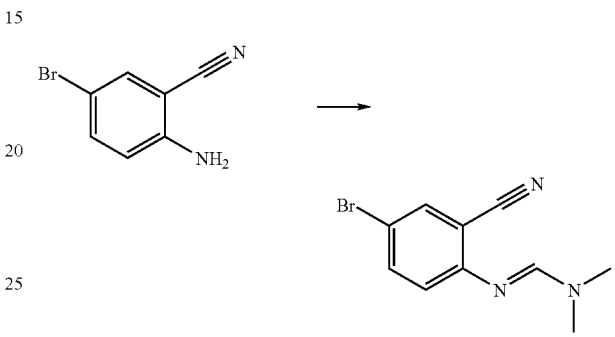

59 g (300 mmol) of 2-cyano-4-bromoaniline are suspended in 35 ml of dimethylformamide dimethyl acetal (780 mmol) and heated under reflux for 1.5 h. The resulting mixture is cooled and then 300 ml of hexane are added. The resulting solid is filtered off and washed with hexane. 64.5 g (85%) of the desired product are obtained.

$^1$H-NMR (300 MHz, CDCl$_3$): δ=3.07 (s, 6H); 6.82 (d, 1H); 7.47 (dd, 1H); 7.56 (s, 1H); 7.60 (d, 1H).

Intermediate 13: Preparation of 3-(6-bromoquinazolin-4-ylamino)-4-methylphenol

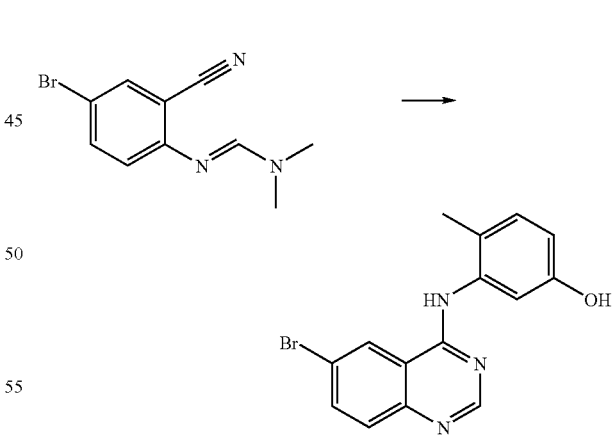

6.0 g (23.9 mmol) of N'-(4-bromo-2-cyanophenyl)-N,N-dimethylformamidine and 3.24 g (26.3 mmol) of 2-amino-4-hydroxytoluene are suspended in 40 ml of acetic acid and heated under reflux for 1 h. The resulting mixture is cooled and then added to 100 ml of water and extracted with ethyl acetate. The combined organic phases are washed with water and sat. aqueous sodium chloride solution and dried over sodium sulphate, and the solvent is evaporated. 8.0 g (100%) of the desired product are obtained.

$^1$H-NMR (300 MHz, D6-DMSO): δ=1.91 (s, 3H); 6.65 (dd, 1H); 6.73 (d, 1H); 7.09 (d, 1H); 7.71 (d, 1H); 7.97 (dd, 1H); 8.45 (s, 1H); 8.77 (s, 1H); 9.68 (s, 1H).

Intermediate 14: Preparation of 5-(6-bromoquinazolin-4-ylamino)-4-fluoro-2-methylphenol

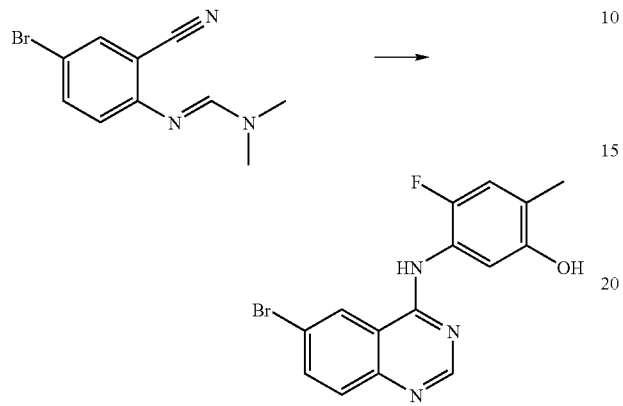

5.0 g (19.9 mmol) of N'-(4-bromo-2-cyanophenyl)-N,N-dimethylformamidine and 3.09 g (21.9 mmol) of 5-amino-4-fluoro-2-methylphenol are suspended in 25 ml of acetic acid and heated under reflux for 1 h. The solid obtained after cooling is filtered off and washed with hexane. 4.02 g (58%) of the desired product are obtained.

$^1$H-NMR (300 MHz, D6-DMSO): δ=2.15 (s, 3H); 6.91 (d, 1H); 7.03 (d, 1H); 7.73 (d, 1H); 7.99 (dd, 1H); 8.50 (s, 1H); 8.77 (d, 1H); 9.41 (s, 1H); 9.78 (s, 1H).

Intermediate 15: Preparation of 3-[(6-bromoquinolin-4-yl)oxy]-4-methylphenol

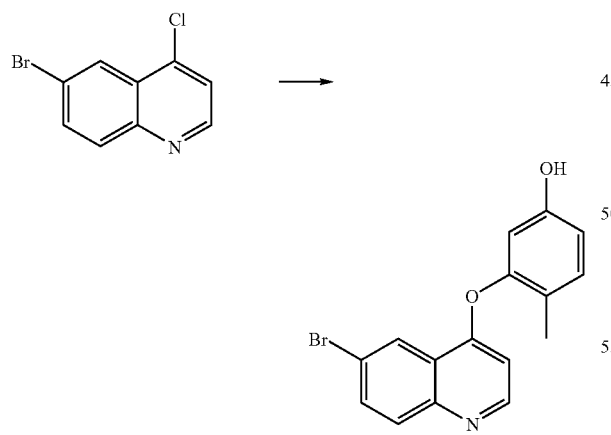

141 mg (0.58 mmol) of 6-bromo-4-chloroquinoline and 150 mg (0.7 mmol) 5-(benzyloxy)-2-methylphenol in 5 ml acetonitrile are mixed with 97 mg (0.7 mmol) of potassium carbonate and heated in the microwave oven to 150° C. for 3 h. The mixture is diluted with water and then extracted with ethyl acetate. The organic layers are washed with brine and dried over sodium sulfate. The solvent is evaporated and the resulting residue is dissolved in 5 ml TFA. 54 mg (0.44 mmol) thioanisole is added and the mixture is stirred over night. The solvent is evaporated, the resulting residue is dissolved in ethyl acetate and washed with sat. NaHCO$_3$ and brine. The organic layers are dried over sodium sulfate, the solvent is evaporated and the resulting residue is purified by preparative HPLC. 90 mg (46%) of the desired product are obtained $^1$H-NMR (400 MHz, D6-DMSO): δ=1.99 (s, 3H), 6.58 (d, 1H), 6.60 (d, 1H), 6.73 (dd, 1H), 7.232 (d, 1H), 8.01 (s, 2H), 8.52 (s, 1H), 8.77 (d, 1H), 9.68 (br, 1H). MS (ESneg): 327.9 and 329.9 [M–H]$^+$.

Preparation of the Final Compounds of the Invention of the (A) Type

Method B

EXAMPLE 1

Preparation of N-(1-methylethyl)-6-[[(S)-methyloxidophenyl-λ$^4$-sulphanylidene]amino]-4-quinazolinamine

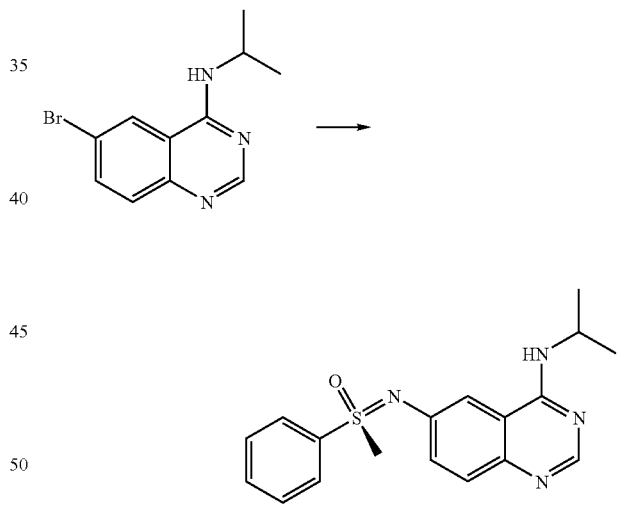

40 mg (0.15 mmol) of 6-bromo-4-isopropylaminoquinazoline, 34 mg (0.22 mmol) of (S)-(+)-S-methyl-S-phenylsulphoximine, 34.9 mg (0.56 mmol) of rac-BINAP, 16.5 mg (0.018 mmol) of tris(dibenzylidenacetone)dipalladium(0) and 28.8 mg (0.3 mmol) of sodium tert-butoxide are stirred in a mixture of 1 ml of dimethylformamide and 2 ml of tetrahydrofuran at 100° C. under a nitrogen atmosphere for 12 h.

The resulting reaction mixture is mixed with 1 ml of water and 3 ml of ethyl acetate. The organic phase is separated off, the solvent is evaporated and the resulting residue is purified by HPLC-MS. 22 mg (0.066 mmol, 44%) of the desired product are obtained.

¹H-NMR (400 MHz, D6-DMSO): δ=1.26 (d, 6H); 3.49 (s, 3H); 4.63 (sextet, 1H); 7.44 (dd, 1H); 7.50 (d, 1H); 7.59-7.71 (m, 3H); 7.93-8.0 (m, 3H); 8.68 (s, 1H); 9.53 (d, 1H). MS (ES): 340.

EXAMPLE 2

Preparation of 6-[(dimethyloxido-λ⁴-sulphanylidene) amino]-N-(1-methylethyl)-4-quinazolinamine

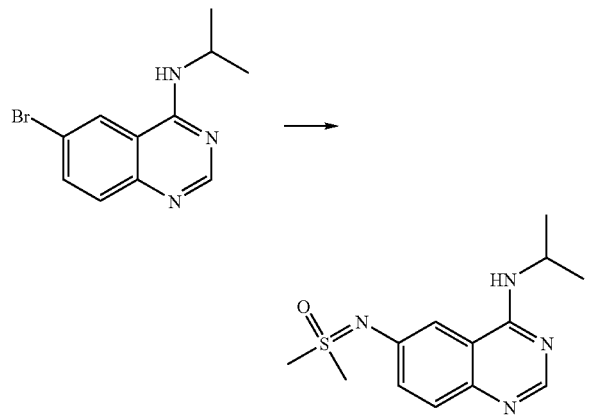

40 mg (0.15 mmol) of 6-bromo-4-chloroquinoline are reacted by method B with 21 mg (0.22 mmol) of S,S-dimethylsulphoximine. 8 mg (0.01 mmol, 18%) of the desired product are obtained.

¹H-NMR (300 MHz, D6-DMSO): δ=1.29 (d, 6H); 3.31 (s, 3H); 4.65 (sextet, 1H); 7.62 (s, 2H); 7.84 (s, 1H); 8.71 (s, 1H); 9.47 (d, 1H). MS (ES): 278.

EXAMPLE 3

Preparation of 4-fluoro-2-methyl-5-[[6-[(R)-(methyloxido-phenyl-λ⁴-sulphanylidene)amino]-4-quinazolinyl]amino]phenol

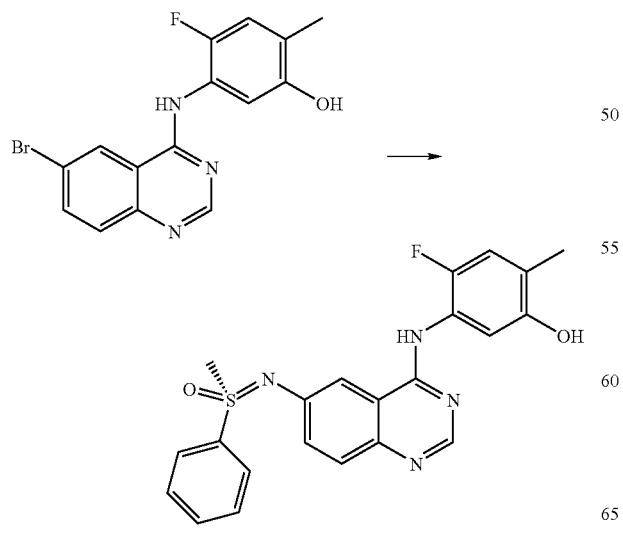

348 mg (1 mmol) of 5-(6-bromoquinazolin-4-ylamino)-4-fluoro-2-methyl-phenol are reacted by method B with 233 mg (1.5 mmol) of (R)-(−)—S-methyl-S-phenylsulphoximine. 49 mg (12%) of the desired product are obtained.

¹H-NMR (300 MHz, D6-DMSO): δ=2.14 (s, 3H); 3.50 (s, 3H); 6.90 (d, 1H); 7.00 (d, 1H); 7.39 (dd, 1H); 7.51 (d, 1H); 7.60-7.74 (m, 3H); 7.88 (s, 1H); 8.00-8.05 (m, 2H); 8.28 (s, 1H); 9.34 (s, 1H); 9.41 (s, 1H).

EXAMPLE 4

Preparation of 4-fluoro-2-methyl-5-[[6-[(S)-(methyloxido-phenyl-λ⁴-sulphanylidene)amino]-4-quinazolinyl]amino]phenol

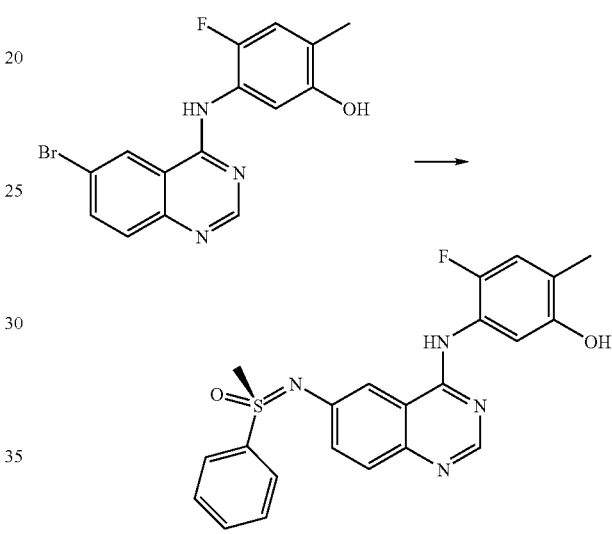

348 mg (1 mmol) of 5-(6-bromoquinazolin-4-ylamino)-4-fluoro-2-methyl-phenol are reacted by method B with 233 mg (1.5 mmol) of (S)-(+)-S-methyl-S-phenylsulphoximine. 53 mg (13%) of the desired product are obtained.

¹H-NMR (300 MHz, D6-DMSO): δ=2.14 (s, 3H); 3.50 (s, 3H); 6.90 (d, 1H); 7.00 (d, 1H); 7.39 (dd, 1H); 7.51 (d, 1H); 7.60-7.74 (m, 3H); 7.88 (s, 1H); 8.00-8.05 (m, 2H); 8.28 (s, 1H); 9.34 (s, 1H); 9.41 (s, 1H).

EXAMPLE 5

Preparation of 5-[[6-[(dimethyloxido-λ⁴-sulphanylidene)amino]-4-quinazolinyl]amino]-4-fluoro-2-methylphenol

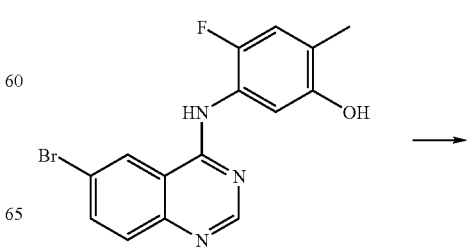

-continued

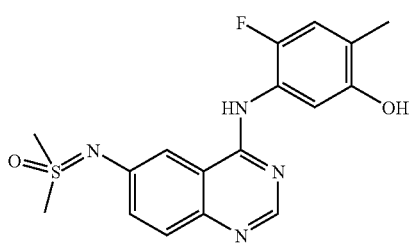

348 mg (1 mmol) of 5-(6-bromoquinazolin-4-ylamino)-4-fluoro-2-methyl-phenol are reacted by method B with 140 mg (1.5 mmol) of S,S-dimethyl-sulphoximine. 126 mg (35%) of the desired product are obtained.

$^1$H-NMR (300 MHz, D6-DMSO): δ=2.15 (s, 3H); 3.35 (s, 6H); 6.90 (d, 1H); 7.00 (d, 1H); 7.46 (dd, 1H); 7.63 (d, 1H); 7.74 (d, 1H); 8.30 (s, 1H); 9.35 (s, 1H); 9.46 (s, 1H).

EXAMPLE 6

Preparation of 4-methyl-3-[[6-[(R)-(methyloxidophenyl-λ$^4$-sulphanylidene)amino]-4-quinazolinyl]amino]phenol

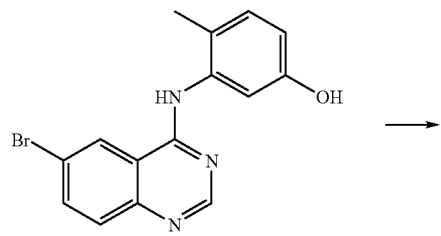

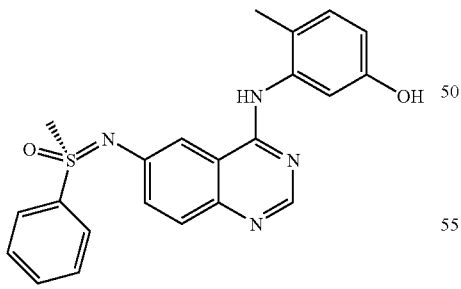

330 mg (1 mmol) of 5-(6-bromoquinazolin-4-ylamino)-4-methyl-phenol are reacted by method B with 233 mg (1.5 mmol) of (R)-(−)—S-methyl-S-phenylsulphoximine. 66 mg (16%) of the desired product are obtained.

$^1$H-NMR (300 MHz, D6-DMSO): δ=2.03 (s, 3H); 3.50 (s, 3H); 6.62 (d, 1H); 6.67 (d, 1H); 7.06 (d, 1H); 7.39 (dd, 1H); 7.50 (dd, 1H); 7.62-7.71 (m, 3H); 7.89 (d, 1H); 8.01-8.07 (m, 2H); 8.23 (s, 1H); 9.24 (s, 1H); 9.28 (s, 1H).

EXAMPLE 7

Preparation of 4-methyl-3-[[6-[(S)-(methyloxidophenyl-λ$^4$-sulphanylidene)amino]-4-quinazolinyl]amino]phenol

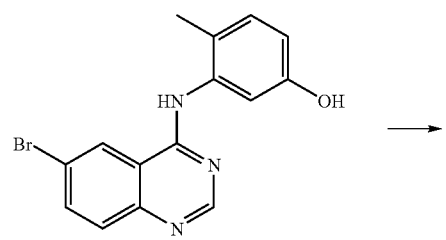

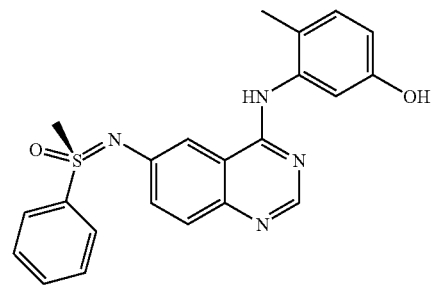

330 mg (1 mmol) of 5-(6-bromoquinazolin-4-ylamino)-4-methyl-phenol are reacted by method B with 233 mg (1.5 mmol) of (S)-(+)-S-methyl-S-phenylsulphoximine. 65 mg (16%) of the desired product are obtained.

$^1$H-NMR (300 MHz, D6-DMSO): δ=2.03 (s, 3H); 3.50 (s, 3H); 6.62 (d, 1H); 6.67 (d, 1H); 7.06 (d, 1H); 7.39 (dd, 1H); 7.50 (dd, 1H); 7.62-7.71 (m, 3H); 7.89 (d, 1H); 8.01-8.07 (m, 2H); 8.23 (s, 1H); 9.24 (s, 1H); 9.28 (s, 1H).

EXAMPLE 8

Preparation of 3-[[6-[(dimethyloxido-λ$^4$-sulphanylidene)amino]-4-quinazolinyl]amino]-4-methylphenol

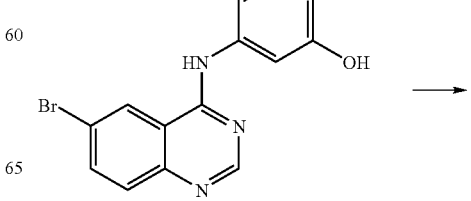

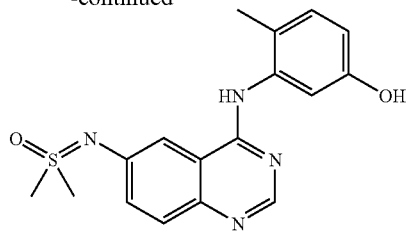

330 mg (1 mmol) of 5-(6-bromoquinazolin-4-ylamino)-4-methyl-phenol are reacted by method B with 140 mg (1.5 mmol) of S,S-dimethyl-sulphoximine. 64 mg (19%) of the desired product are obtained.

$^1$H-NMR (300 MHz, D6-DMSO): δ=2.05 (s, 3H); 3.33 (s, 6H); 6.62 (dd, 1H); 6.75 (d, 1H); 7.07 (d, 1H); 7.46 (dd, 1H); 7.62 (d, 1H); 7.79 (d, 1H); 8.26 (s, 1H); 9.25 (s, 1H); 9.36 (s, 1H).

Method C

EXAMPLE 9

Preparation of 4-methyl-3-[[6-[[(R)-methyloxidophenyl-λ$^4$-sulphanylidene]amino]-4-quinolinyl]amino]phenol

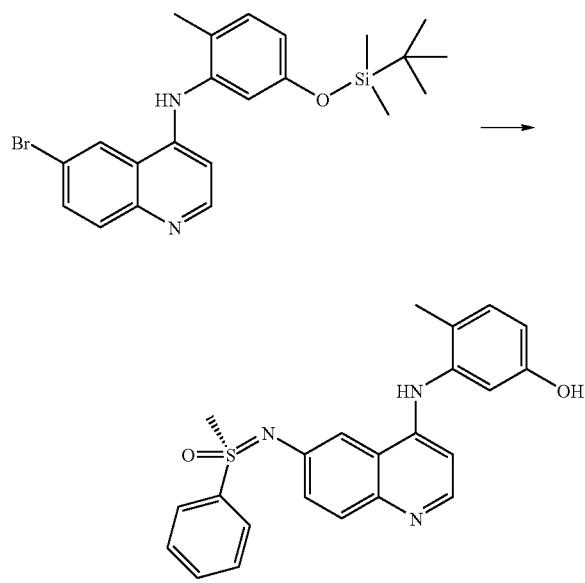

A mixture of 0.5 g (1.13 mmol) of (6-bromoquinolin-4-yl)-[5-(tert-butyl-dimethylsilanyloxy)-2-methylphenyl]amine (intermediate 7), 263 mg (1.69 mmol) (R)-(−)—S-methyl-S-phenylsulphoximine, 39 mg (0.068 mmol) 9,9-dimethyl-4,5-bis(diphenylphosphino)xanthene, 29 mg (0.028 mmol) tris-(dibenzylideneacetone)dipalladium (0) and 130 mg (1.35 mmol) of sodium tert-butoxide is stirred in 14.4 ml of 1,4-dioxane at 110° C. under a nitrogen atmosphere for 12 h.

The reaction mixture is mixed with water and extracted with ethyl acetate. The combined organic phases are washed with saturated aqueous sodium chloride solution, and the solvent is removed by distillation. The crude product is purified by HPLC or flash chromatography. The intermediate obtained in this way is immediately reacted further.

77 mg of the resulting intermediate are taken up in 1 ml of tetrahydrofuran, and 178 μl (0.18 mmol) of a 1 M solution of tetra-n-butylammonium fluoride in THF are added, and the mixture is stirred at room temperature for 3 h. The reaction mixture is poured into saturated aqueous ammonium chloride solution and extracted with ethyl acetate. Solid residues are removed by filtration, the filtrate is dried over sodium sulphate, and the solvent is removed by distillation. 44 mg (8%) of the desired product are obtained.

$^1$H-NMR (400 MHz, D6-DMSO): δ=2.02 (s, 3H); 3.51 (s, 3H); 6.07 (d, 1H); 6.74 (dd, 1H); 6.81 (d, 1H); 7.06 (d, 1H); 7.48 (dd, 1H); 7.59-7.71 (m, 3H); 7.76 (d, 1H); 7.99-8.03 (m, 2H); 8.06 (d, 1H); 8.20 (d, 1H); 9.76 (s, 1H); 10.22 (s, 1H). MS (ES): 403.

EXAMPLE 10

Preparation of 4-methyl-3-[[6-[[(S)-methyloxidophenyl-λ$^4$-sulphanylidene]amino]-4-quinolinyl]amino]phenol

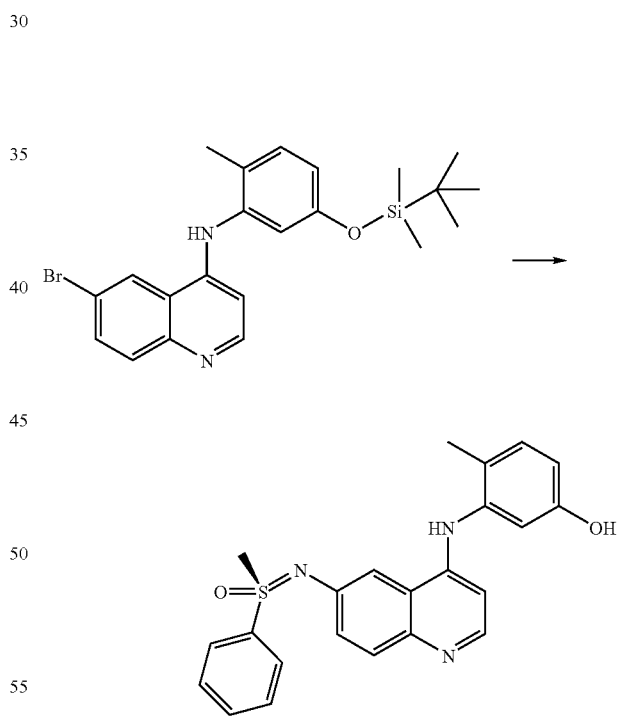

500 mg (1.13 mmol) of (6-bromoquinolin-4-yl)-[5-(tert-butyldimethylsilanyl-oxy)-2-methylphenyl]amine are reacted by method C with 262 mg (1.69 mmol) of (S)-(+)-S-methyl-S-phenylsulphoximine. The resulting crude product is purified by flash chromatography. 52 mg (11%) of the desired product are obtained.

$^1$H-NMR (400 MHz, D6-DMSO): δ=2.04 (s, 3H); 3.47 (s, 3H); 5.87 (d, 1H); 6.69 (dd, 1H); 6.75 (d, 1H); 7.01 (d, 1H);

7.23 (dd, 1H); 7.55 (d, 1H); 7.61-7.69 (m, 3H); 7.68 (d, 1H); 8.04 (dt, 2H); 8.10 (d, 1H); 8.28 (s, 1H); 9.39 (s, 1H). M (ES): 403.

EXAMPLE 11

Preparation of 3-[[6-[[(R)-methyloxidophenyl-λ⁴-sulphanylidene]amino]-4-quinolinyl]amino]phenol

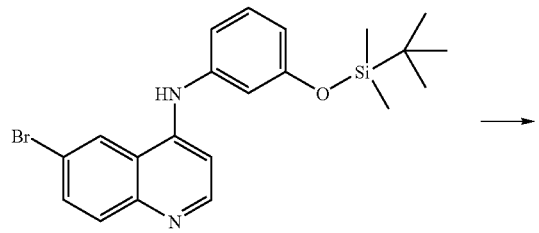

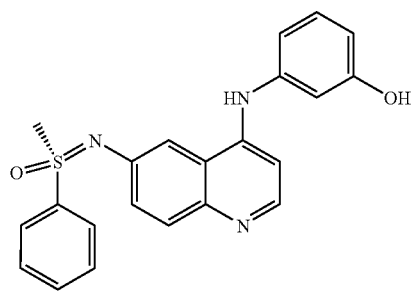

500 mg (1.13 mmol) of (6-bromoquinolin-4-yl)-[3-(tert-butyldimethylsilanyl-oxy)phenyl]-amine are reacted by method C with 262 mg (1.69 mmol) of (R)-(−)-S-methyl-5-phenylsulphoximine. The resulting crude product is purified by flash chromatography. 44 mg (10%) of the desired product are obtained.

¹H-NMR (400 MHz, D6-DMSO): δ=3.46 (s, 3H); 6.50 (d, 1H); 6.75 (dd, 2H); 6.91 (d, 1H); 7.16 (t, 1H); 7.28 (dd, 1H); 7.55-7.70 (m, 4H); 7.81 (d, 1H); 8.01 (dd, 1H); 8.28 (d, 1H); 8.64 (s, 1H); 9.46 (s, 1H). M (ES): 389.

EXAMPLE 12

Preparation of 3-[[6-[[(S)-methyloxidophenyl-λ⁴-sulphanylidene]amino]-4-quinolinyl]amino]phenol

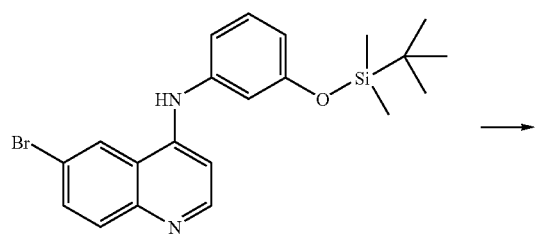

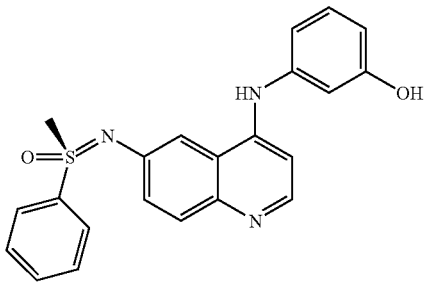

500 mg (1.16 mmol) of (6-bromoquinolin-4-yl)-[3-(tert-butyldimethylsilanyl-oxy)phenyl]amine are reacted by method C with 271 mg (1.75 mmol) of (S)-(+)-S-methyl-S-phenylsulphoximine. The resulting crude product is purified by flash chromatography.

¹H-NMR (400 MHz, D6-DMSO): δ=3.46 (s, 3H); 6.50 (d, 1H); 6.75 (dd, 2H); 6.91 (d, 1H); 7.16 (t, 1H); 7.28 (dd, 1H); 7.55-7.70 (m, 4H); 7.81 (d, 1H); 8.01 (dd, 1H); 8.28 (d, 1H); 8.64 (s, 1H); 9.46 (s, 1H). M (ES): 389.

EXAMPLE 13

Preparation of 3-[[6-[(dimethyloxido-λ⁴-sulphanylidene)-amino]-4-quinolinyl]amino]-phenol

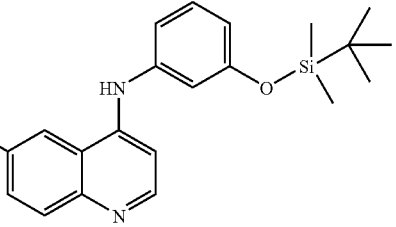

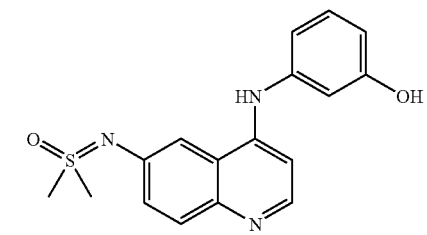

500 mg (1.16 mmol) of (6-bromoquinolin-4-yl)-[3-(tert-butyldimethylsilanyl-oxy)phenyl]amine are reacted by method C with 163 mg (1.75 mmol) of S,S-dimethylsulphoximine. The resulting crude product is purified by HPLC. 5 mg (0.001 mmol, 1%) of the desired product are obtained.

¹H-NMR (400 MHz, D6-DMSO): δ=3.35 (s, 6H); 6.72 (d, 1H); 6.75-6.80 (m, 2H); 6.82 (d, 1H); 7.30 (d, 1H); 7.32 (d, 1H); 7.60 (dd, 1H); 7.81 (d, 1H); 7.91 (d, 1H); 8.33 (d, 1H).

EXAMPLE 14

Preparation of 3-methoxy-5-[[6-[[(R)-methyloxidophenyl-4-sulphanylidene]amino]-4-quinolinyl]amino]phenol

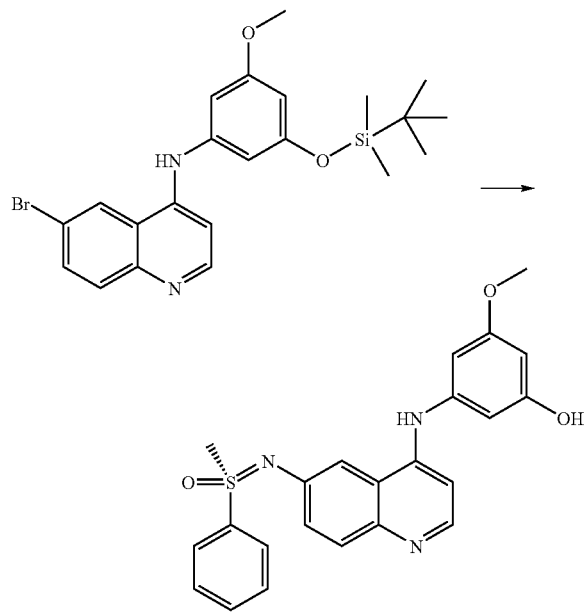

1.0 g (2.18 mmol) of (6-bromoquinolin-4-yl)-[3-(tert-butyldimethylsilanyloxy)-3-methoxyphenyl]amine are reacted by method C with 507 mg (3.265 mmol) of (R)-(−)—S-methyl-S-phenylsulphoximine. The resulting crude product is purified by flash chromatography. 271 mg (0.6 mmol, 33%) of the desired product are obtained.

$^1$H-NMR (400 MHz, D6-DMSO): δ=3.47 (s, 3H); 3.71 (s, 3H); 6.10 (t, 1H); 6.36 (t, 1H); 6.39 (t, 1H); 6.97 (d, 1H); 7.30 (dd, 1H); 7.59-7.69 (m, 4H); 7.81 (d, 1H); 8.01 (dt, 2H); 8.30 (d, 1H); 8.72 (s, 1H); 9.50 (s, 1H). M (ES): 419.

EXAMPLE 15

Preparation of 3-methoxy-5-[[6-[[(S)-methyloxidophenyl-λ$^4$-sulphanylidene]amino]-4-quinolinyl]amino]phenol

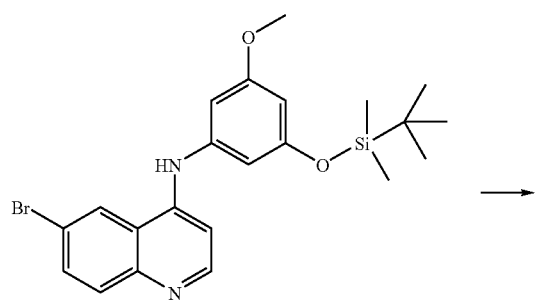

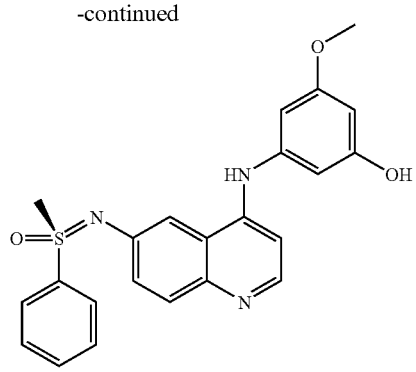

500 mg (1.09 mmol) of (6-bromoquinolin-4-yl)-[3-(tert-butyldimethylsilanyl-oxy)-3-methoxyphenyl]amine are reacted by method C with 253 mg (1.63 mmol) of (S)-(+)-S-methyl-S-phenylsulphoximine. The resulting crude product is purified by flash chromatography. 174 mg (0.34 mmol, 31%) of the desired product are obtained.

$^1$H-NMR (400 MHz, D6-DMSO): δ=3.42 (s, 3H); 3.66 (s, 3H); 6.05 (t, 1H); 6.31 (t, 1H); 6.34 (t, 1H); 6.93 (d, 1H); 7.26 (dd, 1H); 7.55-7.65 (m, 4H); 7.76 (d, 1H); 7.95 (dt, 2H); 8.25 (d, 1H); 8.62 (s, 1H); 9.45 (s, 1H). M (ES): 419.

EXAMPLE 16

Preparation of 3-[[6-[(dimethyloxido-λ$^4$-sulphanylidene)-amino]-4-quinolinyl]amino]-5-methoxyphenol

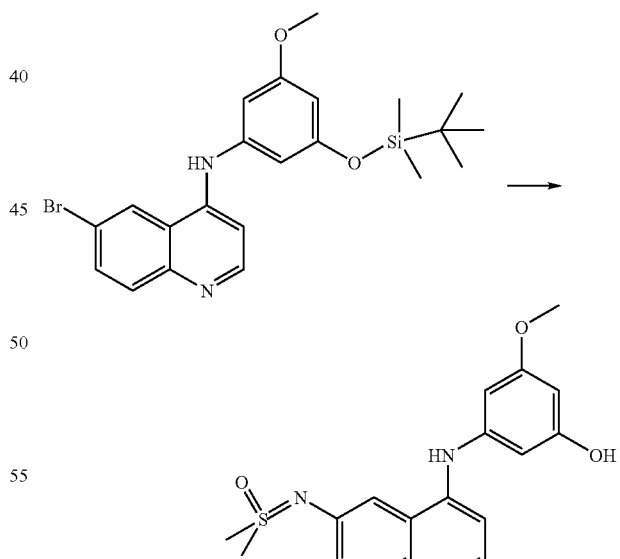

500 mg (1.09 mmol) of (6-bromoquinolin-4-yl)-[3-(tert-butyldimethylsilanyl-oxy)-3-methoxyphenyl]amine are reacted by method C with 152 mg (1.63 mmol) of S,S-dimethylsulphoximine. The resulting crude product is purified by flash chromatography. 38 mg (0.11 mmol, 10%) of the desired product are obtained.

¹H-NMR (400 MHz, D6-DMSO): δ=3.26 (s, 6H); 3.65 (s, 3H); 6.04 (t, 1H); 6.30 (t, 1H); 6.33 (t, 1H); 6.94 (d, 1H); 7.32 (dd, 1H); 7.62 (d, 1H); 7.68 (d, 1H); 8.28 (d, 1H); 8.57 (s, 1H); 9.46 (s, 1H). M (ES): 359.

Method D

EXAMPLE 17

Preparation of 3-methoxy-5-[(6-{[oxido(diphenyl)-λ⁴-sulphanylidene]amino}quinolin-4-yl)amino]phenol

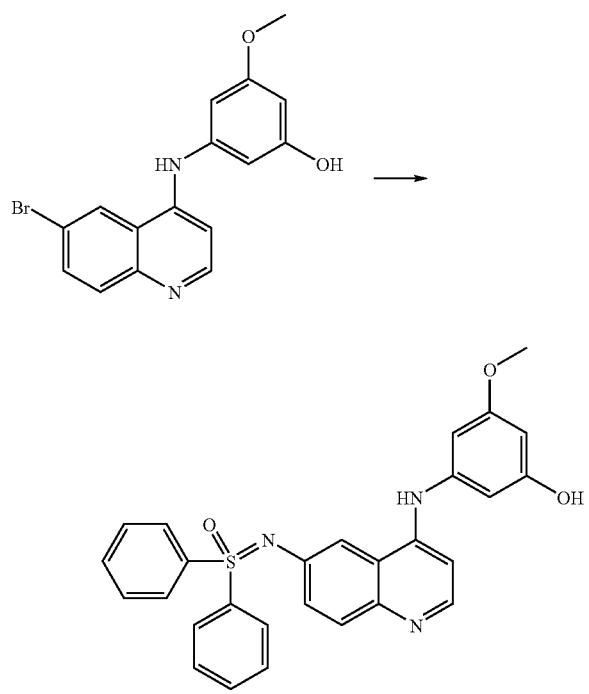

28.5 mg (0.131 mmol) of S,S-diphenylsulphoximine, 9.0 mg (0.010 mmol) of tris(dibenzylideneacetone)dipalladium, 4.5 mg (7.8 μmol) of 9,9-dimethyl-4,5-bis(diphenylphosphino)xanthene and 21.0 mg (0.288 mmol) of sodium tert-butoxide are added to 50.0 mg (0.131 mmol) of 3-[(6-bromoquinolin-4-yl)amino]-5-methoxyphenol hydrochloride (intermediate 5) in 1.5 ml of 1,4-dioxane under argon. After stirring at 110° C. overnight, the mixture is cooled and filtered through Celite. The solvent is removed from the filtrate under reduced pressure, and the residue is purified by chromatography on a silica gel column (mobile phase: dichloromethane:methanol 100:5). 30.7 mg (49%) of the title compound are obtained.

¹H-NMR (400 MHz, D6-DMSO): δ=3.71 (s, 3H), 6.08-6.11 (m, 1H), 6.37-6.41 (m, 2H), 6.99 (d, 1H), 7.43 (dd, 1H), 7.58-7.66 (m, 7H), 8.02 (d, 1H), 8.09-8.13 (m, 4H), 8.32 (d, 1H), 8.75 (br. s, 1H), 9.50 (s, 1H). MS (ESpos): 482.2 [M+H]⁺.

EXAMPLE 18

Preparation of 3-[(6-{[dimethyl(oxido)-λ⁴-sulphanyliden]amino}quinolin-4-yl)amino]-4-methylphenol

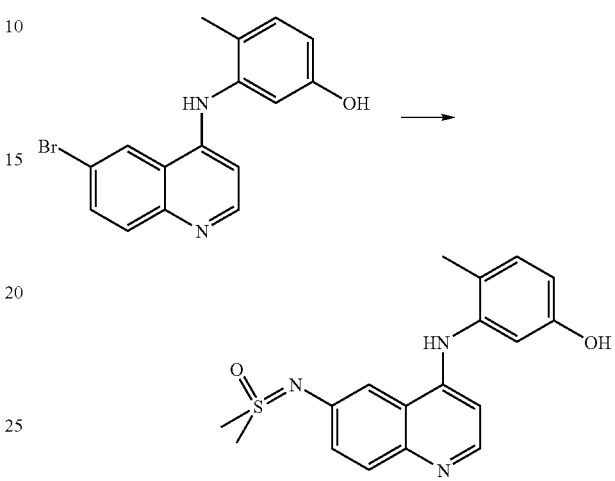

The title compound is prepared starting from 3-(6-bromoquinolin-4-ylamino)-4-methylphenol (intermediate 4) and S,S-dimethylsulphoximine in analogy to the synthesis of the compound of Example 17 (method D).

¹H-NMR (400 MHz, D6-DMSO): δ=2.02 (s, 3H), 6.07 (d, 1H), 6.62-6.66 (m, 2H), 7.13 (d, 1H), 7.36 (dd, 1H), 7.71 (d, 1H), 7.73 (d, 1H), 8.20 (d, 1H), 8.60 (br.s, 1H), 9.34 (s, 1H), solvent signal superimposed on S—(CH₃)₂ signal. MS (ESpos): 342.2 [M+H]⁺.

EXAMPLE 19

Preparation of 4-chloro-3-[(6-{[dimethyl(oxido)-λ⁴-sulphanylidene]amino}quinolin-4-yl)amino]phenol

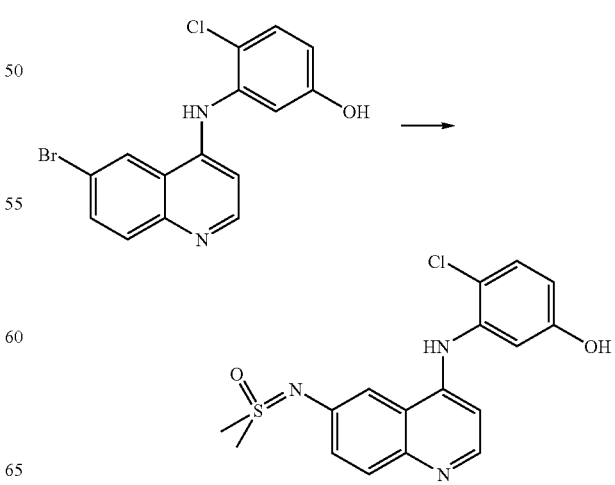

The title compound is prepared starting from 3-(6-bromo-quinolin-4-ylamino)-4-chlorophenol (intermediate 9) and S,S-dimethylsulphoximine in analogy to the synthesis of the compound of Example 17 (method D).

¹H-NMR (400 MHz, D6-DMSO): δ=6.25 (d, 1H), 6.68 (dd, 1H), 6.73 (d, 1H), 7.32-7.36 (m, 2H), 7.64 (d, 1H), 7.72 (d, 1H), 8.27 (d, 1H), 8.45 (s, 1H), ca. 10.0 (br. s, 1H), solvent signal superimposed on S—(CH₃)₂ signal. MS (ESpos): 362.1 [M+H]⁺.

EXAMPLE 20

Preparation of 4-chloro-3-[(6-{[(R)-methyl(oxido)phenyl-λ⁴-sulphanylidene]amino}quinolin-4-yl)amino]phenol

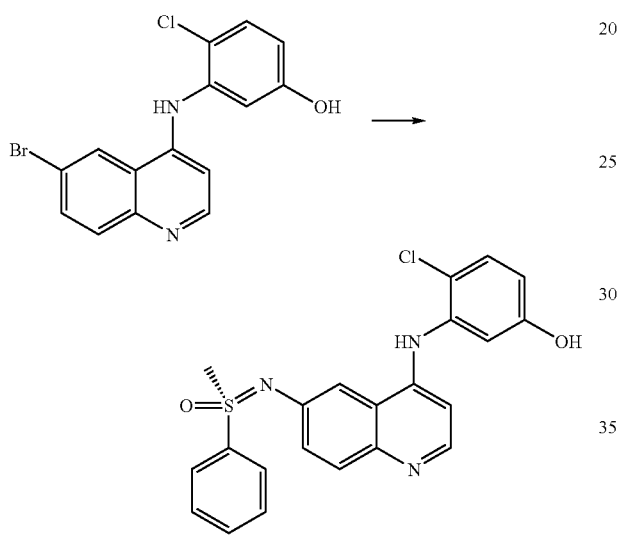

The title compound is prepared starting from 3-(6-bromo-quinolin-4-ylamino)-4-chlorophenol (intermediate 9) and (R)-(−)-S-methyl-S-phenylsulphoximine in analogy to the synthesis of the compound of Example 17 (method D).

¹H-NMR (400 MHz, D6-DMSO): δ=3.46 (s, 3H), 6.24 (d, 1H), 6.68 (dd, 1H), 6.74 (d, 1H), 7.27 (dd, 1H), 7.34 (d, 1H), 7.59-7.69 (m, 4H), 7.73 (d, 1H), 7.99-8.03 (m, 2H), 8.24 (d, 1H), 8.38 (s, 1H), 9.78 (s, 1H). MS (DCI): 424.1 [M+H]⁺.

EXAMPLE 21

Preparation of 4-methyl-3-[(6-{[oxido(diphenyl)-λ⁴-sulphanylidene]amino}quinolin-4-yl)amino]phenol

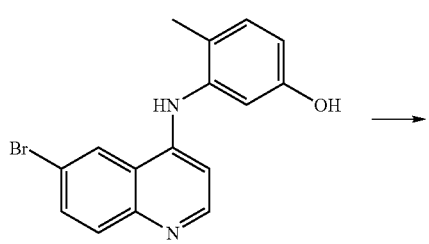

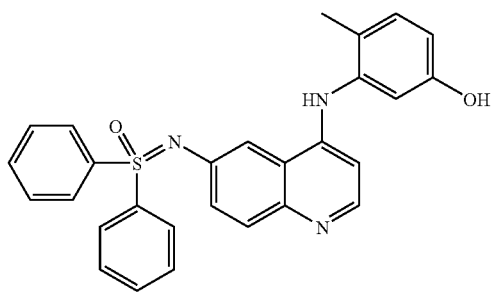

The title compound is prepared starting from 3-(6-bromo-quinolin-4-ylamino)-4-methylphenol (intermediate 4) and S,S-diphenylsulphoximine in analogy to the synthesis of the compound of Example 17 (method D).

¹H-NMR (400 MHz, D6-DMSO): δ=2.01 (s, 3H), 6.05 (d, 1H), 6.62-6.67 (m, 2H), 7.12 (d, 1H), 7.38 (dd, 1H), 7.58-7.67 (m, 7H), 8.03 (d, 1H), 8.08-8.15 (m, 2H), 8.18 (d, 1H), 8.39 (s, 1H), 9.30 (s, 1H). MS (ESpos): 466 [M+H]⁺.

EXAMPLE 22

Preparation of 3-[(6-{[diethyl(oxido)-λ⁴-sulphanylidene]-amino}quinolin-4-yl)amino]-5-methoxyphenol

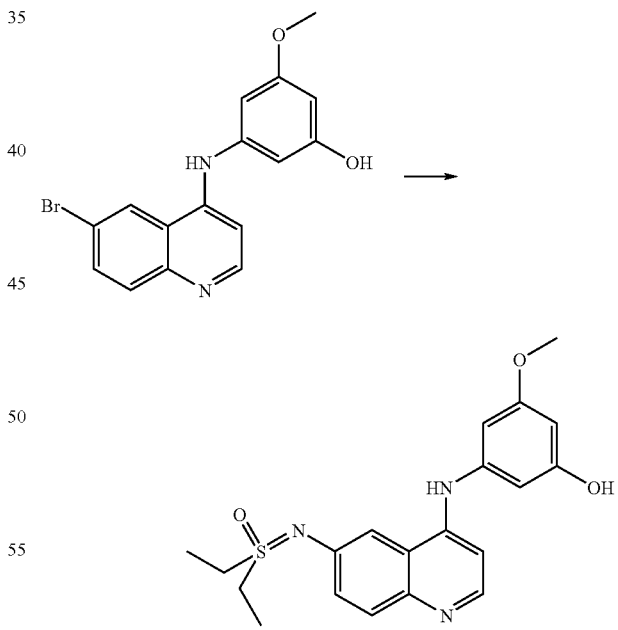

The title compound is prepared starting from 3-(6-bromo-quinolin-4-ylamino)-5-methoxyphenol (intermediate 5) and S,S-diethylsulphoximine in analogy to the synthesis of the compound of Example 17 (method D).

¹H-NMR (400 MHz, D6-DMSO): δ=1.28 (t, 6H), 3.67 (s, 3H), 6.01 (m_c, 1H), 6.24 (m_c, 1H), 6.30 (m_c, 1H), 6.96 (d, 1H), 7.39 (dd, 1H), 7.61-7.82 (m, 2H), 8.28 (d, 1H), 8.49 (s,

1H), solvent signal superimposed on S—(C$\underline{H}_2$)$_2$ and Het-$\underline{H}$ signals. MS (ESpos): 386.3 [M+H]$^+$.

EXAMPLE 23

Preparation of racemic 3-[(6-{[ethyl(methyl)oxido-$\lambda^4$-sulphanylidene]amino}quinolin-4-yl)amino]-5-methoxyphenol

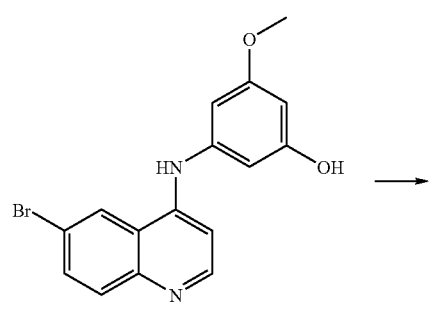

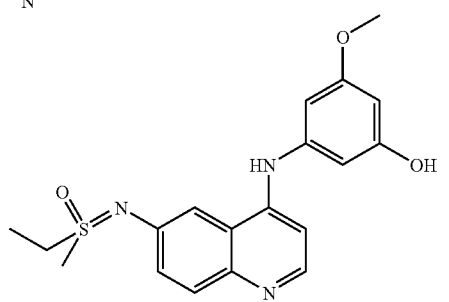

The title compound is prepared starting from 3-(6-bromo-quinolin-4-ylamino)-5-methoxyphenol (intermediate 5) and S-ethyl-S-methylsulphoximine in analogy to the synthesis of the compound of Example 17 (method D).

$^1$H-NMR (400 MHz, D6-DMSO): δ=1.32 (t, 3H), 3.19 (s, 3H), 3.43 (q, 2H), 3.69 (s, 3H), 6.06 (m$_c$, 1H), 6.33 (m$_c$, 1H), 6.35 (m$_c$, 1H), 6.98 (d, 1H), 7.37 (dd, 1H), 7.66 (d, 1H), 7.71 (d, 1H), 8.31 (d, 1H), 8.55 (s, 1H), 9.45 (s, 1H). MS (ESpos): 372.1 [M+H]$^+$.

EXAMPLE 24

Preparation of 3-methoxy-5-[(6-{[oxido(dipropyl)-$\lambda^4$-sulphanylidene]amino}quinolin-4-yl)amino]phenol

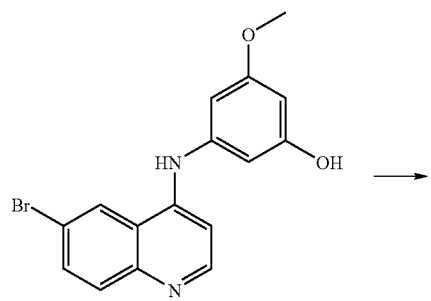

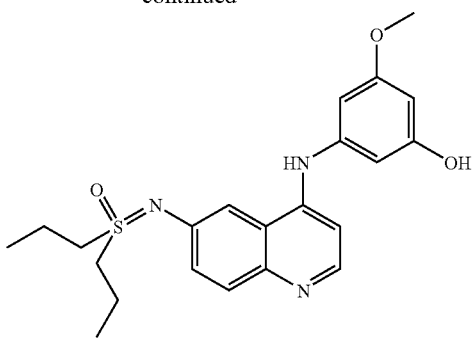

The title compound is prepared starting from 3-(6-bromo-quinolin-4-ylamino)-5-methoxyphenol (intermediate 5) and S,S-dipropylsulphoximine in analogy to the synthesis of the compound of Example 17 (method D).

$^1$H-NMR (400 MHz, D6-DMSO): δ=0.98 (t, 6H), 1.78 (qt, 4H), 3.69 (s, 3H), 6.05 (m$_c$, 1H), 6.33 (m$_c$, 1H), 6.35 (m$_c$, 1H), 6.99 (d, 1H), 7.40 (dd, 1H), 7.66 (d, 1H), 7.70 (d, 1H), 8.31 (d, 1H), 8.54 (s, 1H), 9.46 (br. s, 1H). MS (ESpos): 414.3 [M+H]$^+$.

EXAMPLE 25

Preparation of racemic 3-[(6-{[cyclohexyl(methyl)oxido-$\lambda^4$-sulphanylidene]amino}quinolin-4-yl)amino]-5-methoxyphenol

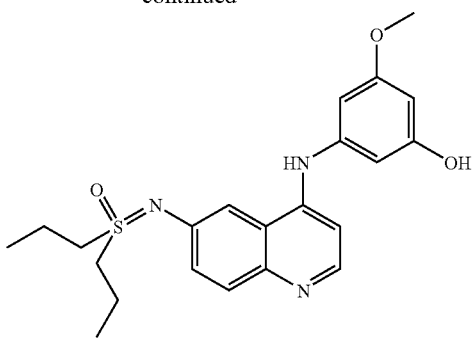

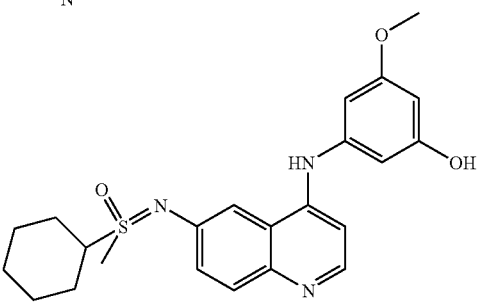

The title compound is prepared starting from 3-(6-bromo-quinolin-4-ylamino)-5-methoxyphenol (intermediate 5) and (S-methylsulphonimidoyl)cyclohexane in analogy to the synthesis of the compound of Example 17 (method D).

$^1$H-NMR (400 MHz, D6-DMSO): δ=1.13-1.40 (m, 4H), 1.45-1.70 (m, 3H), 1.81-1.91 (m, 2H), 2.18-2.27 (m, 2H), 3.11 (s, 3H), 3.69 (s, 3H), 6.05 (m$_c$, 1H), 6.33 (m$_c$, 1H), 6.36

($m_c$, 1H), 6.99 (d, 1H), 7.40 (dd, 1H), 7.67 (d, 1H), 7.70 (d, 1H), 8.31 (d, 1H), 8.55 (s, 1H), 9.44 (s, 1H). MS (ESpos): 426.2 [M+H]$^+$.

EXAMPLE 26

Preparation of 3-methoxy-5-({6-[(1-oxidotetrahydro-1H-1$\lambda^4$-thiophen-1-ylidene)amino]quinolin-4-yl}amino)phenol

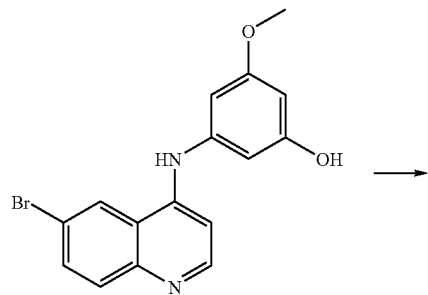

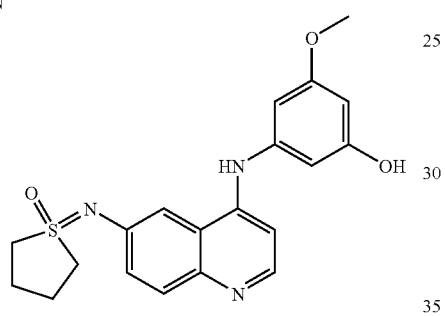

The title compound is prepared starting from 3-(6-bromo-quinolin-4-ylamino)-5-methoxyphenol (intermediate 5) and tetrahydro-1H-1$\lambda^4$-thiophene-1-imine 1-oxide in analogy to the synthesis of the compound of Example 17 (method D).

$^1$H-NMR (400 MHz, D6-DMSO): δ=2.07-2.30 (m, 4H), 3.64 (s, 3H), 5.96 (s, 1H), 6.08 (s, 1H), 6.22 (s, 1H), 6.91 (d, 1H), 7.31 (dd, 1H), 7.64 (d, 1H), 7.69 (d, 1H), 8.24 (d, 1H), 8.42 (s, 1H), solvent signal superimposed on 2×S—CH$_2$ and Het-H signals. MS (ESpos): 384.2 [M+H]$^+$.

EXAMPLE 27

Preparation of racemic 3-[(6-{[ethyl(oxido)phenyl-$\lambda^4$-sulphanylidene]amino}quinolin-4-yl)amino]-5-methoxyphenol

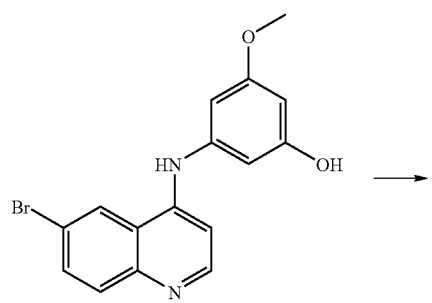

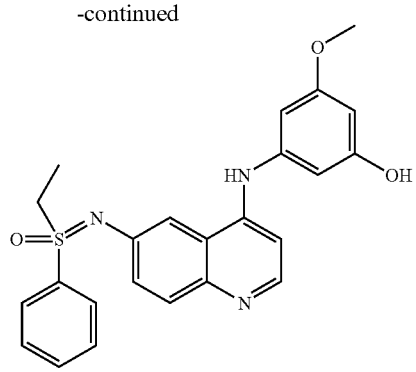

The title compound is prepared starting from 3-(6-bromo-quinolin-4-ylamino)-5-methoxyphenol (intermediate 5) and S-ethyl-S-phenylsulphoximine in analogy to the synthesis of the compound of Example 17 (method D).

$^1$H-NMR (400 MHz, D6-DMSO): δ=1.20 (t, 3H), 3.57 (q, 2H), 3.70 (s, 3H), 6.10 ($m_c$, 12H), 6.35-6.39 (m, 2H), 6.95 (d, 1H), 7.32 (dd, 1H), 7.58-7.71 (m, 4H), 7.84 (d, 1H), 7.92-7.96 (m, 2H), 8.29 (d, 1H), 8.81 (br. s, 1H), 9.50 (s, 1H). MS (ESpos): 434.1 [M+H]$^+$.

EXAMPLE 28

Preparation of racemic 3-[(6-{[(2-fluorophenyl)(methyl)oxido-$\lambda^4$-sulphanylidene]amino}quinolin-4-yl)amino]-5-methoxyphenol

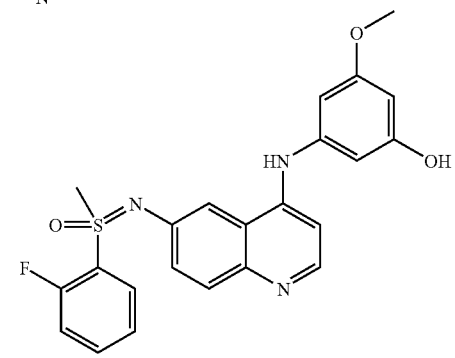

The title compound is prepared starting from 3-(6-bromo-quinolin-4-ylamino)-5-methoxyphenol (intermediate 5) and S-(2-fluorophenyl)-S-methyl-sulphoximine in analogy to the synthesis of the compound of Example 17 (method D).

$^1$H-NMR (400 MHz, D6-DMSO): δ=3.59 (s, 3H), 3.70 (s, 3H), 6.12 ($m_c$, 1H), 6.35-6.38 (m, 2H), 6.94 (d, 1H), 7.31 (dd, 1H), 7.40-7.47 (m, 2H), 7.62 (d, 1H), 7.69-7.76 (m, 1H), 7.80

(d, 1H), 8.00 (ddd, 1H), 8.30 (d, 1H), 8.93 (br. s, 1H), 9.52 (s, 1H). MS (ESpos): 438.2 [M+H]⁺.

EXAMPLE 29

Preparation of racemic 3-[(6-{[(4-fluorophenyl)(methyl)oxido-λ⁴-sulphanylidene]amino}quinolin-4-yl)amino]-5-methoxyphenol

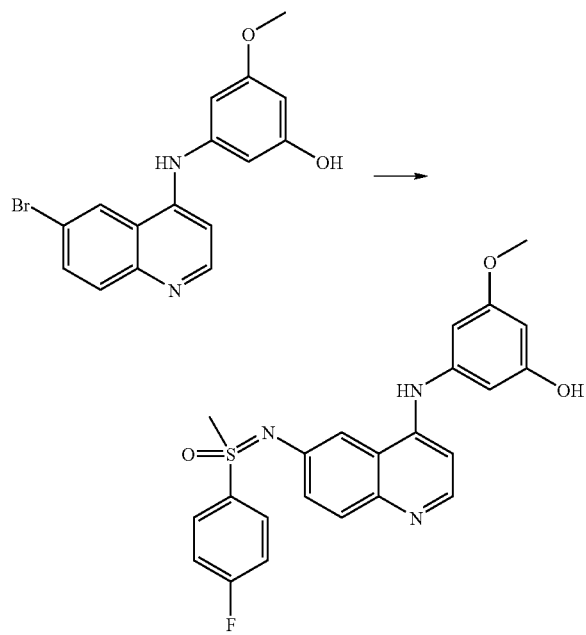

The title compound is prepared starting from 3-(6-bromo-quinolin-4-ylamino)-5-methoxyphenol (intermediate 5) and S-(4-fluorophenyl)-S-methyl-sulphoximine in analogy to the synthesis of the compound of Example 17 (method D).

¹H-NMR (400 MHz, D6-DMSO): δ=3.47 (s, 3H), 3.69 (s, 3H), 6.06 (m_c, 1H), 6.34 (m_c, 1H), 6.36 (m_c, 1H), 6.98 (d, 1H), 7.27 (dd, 1H), 7.43-7.49 (m, 2H), 7.61 (d, 1H), 7.77 (d, 1H), 8.03-8.08 (m, 2H), 8.30 (d, 1H), 8.58 (s, 1H), 9.45 (s, 1H). MS (ESpos): 438.3 [M+H]⁺.

EXAMPLE 30

Preparation of racemic 3-[(6-{[(4-chlorophenyl)(methyl)oxido-λ⁴-sulphanylidene]amino}quinolin-4-yl)amino]-5-methoxyphenol

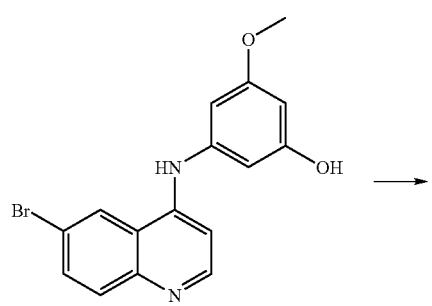

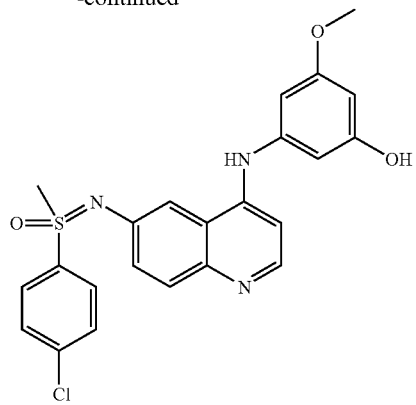

The title compound is prepared starting from 3-(6-bromo-quinolin-4-ylamino)-5-methoxyphenol (intermediate 5) and S-(4-chlorophenyl)-S-methyl-sulphoximine in analogy to the synthesis of the compound of Example 17 (method D).

¹H-NMR (400 MHz, D6-DMSO): δ=3.49 (s, 3H), 3.69 (s, 3H), 6.06. (m_c, 1H), 6.34 (m_c, 1H), 6.36. (m_c, 1H), 6.98 (d, 1H), 7.26 (ddd, 1H), 7.61 (d, 1H), 7.70 (d, 2H), 7.77 (d, 1H), 8.00 (d, 2H), 8.30 (d, 1H), 8.59 (s, 1H), 9.46 (s, 1H). MS (ESpos): 454.2 [M+H]⁺.

EXAMPLE 31

Preparation of racemic 3-[(6-{[(4-methylphenyl)-(methyl)oxido-λ⁴-sulphanylidene]amino}quinolin-4-yl)amino]-5-methoxy-phenol

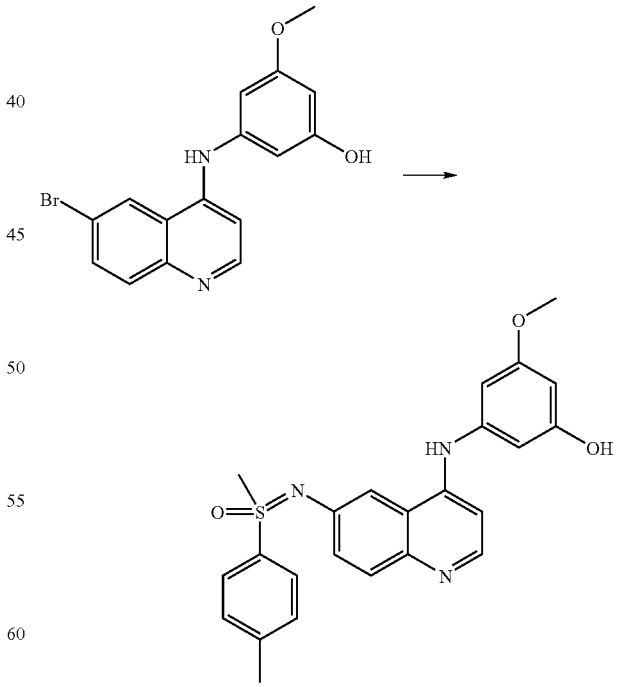

The title compound is prepared starting from 3-(6-bromo-quinolin-4-ylamino)-5-methoxyphenol (intermediate 5) and S-(4-methylphenyl)-S-methyl-sulphoximine in analogy to the synthesis of the compound of Example 17 (method D).

EXAMPLE 32

Preparation of racemic 3-[(6-{[(3-methylphenyl)-(methyl)oxido-λ⁴-sulphanylidene]amino}quinolin-4-yl)amino]-5-methoxy-phenol

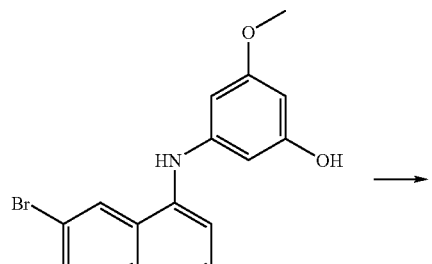

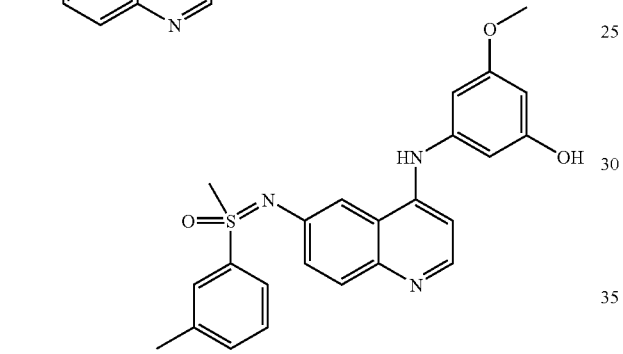

The title compound is prepared starting from 3-(6-bromo-quinolin-4-ylamino)-5-methoxyphenol (intermediate 5) and S-(3-methylphenyl)S-methyl-sulphoximine in analogy to the synthesis of the compound of Example 17 (method D).

¹H-NMR (400 MHz, D6-DMSO): δ=2.39 (s, 3H), 3.46 (s, 3H), 3.71 (s, 3H), 6.15 (m_c, 1H), 6.37-6.39 (m, 2H), 6.93 (d, 1H), 7.35 (dd, 1H), 7.49-7.52 (m, 2H), 7.64 (d, 1H), 7.84-7.87 (m, 2H), 8.31 (d, 1H), 9.08 (br. s, 1H), 9.57 (s, 1H). MS (ESpos): 434.3 [M+H]⁺.

EXAMPLE 33

Preparation of racemic 3-[(6-{[(4-methoxyphenyl)-(methyl)oxido-λ⁴-sulphanylidene]amino}quinolin-4-yl)amino]-5-methoxy-phenol

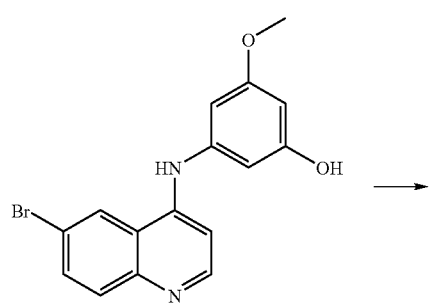

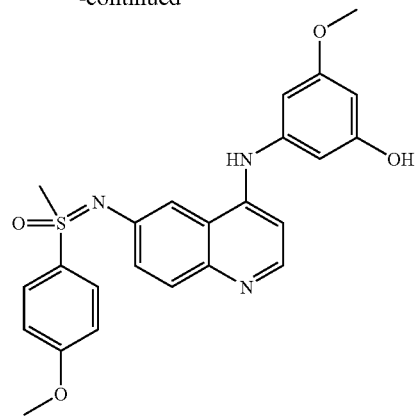

The title compound is prepared starting from 3-(6-bromo-quinolin-4-ylamino)-5-methoxyphenol (intermediate 5) and S-(4-methoxyphenyl)-S-methyl-sulphoximine in analogy to the synthesis of the compound of Example 17 (method D).

¹H-NMR (400 MHz, D6-DMSO): δ=3.70 (s, 3H), 3.81 (s, 3H), 6.08 (m_c, 1H), 6.35 (m_c, 1H), 6.37 (m_c, 1H), 6.97 (d, 1H), 7.13 (d, 2H), 7.28 (dd, 1H), 7.60 (d, 1H), 7.78 (d, 1H), 7.90 (d, 2H), 8.29 (d, 1H), 8.69 (br. s, 1H), 9.47 (s, 1H). MS (ESpos): 450.3 [M+H]⁺.

EXAMPLE 34

Preparation of racemic 3-methoxy-5-{[6-({methyl[4-(1-methylethyl)phenyl]oxido-λ⁴-sulphanylidene}amino)quinolin-4-yl]amino}-phenol

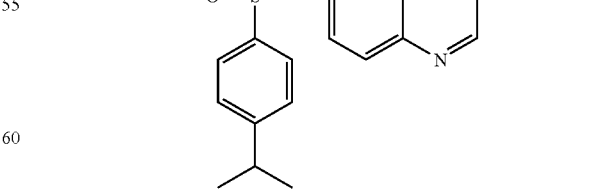

The title compound is prepared starting from 3-(6-bromo-quinolin-4-ylamino)-5-methoxyphenol (intermediate 5) and S-(4-isopropylphenyl)-S-methyl-sulphoximine in analogy to the synthesis of the compound of Example 17 (method D).

¹H-NMR (400 MHz, D6-DMSO): δ=1.18 (d, 3H), 1.19 (d, 3H), 2.96 (qq, 1H), 3.43 (t, 3H), 3.70 (t, 3H), 6.11 (m_c, 1H), 6.35-6.39 (m, 2H), 6.95 (d, 1H), 7.33 (dd, 1H), 7.50 (d, 2H), 7.82 (d, 1H), 7.91 (d, 2H), 8.30 (d, 1H), 8.84 (br. s, 1H), 9.51 (s, 1H). MS (ESpos): 462.2 [M+H]⁺.

EXAMPLE 35

Preparation of racemic 3-[(6-{[(2,4-dimethylphenyl)-(methyl)oxido-λ⁴-sulphanylidene]amino}quinolin-4-yl)amino]-5-methoxy-phenol

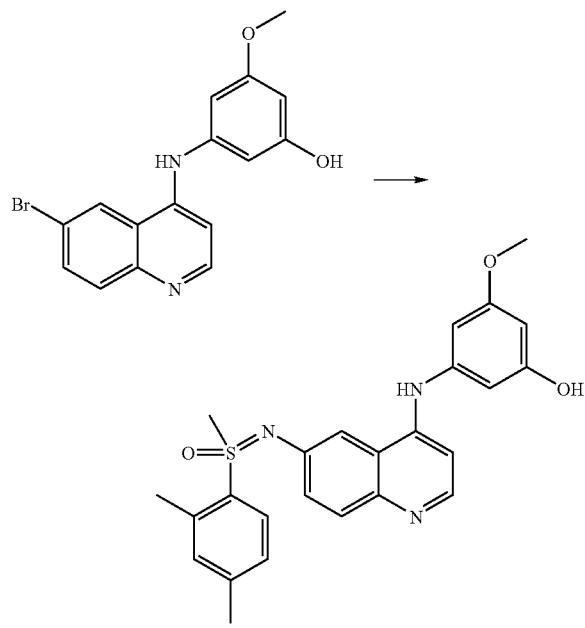

The title compound is prepared starting from 3-(6-bromoquinolin-4-ylamino)-5-methoxyphenol (intermediate 5) and S-(2,4-dimethylphenyl)-S-methyl-sulphoximine in analogy to the synthesis of the compound of Example 17 (method D).

¹H-NMR (400 MHz, D6-DMSO): δ=2.34 (s, 3H), 2.60 (s, 3H), 3.45 (s, 3H), 3.70 (s, 3H), 6.09 (m_c, 1H), 6.35 (m_c, 1H), 6.36 (m_c, 1H), 6.95 (d, 1H), 7.25 (dd, 1H), 7.27 (d, 1H), 7.36 (d, 1H), 7.58 (d, 1H), 7.74 (d, 1H), 7.94 (s, 1H), 8.29 (d, 1H), 8.71 (br. s, 1H), 9.47 (s, 1H). MS (ESpos): 448.2 [M+H]⁺.

EXAMPLE 36

Preparation of racemic 3-methoxy-5-[(6-{[methyl(naphthalen-2-yl)oxido-λ⁴-sulphanylidene]amino}quinolin-4-yl)amino]phenol

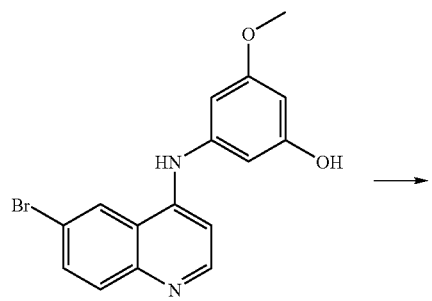

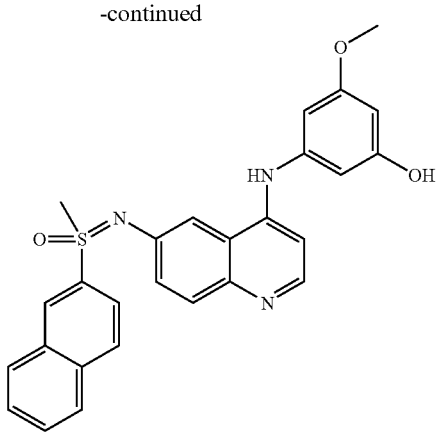

The title compound is prepared starting from 3-(6-bromoquinolin-4-ylamino)-5-methoxyphenol (intermediate 5) and S-(2-naphthyl)-S-methylsulphoximine in analogy to the synthesis of the compound of Example 17 (method D).

¹H-NMR (400 MHz, D6-DMSO): δ=3.56 (s, 3H), 3.71 (s, 3H), 6.14 (s, 1H), 6.36-6.39 (m, 2H), 7.38 (dd, 1H), 7.60 (d, 1H), 7.64-7.75 (m, 2H), 7.91 (s, 1H), 7.99 (dd, 1H), 8.04 (d, 1H), 8.12-8.20 (m, 2H), 8.28 (d, 1H), 8.71 (s, 1H), ca. 9.06 (br. s, 1H), 9.55 (s, 1H). MS (ESpos): 470.2 [M+H]⁺.

EXAMPLE 37

Preparation of racemic N-[3-(N-{4-[(3-hydroxy-5-methoxy-phenyl)amino]quinolin-6-yl}-S-methylsulphonimidoyl)phenyl]acetamide

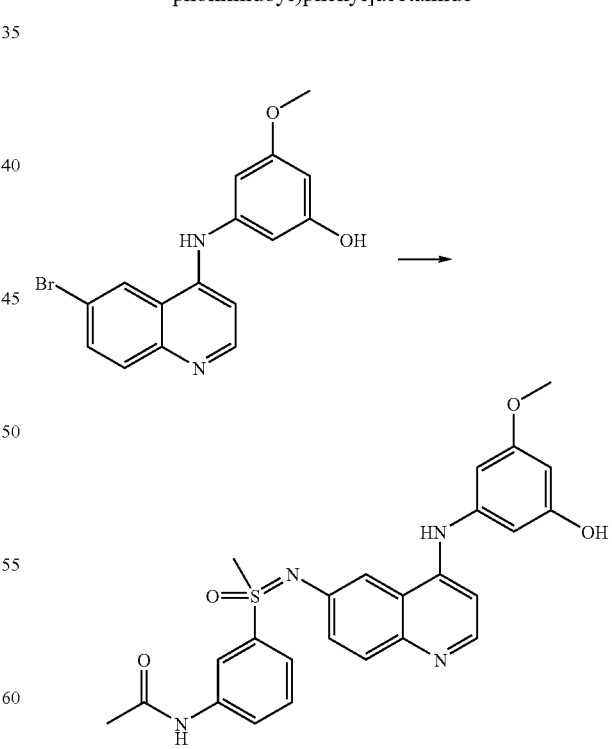

The title compound is prepared starting from 3-(6-bromoquinolin-4-ylamino)-5-methoxyphenol (intermediate 5) and S-(3-acetylaminophenyl)-S-methyl-sulphoximine in analogy to the synthesis of the compound of Example 17 (method D).

¹H-NMR (400 MHz, D6-DMSO): δ=2.05 (s, 3H), 3.42 (s, 3H), 3.70 (s, 3H), 6.07 (m$_c$, 1H), 6.35-6.39 (m, 2H), 6.97 (d, 1H), 7.26 (dd, 1H), 7.54 (dd, 1H), 7.60 (d, 1H), 7.63 (d, 1H), 7.77-7.82 (d, 2H), 8.30 (d, 1H), 8.32 (m$_c$, 1H), 8.62 (br. s, 1H), 9.46 (s, 1H), 10.30 (s, 1H). MS (ESpos): 477.2 [M+H]⁺.

EXAMPLE 38

Preparation of racemic 3-[(6-{[tert-butyl(methyl)oxido-λ⁴-sulphanylidene]amino}quinolin-4-yl)amino]-5-methoxyphenol

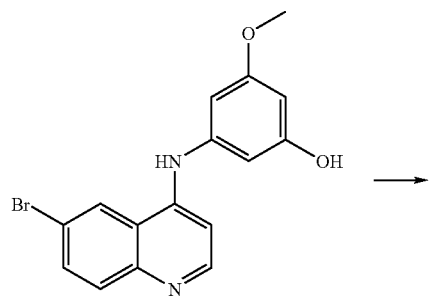

The title compound is prepared starting from 3-(6-bromo-quinolin-4-ylamino)-5-methoxyphenol (intermediate 5) and S-(tert-butyl)-S-methylsulphoximine in analogy to the synthesis of the compound of Example 17 (method D).

¹H-NMR (400 MHz, D6-DMSO): δ=1.47 (s, 9H), 3.07 (s, 3H), 3.69 (s, 3H), 6.05 (m$_c$, 1H), 6.33 (m$_c$, 1H), 6.37 (m$_c$, 1H), 6.99 (d, 1H), 7.42 (dd, 1H), 7.68 (d, 1H), 7.70 (d, 1H), 8.31 (d, 1H), 8.56 (s, 1H), 9.44 (s, 1H). MS (ESpos): 400.2 [M+H]⁺.

EXAMPLE 39

Preparation of racemic 3-methoxy-5-[(6-{[methyl(naphthalen-1-yl)oxido-λ⁴-sulphanylidene]amino}quinolin-4-yl)amino]phenol

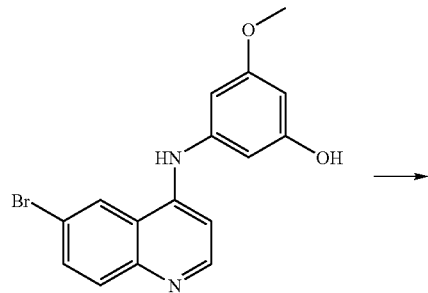

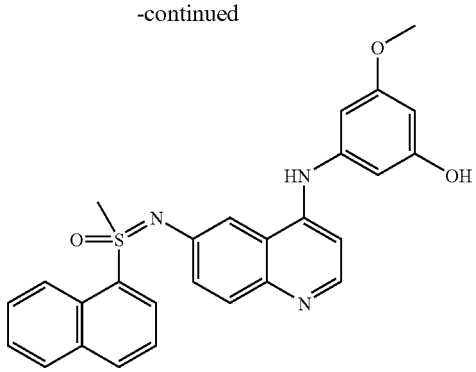

The title compound is prepared starting from 3-(6-bromo-quinolin-4-ylamino)-5-methoxyphenol (intermediate 5) and S-(1-naphthyl)-S-methylsulphoximine in analogy to the synthesis of the compound of Example 17 (method D).

¹H-NMR (400 MHz, D6-DMSO): δ=3.62 (s, 3H), 3.71 (s, 3H), 6.17 (s, 1H), 6.37 (d, 2H), 6.88 (d, 1H), 7.37 (dd, 1H), 7.55 (d, 1H), 7.66 (t, 1H), 7.7-7.81 (m, 2H), 7.91 (s, 1H), 8.1 (d, 1H), 8.26 (d, 1H), 8.30 (d, 1H), 8.46 (d, 1H), 8.89 (d, 1H, 9.15 (br. s, 1H), 9.60 (s, 1H). MS (ESpos): 470.2 [M+H]⁺.

Method E

EXAMPLE 40

Preparation of 3-bromo-5-[[6-[[(R)-methyloxidophenyl-λ⁴-sulphanylidene]amino]quinolin-4-yl]amino]phenol

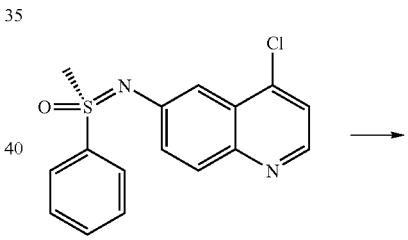

A solution of 48 mg (0.15 mmol) of 4-chloro-6-{[methyl(oxido)phenyl-λ⁴-sulphanylidene]amino}quinoline (intermediate 10) and 31 mg (0.165 mmol) of 3-amino-5-bromophenol in 2 ml of isopropanol is stirred under reflux for 2 days. The mixture is cooled and diluted with 10 ml of diethyl ether, and the precipitate which separates out is filtered off with suction. Drying under reduced pressure results in 42 mg (51%) of the title compound as hydrochloride salt.

¹H-NMR (400 MHz, D6-DMSO): δ=3.55 (s, 3H), 6.86 (br, 2H), 6.98 (br, 1H), 7.1 (br, 1H), 7.53-7.8. (m, 5H), 8.0-8.1 (m,

3H), 8.39 (d, 1H), 10.4 (s, 1H), 10.44 (s, 1H), 14.2 (br, 1H). MS (ESpos): 468.0 and 470.2 [M+H]+.

EXAMPLE 41

Preparation of 3-methyl-5-[[6-[[(R)-methyloxidophenyl-λ⁴-sulphanylidene]amino]quinolin-4-yl]amino]phenol

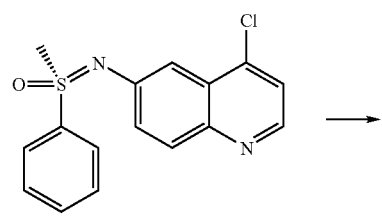

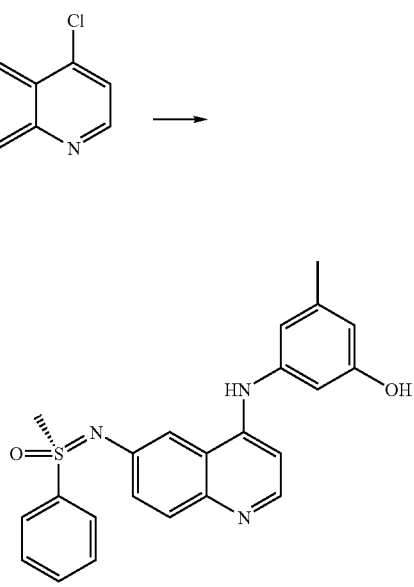

The title compound is prepared starting from 4-chloro-6-{[methyl(oxido)-phenyl-λ⁴-sulphanylidene]amino}quinoline (intermediate 10) and 3-amino-5-methylphenol in analogy to the synthesis of the compound of Example 40 (method E).

¹H-NMR (400 MHz, D6-DMSO): δ=2.28 (s, 3H), 3.54 (s, 3H), 6.62 (s, 2H), 6.68 (s, 1H), 6.76 (d, 1H), 7.55 (d, 1H), 7.64-7.78 (m, 4H), 8.04 (d, 2H), 8.11 (s, 1H), 8.33 (s, 1H), 9.78 (s, 1H), 9.9 (s, 1H), 14.02 (br, 1H). MS (DCl): 404.2 [M+H]+.

EXAMPLE 42

Preparation of 3-[(6-{[(R)-methyl(oxido)phenyl-λ⁴-sulphanylidene]amino}quinolin-4-yl)amino]-5-(trifluoromethyl)phenol

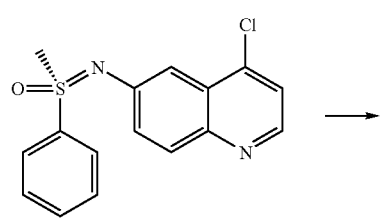

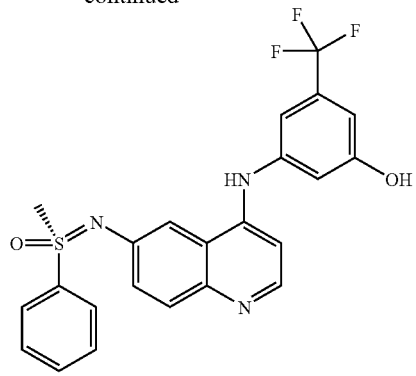

The title compound is prepared starting from 4-chloro-6-{[methyl(oxido)-phenyl-λ⁴-sulphanylidene]amino}quinoline (intermediate 10) and 3-amino-5-trifluoromethylphenol in analogy to the synthesis of the compound of Example 40 (method E).

¹H-NMR (400 MHz, D6-DMSO): δ=3.56 (s, 3H), 6.88 (d, 1H), 7.07 (s, 1H), 7.14 (s, 1H), 7.23 (s, 1H), 7.58 (dd, 1H), 7.63-7.76 (m, 3H), 7.79 (d, 1H), 8.04 (d, 2H), 8.10 (s, 1H), 8.41 (d, 1H), 10.54 (s, 1H), 10.63 (s, 1H), 14.25 (br, 1H). MS (DCl): 458.1 [M+H]+.

EXAMPLE 43

Preparation of N-(6-chloro-1H-indazol-4-yl)-6-{[(R)-methyl-(oxido)phenyl-λ⁴-sulphanylidene]amino}quinolin-4-amine

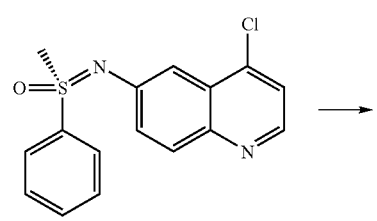

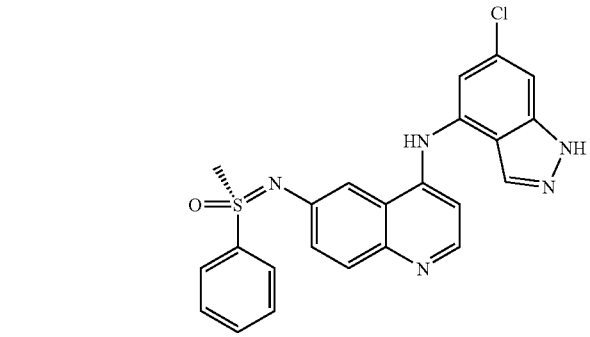

The title compound is prepared starting from 4-chloro-6-{[methyl(oxido)-phenyl-λ⁴-sulphanylidene]amino}quinoline (intermediate 10) and 6-chloro-1H-indazol-4-amine in analogy to the synthesis of the compound of Example 40 (method E).

¹H-NMR (400 MHz, D6-DMSO): δ=3.46 (s, 3H), 6.77 (d, 1H), 6.88 (br, 1H), 7.25 (s, 1H), 7.33 (dd, 1H), 7.59 (t, 2H), 7.63-7.72 (m, 2H), 7.76 (d, 1H), 7.95-7.99 (m, 3H), 8.38 (d, 1H), 13.0 (br, 1H). MS (DCI): 448.1 [M+H]⁺.

EXAMPLE 44

Preparation of 3-[(6-{[dimethyl(oxido)-λ⁴-sulphanylidene]-amino}quinolin-4-yl)oxy]-5-methoxyphenol

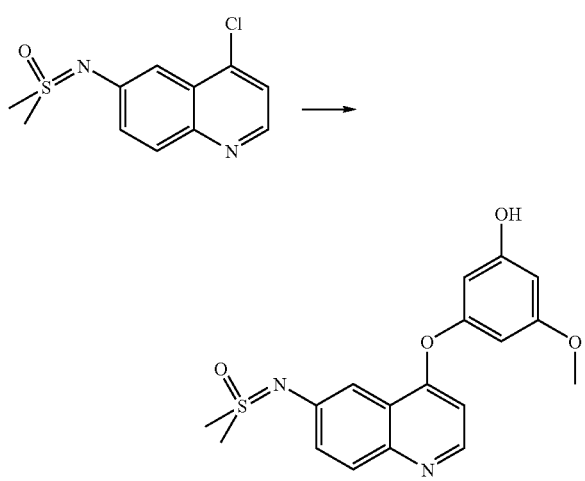

A solution of 50 mg (0.2 mmol) of 4-chloro-6-{[dimethyl(oxido)-λ⁴-sulphanylidene]amino}quinoline (intermediate 11), 41 mg (0.3 mmol) of 3,5-dihydroxyanisole and 17 mg (0.3 mmol) of potassium hydroxide in 2 ml of DMF is stirred under reflux overnight. The mixture is then cooled to RT and separated by preparative HPLC. 42 mg (60%) of the title compound are obtained.

¹H-NMR (400 MHz, D6-DMSO): δ=3.29 (s, 6H), 3.60 (s, 3H), 5.65 (br, 1H), 5.73 (br, 1H), 5.87 (br, 1H), 6.62 (d, 1H), 7.35 (dd, 1H), 7.64 (dd, 1H), 7.80 (d, 1H), 8.43 (d, 1H). MS (ESpos): 359.2 [M+H]⁺.

EXAMPLE 45

Preparation of 3-[(6-{[dimethyl(oxido)-λ⁴-sulphanylidene]-amino}quinolin-4-yl)oxy]-4-methylphenol

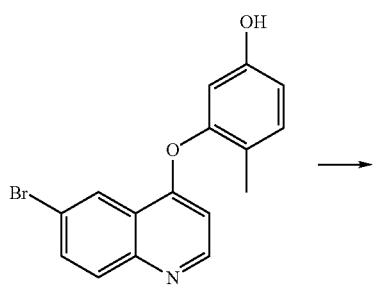

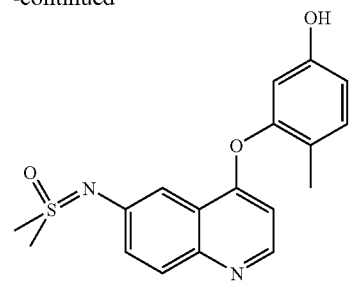

The title compound is prepared starting from 3-[(6-bromoquinolin-4-yl)oxy]-4-methylphenol (intermediate 15) and S,S-dimethylsulphoximine in analogy to the synthesis of the compound of Example 17 (method D).

¹H-NMR (400 MHz, D6-DMSO): δ=1.96 (s, 3H), 3.29 (s, 6H), 6.39 (d, 1H), 6.43 (dd, 1H), 6.59 (dd, 1H), 7.10 (d, 1H), 7.35 (dd, 1H), 7.70 (d, 1H), 7.85 (d, 1H), 8.43 (d, 1H). MS (ESpos): 343.1 [M+H]⁺.

Biological Tests on the Compounds
Test System for EphB4

A mixture of 20 ng/ml recombinanter EphB4 kinase (Pro-Qinase GmbH, Freiburg, Germany), 2.67 µg/ml polyGlu-AlaTyr, 2 µM ATP, 25 mM HEPES (pH 7.3), 5 mM MgCl₂, 1 mM MnCl₂, 2 mM DTT, 0.1 mM NaVO₄, 1% (v/v) glycerol, 0.02% NP40, EDTA-free protease inhibitors (Complete from Roche, 1 tablet in 50 ml) is incubated at 20° C. for 10 min. Test substances are dissolved in 100% DMSO and introduced in 0.017 times the volume before the start of the reaction. 60 minutes after addition of 1.7 times the volume of a solution of 50 mM Hepes pH 7.0, 0.2% BSA, 0.14 µg/ml PT66-europium, 3.84 µg/ml SA-XL665, 75 mM EDTA, the mixture is measured in a Perkin-Elmer Discovery HTRF measuring instrument.

Biology

Surprisingly, substances of the present invention possess inhibitory activity with respect to EphB4 with IC50 values of less than 10 µM.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

In the foregoing and in the examples, all temperatures are set forth uncorrected in degrees Celsius and, all parts and percentages are by weight, unless otherwise indicated.

The entire disclosures of all applications, patents and publications, cited herein and of corresponding German application No. 10 2007 024 470.5, filed May 24, 2007, of corresponding European application No. 07076116.8, filed Dec. 20, 2007, U.S. Provisional Application Ser. No. 60/940,233 filed May 25, 2007, and U.S. Provisional Application Ser. No. 61/020,908 filed Jan. 14, 2008, are incorporated by reference herein.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A compound according to formula (A):

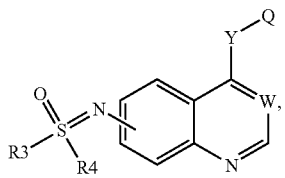

in which:

W is CH;

Y-Q is $NR^1R^2$ or $OR^1$;

$R^1$ and $R^2$ are identical or different and are independently selected from hydrogen, —$C_1$-$C_6$-alkyl, —$C_1$-$C_4$-hydroxyalkyl, —$C_2$-$C_6$-alkenyl, —$C_2$-$C_6$-alkynyl, —$C_3$-$C_{10}$-cycloalkyl, —$C_3$-$C_{12}$-heterocycloalkyl, —$C_6$-$C_{12}$-aryl, —$C_5$-$C_{18}$-heteroaryl, —$C_1$-$C_6$-alkoxy, —$C_1$-$C_6$-alkoxy-$C_1$-$C_6$-alkoxy, —$C_1$-$C_6$-alkoxy-$C_1$-$C_6$-alkyl, —$C_1$-$C_6$-alkoxy-$C_1$-$C_6$-alkoxy-$C_1$-$C_6$-alkyl, —$(CH_2)_n$—$C_6$-$C_{12}$-aryl, —$(CH_2)_n$—$C_5$-$C_{18}$-heteroaryl, —$(CH_2)_n$—$C_3$-$C_{10}$-cycloalkyl, —$(CH_2)_n$—$C_3$-$C_{12}$-heterocycloalkyl, -phenylene-$(CH_2)_p$—$R^6$, —$(CH_2)_p PO_3(R^6)_2$, —$(CH_2)_p$—$NR^5R^6$, —$(CH_2)_p$—$NR^4COR^5$, —$(CH_2)_p$—$NR^4CSR^5$, —$(CH_2)_p$—$NR^4S(O)R^5$, —$(CH_2)_p$—$NR^4S(O)_2R^5$, —$(CH_2)_p$—$NR^4CONR^5R^6$, —$(CH_2)_p$—$NR^4COOR^5$, —$(CH_2)_p$—$NR^4C(NH)NR^5R^6$, —$(CH_2)_p$—$NR^4CSNR^5R^6$, —$(CH_2)_p$—$NR^4S(O)NR^5R^6$, —$(CH_2)_p$—$NR^4S(O)_2NR^5R^6$, —$(CH_2)_p$—$COR^5$, —$(CH_2)_p$—$CSR^5$, —$(CH_2)_p$—$S(O)R^5$, —$(CH_2)_p$—$S(O)(NH)R^5$, —$(CH_2)_p$—$S(O)_2R^5$, —$(CH_2)_p$—$S(O)_2NR^5R^6$, —$(CH_2)_p$—$SO_2OR^5$, —$(CH_2)_p$—$CO_2R^5$, —$(CH_2)_p$—$CONR^5R^6$, —$(CH_2)_p$—$CSNR^5R^6$, —$OR^5$, —$CHR^5R^6$, —$(CH_2)_p$—$SR^5$, and —$CR^5(OH)$—$R^6$, where —$C_1$-$C_6$-alkyl, —$C_2$-$C_6$-alkenyl, —$C_2$-$C_6$-alkynyl, —$C_3$-$C_{10}$-cycloalkyl, —$C_3$-$C_{12}$-heterocycloalkyl, —$C_6$-$C_{12}$-aryl, —$C_5$-$C_{18}$-heteroaryl, and —$C_1$-$C_6$-alkoxy are each unsubstituted or substituted one or more times independently of one another by hydroxy, halogen, nitro, cyano, —$C_1$-$C_6$-alkyl, —$C_1$-$C_6$-haloalkyl, —$NR^5R^6$, —$C(O)NR^5R^6$, —$S(O)_2NR^5R^6$, —$NR^5S(O)_2R^6$, —$NR^5C(O)R^6$, —$SR^5$, —$R^5$, or —$OR^5$, and where the carbon framework of the —$C_3$-$C_{10}$-cycloalkyl and of the —$C_1$-$C_{10}$-alkyl optionally contain one or more times independently of one another nitrogen, oxygen, sulphur atoms, —$NR^4$ or C=O groups or one or more double bonds, or $R^1$ and $R^2$ optionally form together a bridge of 3-10 methylene units, where up to two methylene units are each optionally replaced by O, S or —$NR^4$;

$R^3$ and $R^4$ are selected independently of one another from hydrogen, —$C_1$-$C_{10}$-alkyl, —$C_2$-$C_6$-alkenyl, —$C_2$-$C_6$-alkynyl, —$C_3$-$C_{10}$-cycloalkyl, —$C_3$-$C_{12}$-heterocycloalkyl, —$C_6$-$C_{12}$-aryl, and —$C_1$-$C_{10}$-alkanoyl, where —$C_1$-$C_{10}$-alkyl, —$C_2$-$C_6$-alkenyl, —$C_2$-$C_6$-alkynyl, —$C_3$-$C_{10}$-cycloalkyl, —$C_3$-$C_{12}$-heterocycloalkyl, —$C_6$-$C_{12}$-aryl, and —$C_1$-$C_{10}$-alkanoyl are each unsubstituted or substituted one or more times independently of one another by hydroxy, halogen, nitro, cyano, phenyl, —$NR^5R^6$, —$C_1$-$C_{10}$-alkyl, —$SR^5$, or —$OR^5$, or $R^3$ and $R^4$ together with the respective sulphur atom to which they are attached, form a ring having 5, 6, 7, 8, 9 or 10 ring atoms, optionally consisting of carbon, nitrogen, oxygen or sulphur atoms;

$R^5$ and $R^6$ are identical or different and independently selected from hydrogen, —$C_1$-$C_{10}$-alkyl, —$C_2$-$C_{10}$-alkenyl, —$C_2$-$C_{10}$-alkynyl, —$C_1$-$C_6$-alkoxy, —C(=O)$C_1$-$C_6$-alkyl, —$C_3$-$C_{10}$-cycloalkyl, —$C_3$-$C_{12}$-heterocycloalkyl, —$C_6$-$C_{12}$-aryl, and —$C_5$-$C_{18}$-heteroaryl, where —$C_1$-$C_{10}$-alkyl, —$C_2$-$C_{10}$-alkenyl, —$C_2$-$C_{10}$-alkynyl, —$C_1$-$C_6$-alkoxy, —$C_3$-$C_{10}$-cycloalkyl, —$C_3$-$C_{12}$-heterocycloalkyl, —$C_6$-$C_{12}$-aryl, and —$C_5$-$C_{18}$-heteroaryl are each unsubstituted or substituted one or more times independently of one another by hydroxy, halogen, cyano, nitro, —$OR^7$, —$NR^7R^8$, —$C(O)NR^7R^8$, —$C(O)OR^7$, or —$C_1$-$C_6$-alkyl, where —$C_1$-$C_6$-alkyl is substituted one or more times independently of one another by halogen, hydroxy, cyano, —$NR^7R^8$, —$OR^7$, or phenyl, or $R^5$ and $R^6$ optionally together form a bridge of 3-10 methylene units, where up to two methylene units are optionally replaced by O, S or $NR^4$;

$R^7$, $R^8$ are identical or different and are independently selected from hydrogen, —$C_1$-$C_4$-alkyl, —$C_6$-$C_{12}$-aryl, and —$C_5$-$C_{18}$-heteroaryl, where alkyl, aryl, and heteroaryl is in each case unsubstituted or is substituted one or more times independently of one another by halogen or alkoxy, or $R^7$ and $R^8$ optionally together form a bridge of 3-10 methylene units, where up to two methylene units are optionally replaced by O, S or —$NR^4$;

n=1, 2, 3, 4, 5, or 6;

p=0, 1, 2, 3, 4, 5, or 6; or an N-oxide, stereoisomer, diastereomer, enantiomer, or physiologically tolerated salt thereof.

2. A compound according to claim 1, wherein:

Y-Q is $NR^1R^2$;

$R^1$ and $R^2$ are identical or different and are independently selected from hydrogen, —$C_1$-$C_6$-alkyl, —$C_1$-$C_4$-hydroxyalkyl, —$C_2$-$C_6$-alkenyl, —$C_2$-$C_6$-alkynyl, —$C_3$-$C_{10}$-cycloalkyl, —$C_3$-$C_{12}$-heterocycloalkyl, —$C_6$-$C_{12}$-aryl, —$C_5$-$C_{18}$-heteroaryl, —$C_1$-$C_6$-alkoxy, —$C_1$-$C_6$-alkoxy-$C_1$-$C_6$-alkoxy, —$C_1$-$C_6$-alkoxy-$C_1$-$C_6$-alkyl, —$C_1$-$C_6$-alkoxy-$C_1$-$C_6$-alkoxy-$C_1$-$C_6$-alkyl, —$(CH_2)_n$—$C_6$-$C_{12}$-aryl, —$(CH_2)_n$—$C_5$-$C_{18}$-heteroaryl, —$(CH_2)_n$—$C_3$-$C_{10}$-cycloalkyl, —$(CH_2)_n$—$C_3$-$C_{12}$-heterocycloalkyl, -phenylene-$(CH_2)_p$—$R^6$, —$(CH_2)_p$—$NR^5R^6$, —$(CH_2)_p$—$NR^4COR^5$, —$(CH_2)_p$—$NR^4CSR^5$, —$(CH_2)_p$—$NR^4S(O)R^5$, —$(CH_2)_p$—$NR^4S(O)_2R^5$, —$(CH_2)_p$—$NR^4CONR^5R^6$, —$(CH_2)_p$—$NR^4COOR^5$, —$(CH_2)_p$—$NR^4C(NH)NR^5R^6$, —$(CH_2)_p$—$NR^4CSNR^5R^6$, —$(CH_2)_p$—$NR^4S(O)NR^5R^6$, —$(CH_2)_p$—$NR^4S(O)_2NR^5R^6$, —$(CH_2)_p$—$COR^5$, —$(CH_2)_p$—$CSR^5$, —$(CH_2)_p$—$S(O)R^5$, —$(CH_2)_p$—$S(O)(NH)R^5$, —$(CH_2)_p$—$S(O)_2R^5$, —$(CH_2)_p$—$S(O)_2NR^5R^6$, —$(CH_2)_p$—$SO_2OR^5$, —$(CH_2)_p$—$CO_2R^5$, —$(CH_2)_p$—$CONR^5R^6$, —$(CH_2)_p$—$CSNR^5R^6$, —$OR^5$, —$CHR^5R^6$, —$(CH_2)_p$—$SR^5$, and —$CR^5(OH)$—$R^6$, where —$C_1$-$C_6$-alkyl, —$C_2$-$C_6$-alkenyl, —$C_2$-$C_6$-alkynyl, —$C_3$-$C_{10}$-cycloalkyl, —$C_3$-$C_{12}$-heterocycloalkyl, —$C_6$-$C_{12}$-aryl, —$C_5$-$C_{18}$-heteroaryl, and —$C_1$-$C_6$-alkoxy are in each case unsubstituted or substituted one or more times independently of one another by hydroxy, halogen, nitro, cyano, —$C_1$-$C_6$-alkyl, —$C_1$-$C_6$-haloalkyl, —$NR^5R^6$, —$C(O)NR^5R^6$, —$S(O)_2NR^5R^6$, —$NR^5S(O)_2R^6$, —$NR^5C(O)R^6$, —$SR^5$, —$R^5$, or —$OR^5$, and where the carbon framework of the —$C_3$-$C_{10}$-cycloalkyl and of the —$C_1$-$C_{10}$-alkyl may comprise one or more times independently of one another nitrogen, oxygen, sulphur atoms, —$NR^4$ or C=O groups or one or more double bonds, or $R^1$ and $R^2$ optionally together form a bridge of 3-10 methylene units, where up to two methylene units are each optionally replaced by O, S or —$NR^4$;

$R^3$ and $R^4$ are independently selected from hydrogen, —$C_1$-$C_{10}$-alkyl, —$C_2$-$C_6$-alkenyl, —$C_2$-$C_6$-alkynyl, —$C_3$-$C_{10}$-cycloalkyl, —$C_3$-$C_{12}$-heterocycloalkyl, —$C_6$-$C_{12}$-aryl, and —$C_1$-$C_{10}$-alkanoyl, where —$C_1$-$C_{10}$-alkyl, —$C_2$-$C_6$-alkenyl, —$C_2$-$C_6$-alkynyl, —$C_3$-$C_{10}$-cycloalkyl, —$C_3$-$C_{12}$-heterocycloalkyl, —$C_6$-$C_{12}$-aryl, and —$C_1$-$C_{10}$-alkanoyl is in each case unsubstituted or substituted one or more times independently of one another by hydroxy, halogen, nitro, cyano, phenyl, —$NR^5R^6$, —$C_1$-$C_{10}$-alkyl, —$SR^5$, or —$OR^5$, or $R^3$ and $R^4$ optionally, together with the respective sulphur atom to which they are attached, form a ring, the ring having 5, 6, 7, 8, 9 or 10 ring atoms, optionally consisting of carbon, nitrogen, oxygen or sulphur atoms;

$R^5$ and $R^6$ are identical or different and are independently selected from hydrogen, —$C_1$-$C_{10}$-alkyl, —$C_2$-$C_{10}$-alkenyl, —$C_2$-$C_{10}$-alkynyl, —$C_1$-$C_6$-alkoxy, —$C(=O)$—$C_1$-$C_6$-alkyl, —$C_3$-$C_{10}$-cycloalkyl, —$C_3$-$C_{12}$-heterocycloalkyl, —$C_6$-$C_{12}$-aryl, and —$C_5$-$C_{18}$-heteroaryl, where —$C_1$-$C_{10}$-alkyl, —$C_2$-$C_{10}$-alkenyl, —$C_2$-$C_{10}$-alkynyl, —$C_1$-$C_6$-alkoxy, —$C_3$-$C_{10}$-cycloalkyl, —$C_3$-$C_{12}$-heterocycloalkyl, —$C_6$-$C_{12}$-aryl, and —$C_5$-$C_{18}$-heteroaryl are in each case unsubstituted or substituted one or more times independently of one another by hydroxy, halogen, cyano, nitro, —$OR^7$, —$NR^7R^8$, —$C(O)NR^7R^8$, —$C(O)OR^7$, or —$C_1$-$C_6$-alkyl, where —$C_1$-$C_6$-alkyl is unsubstituted or substituted one or more times independently of one another by halogen, hydroxy, cyano, —$NR^7R^8$, —$OR^7$ or phenyl, or $R^5$ and $R^6$ optionally together form a bridge of 3-10 methylene units, where up to two methylene units are each optionally replaced by O, S or $NR^4$;

$R^7$, $R^8$ are identical or different and are independently selected from hydrogen, —$C_1$-$C_4$-alkyl, —$C_6$-$C_{12}$-aryl, and —$C_5$-$C_{18}$-heteroaryl, where alkyl, aryl, and heteroaryl is in each case unsubstituted or is substituted one or more times independently of one another by halogen or alkoxy, or $R^7$ and $R^8$ optionally together form a bridge of 3-10 methylene units, where up to two methylene units are each optionally replaced by O, S or —$NR^4$;

n=1, 2, 3, 4, 5, or 6;

p=0, 1, 2, 3, 4, 5, or 6; or an N-oxide, stereoisomer, diastereomer, enantiomer, or physiologically tolerated salt thereof.

3. A compound according to claim 1, wherein:

Y-Q is $NR^1R^2$;

$R^1$ is hydrogen, —$C_1$-$C_6$-alkyl, —$C_1$-$C_4$-hydroxyalkyl, —$C_2$-$C_6$-alkenyl, —$C_2$-$C_6$-alkynyl, —$C_3$-$C_{10}$-cycloalkyl, —$C_3$-$C_{12}$-heterocycloalkyl, —$C_6$-$C_{12}$-aryl, —$C_5$-$C_{18}$-heteroaryl, —$C_1$-$C_6$-alkoxy, —$C_1$-$C_6$-alkoxy-$C_1$-$C_6$-alkoxy, —$C_1$-$C_6$-alkoxy-$C_1$-$C_6$-alkyl, —$C_1$-$C_6$-alkoxy-$C_1$-$C_6$-alkoxy-$C_1$-$C_6$-alkyl, —$(CH_2)_n$—$C_6$-$C_{12}$-aryl, —$(CH_2)_n$—$C_5$-$C_{18}$-heteroaryl, —$(CH_2)_n$—$C_3$-$C_{10}$-cycloalkyl, —$(CH_2)_n$—$C_3$-$C_{12}$-heterocycloalkyl, -phenylene-$(CH_2)_p$—$R^6$, —$(CH_2)_p$—$NR^5R^6$, —$(CH_2)_p$—$NR^4COR^5$, —$(CH_2)_p$—$NR^4CSR^5$, —$(CH_2)_p$—$NR^4S(O)R^5$, —$(CH_2)_p$—$NR^4S(O)_2R^5$, —$(CH_2)_p$—$NR^4CONR^5R^6$, —$(CH_2)_p$—$NR^4COOR^5$, —$(CH_2)_p$—$NR^4C(NH)NR^5R^6$, —$(CH_2)_p$—$NR^4CSNR^5R^6$, —$(CH_2)_p$—$NR^4S(O)NR^5R^6$, —$(CH_2)_p$—$NR^4S(O)_2NR^5R^6$, —$(CH_2)_p$—$COR^5$, —$(CH_2)_p$—$CSR^5$, —$(CH_2)_p$—$S(O)R^5$, —$(CH_2)_p$—$S(O)(NH)R^5$, —$(CH_2)_p$—$S(O)_2R^5$, —$(CH_2)_p$—$S(O)_2NR^5R^6$, —$(CH_2)_p$—$SO_2OR^5$, —$(CH_2)_p$—$CO_2R^5$, —$(CH_2)_p$—$CONR^5R^6$, —$(CH_2)_p$—$CSNR^5R^6$, —$OR^5$, —$CHR^5R^6$, —$(CH_2)_p$—$SR^5$, or —$CR^5(OH)$—$R^6$, where —$C_1$-$C_6$-alkyl, —$C_2$-$C_6$-alkenyl, —$C_2$-$C_6$-alkynyl, —$C_3$-$C_{10}$-cycloalkyl, —$C_3$-$C_{12}$-heterocycloalkyl, —$C_6$-$C_{12}$-aryl, —$C_5$-$C_{18}$-heteroaryl, and —$C_1$-$C_6$-alkoxy are in each case unsubstituted or substituted one or more times independently of one another by hydroxy, halogen, nitro, cyano, —$C_1$-$C_6$-alkyl, —$C_1$-$C_6$-haloalkyl, —$NR^5R^6$, —$C(O)NR^5R^6$, —$S(O)_2NR^5R^6$, —$NR^5S(O)_2R^6$, —$NR^5C(O)R^6$, —$SR^5$, —$R^5$, or —$OR^5$, where the carbon framework of the —$C_3$-$C_{10}$-cycloalkyl and of the —$C_1$-$C_{10}$-alkyl may comprise one or more times independently of one another nitrogen, oxygen, sulphur atoms, —$NR^4$ or C=O groups or one or more double bonds, or $R^1$ and $R^2$ optionally together form a bridge of 3-10 methylene units, where up to two methylene units are each optionally replaced by O, S or —$NR^4$;

$R^2$ is a hydrogen atom;

$R^3$ and $R^4$ are each independently selected from hydrogen, —$C_1$-$C_{10}$-alkyl, —$C_2$-$C_6$-alkenyl, —$C_2$-$C_6$-alkynyl, —$C_3$-$C_{10}$-cycloalkyl, —$C_3$-$C_{12}$-heterocycloalkyl, —$C_6$-$C_{12}$-aryl, and —$C_1$-$C_{10}$-alkanoyl, where —$C_1$-$C_{10}$-alkyl, —$C_2$-$C_6$-alkenyl, —$C_2$-$C_6$-alkynyl, —$C_3$-$C_{10}$-cycloalkyl, —$C_3$-$C_{12}$-heterocycloalkyl, —$C_6$-$C_{12}$-aryl, and —$C_1$-$C_{10}$-alkanoyl are in each case unsubstituted or substituted one or more times independently of one another by hydroxy, halogen, nitro, cyano, phenyl, —$NR^5R^6$, —$C_1$-$C_{10}$-alkyl, —$SR^5$ or —$OR^5$, or $R^3$ and $R^4$ optionally, together with the respective sulphur atom to which they are attached, form a ring, the ring having 5, 6, 7, 8, 9 or 10 ring atoms, optionally consisting of carbon, nitrogen, oxygen or sulphur atoms;

$R^5$ and $R^6$ are identical or different and are-independently selected from hydrogen, —$C_1$-$C_{10}$-alkyl, —$C_2$-$C_{10}$-alkenyl, —$C_2$-$C_{10}$-alkenyl, —$C_1$-$C_6$-alkoxy, —$C(=O)$—$C_1$-$C_6$-alkyl, —$C_3$-$C_{10}$-cycloalkyl, —$C_3$-$C_{12}$-heterocycloalkyl, —$C_6$-$C_{12}$-aryl, and —$C_5$-$C_{18}$-heteroaryl, where —$C_1$-$C_{10}$-alkyl, —$C_2$-$C_{10}$-alkenyl, —$C_2$-$C_{10}$-alkynyl, —$C_1$-$C_6$-alkoxy, —$C_3$-$C_{10}$-cycloalkyl, —$C_3$-$C_{12}$-heterocycloalkyl, —$C_6$-$C_{12}$-aryl, and —$C_5$-$C_{18}$-heteroaryl are in each case unsubstituted or substituted one or more times independently of one another by hydroxy, halogen, cyano, nitro, —$OR^7$, —$NR^7R^8$, —$C(O)NR^7R^8$, —$C(O)OR^7$, or —$C_1$-$C_6$-alkyl, where —$C_1$-$C_6$-alkyl is unsubstituted or is substituted one or more times independently of one another by halogen, hydroxy, cyano, —$NR^7R^8$, —$OR^7$ or phenyl, or $R^5$ and $R^6$ optionally together form a bridge of 3-10 methylene units, where up to two methylene units are each optionally replaced by O, S or $NR^4$;

$R^7$, $R^8$ are identical or different and are independently selected from hydrogen, —$C_1$-$C_4$-alkyl, —$C_6$-$C_{12}$-aryl, and —$C_5$-$C_{18}$-heteroaryl, where alkyl, aryl, and heteroaryl are in each case unsubstituted or substituted one or more times independently of one another by halogen or alkoxy, or $R^7$ and $R^8$ optionally together form a bridge of 3-10 methylene units, where up to two methylene units are each optionally replaced by O, S or —$NR^4$;

n=1, 2, 3, 4, 5, or 6;

p=0, 1, 2, 3, 4, 5, or 6; or an N-oxide, stereoisomer, diastereomer, enantiomer or physiologically tolerated salt thereof.

4. A compound according to claim 1, wherein:
Y-Q is OR$^1$;
R$^1$ is hydrogen, —C$_1$-C$_6$-alkyl, —C$_1$-C$_4$-hydroxyalkyl, —C$_2$-C$_6$-alkenyl, —C$_2$-C$_6$-alkynyl, —C$_3$-C$_{10}$-cycloalkyl, —C$_3$-C$_{12}$-heterocycloalkyl, —C$_6$-C$_{12}$-aryl, —C$_5$-C$_{18}$-heteroaryl, —C$_1$-C$_6$-alkoxy, —C$_1$-C$_6$-alkoxy-C$_1$-C$_6$-alkoxy, —C$_1$-C$_6$-alkoxy-C$_1$-C$_6$-alkyl, —C$_1$-C$_6$-alkoxy-C$_1$-C$_6$-alkoxy-C$_1$-C$_6$-alkyl, —(CH$_2$)$_n$—C$_6$-C$_{12}$-aryl, —(CH$_2$)$_n$—C$_5$-C$_{18}$-heteroaryl, —(CH$_2$)$_n$—C$_3$-C$_{10}$-cycloalkyl, —(CH$_2$)$_n$—C$_3$-C$_{12}$-heterocycloalkyl, -phenylene-(CH$_2$)$_p$—R$^6$, —(CH$_2$)$_p$—NR$^5$R$^6$, —(CH$_2$)$_p$—NR$^4$COR$^5$, —(CH$_2$)$_p$—NR$^4$CSR$^5$, —(CH$_2$)$_p$—NR$^4$S(O)R$^5$, —(CH$_2$)$_p$—NR$^4$S(O)$_2$R$^5$, —(CH$_2$)$_p$—NR$^4$CONR$^5$R$^6$, —(CH$_2$)$_p$—NR$^4$COOR$^5$, —(CH$_2$)$_p$—NR$^4$C(NH)NR$^5$R$^6$, —(CH$_2$)$_p$—NR$^4$CSNR$^5$R$^6$, —(CH$_2$)$_p$—NR$^4$S(O)NR$^5$R$^6$, —(CH$_2$)$_p$—NR$^4$S(O)$_2$NR$^5$R$^6$, —(CH$_2$)$_p$—COR$^5$, —(CH$_2$)$_p$—CSR$^5$, —(CH$_2$)$_p$—S(O)R$^5$, —(CH$_2$)$_p$—S(O)(NH)R$^5$, —(CH$_2$)$_p$—S(O)$_2$R$^5$, —(CH$_2$)$_p$—S(O)$_2$NR$^5$R$^6$, —(CH$_2$)$_p$—SO$_2$OR$^5$, —(CH$_2$)$_p$—CO$_2$R$^5$, —(CH$_2$)$_p$—CONR$^5$R$^6$, —(CH$_2$)$_p$—CSNR$^5$R$^6$, —OR$^5$, —CHR$^5$R$^6$, —(CH$_2$)$_p$—SR$^5$, or —CR$^5$(OH)—R$^6$, where —C$_1$-C$_6$-alkyl, —C$_2$-C$_6$-alkenyl, —C$_2$-C$_6$-alkynyl, —C$_3$-C$_{10}$-cycloalkyl, —C$_3$-C$_{12}$-heterocycloalkyl, —C$_6$-C$_{12}$-aryl, —C$_5$-C$_{18}$-heteroaryl, and —C$_1$-C$_6$-alkoxy are in each case unsubstituted or substituted one or more times independently of one another by hydroxy, halogen, nitro, cyano, —C$_1$-C$_6$-alkyl, —C$_1$-C$_6$-haloalkyl, —NR$^5$R$^6$, —C(O)NR$^5$R$^6$, —S(O)$_2$NR$^5$R$^6$, —NR$^5$S(O)$_2$R$^6$, —NR$^5$C(O)R$^6$, —SR$^5$, —R$^5$, or —OR$^5$, where the carbon framework of the —C$_3$-C$_{10}$-cycloalkyl and of the —C$_1$-C$_{10}$-alkyl may comprise one or more times independently of one another nitrogen, oxygen, sulphur atoms, —NR$^4$ or C═O groups or one or more double bonds, or R$^1$ and R$^2$ optionally together form a bridge of 3-10 methylene units, where up to two methylene units are each optionally replaced by O, S or —NR$^4$;

R$^3$ and R$^4$ are independently selected from hydrogen, —C$_1$-C$_{10}$-alkyl, —C$_2$-C$_6$-alkenyl, —C$_2$-C$_6$-alkynyl, —C$_3$-C$_{10}$-cycloalkyl, —C$_3$-C$_{12}$-heterocycloalkyl, —C$_6$-C$_{12}$-aryl, —C$_1$-C$_{10}$-alkanoyl, where —C$_1$-C$_{10}$-alkyl, —C$_2$-C$_6$-alkenyl, —C$_2$-C$_6$-alkynyl, —C$_3$-C$_{10}$-cycloalkyl, —C$_3$-C$_{12}$-heterocycloalkyl, —C$_6$-C$_{12}$-aryl, and —C$_1$-C$_{10}$-alkanoyl are in each case unsubstituted or substituted one or more times independently of one another by hydroxy, halogen, nitro, cyano, phenyl, —NR$^5$R$^6$, —C$_1$-C$_{10}$-alkyl, —SR$^5$ or —OR$^5$, or R$^3$ and R$^4$ optionally, together with the respective sulphur atom to which they are attached, form a ring, the ring having 5, 6, 7, 8, 9 or 10 ring atoms, optionally consisting of carbon, nitrogen, oxygen or sulphur atoms;

R$^5$ and R$^6$ are identical or different and are independently selected from hydrogen, —C$_1$-C$_{10}$-alkyl, —C$_2$-C$_{10}$-alkenyl, —C$_2$-C$_{10}$-alkynyl, —C$_1$-C$_6$-alkoxy, —C(═O)—C$_1$-C$_6$-alkyl, —C$_3$-C$_{10}$-cycloalkyl, —C$_3$-C$_{12}$-heterocycloalkyl, —C$_6$-C$_{12}$-aryl, and —C$_5$-C$_{18}$-heteroaryl, where —C$_1$-C$_{10}$-alkyl, —C$_2$-C$_{10}$-alkenyl, —C$_2$-C$_{10}$-alkynyl, —C$_1$-C$_6$-alkoxy, —C$_3$-C$_{10}$-cycloalkyl, —C$_3$-C$_{12}$-heterocycloalkyl, —C$_6$-C$_{12}$-aryl, and —C$_5$-C$_{18}$-heteroaryl are in each case unsubstituted or substituted one or more times independently of one another by hydroxy, halogen, cyano, nitro, —OR$^7$, —NR$^7$R$^8$, —C(O)NR$^7$R$^8$, —C(O)OR$^7$, or —C$_1$-C$_6$-alkyl, where —C$_1$-C$_6$-alkyl is unsubstituted or is substituted one or more times independently of one another by halogen, hydroxy, cyano, —NR$^7$R$^8$, —OR$^7$ or phenyl, or R$^5$ and R$^6$ optionally together form a bridge of 3-10 methylene units, where up to two methylene units are each optionally replaced by O, S or NR$^4$;

R$^7$, R$^8$ are identical or different and are independently selected from hydrogen, —C$_1$-C$_4$-alkyl, —C$_6$-C$_{12}$-aryl, and —C$_5$-C$_{18}$-heteroaryl, where alkyl, aryl, and heteroaryl are in each case unsubstituted or substituted one or more times independently of one another by halogen or alkoxy, or R$^7$ and R$^8$ optionally together form a bridge of 3-10 methylene units, where up to two methylene units are each optionally replaced by O, S or —NR$^4$;

n=1, 2, 3, 4, 5, or 6;

p=0, 1, 2, 3, 4, 5, or 6; or an N-oxide, stereoisomer, diastereomer, enantiomer, or physiologically tolerated salt thereof.

5. A compound according to claim 1, wherein R$^3$ is —C$_1$-C$_{10}$-alkyl; or an N-oxide, stereoisomer, diastereomer, enantiomer, or physiologically tolerated salt thereof.

6. A compound according to claim 1, wherein said compound is selected from:

4-methyl-3-[[6-[[(R)-methyloxidophenyl-λ$^4$-sulphanylidene]amino]-4-quinolinyl]amino]phenol;

4-methyl-3-[[6-[[(S)-methyloxidophenyl-λ$^4$-sulphanylidene]amino]-4-quinolinyl]amino]phenol;

3-[[6-[[(R)-methyloxidophenyl-λ$^4$-sulphanylidene]amino]-4-quinolinyl]amino]phenol;

3-[[6-[[(S)-methyloxidophenyl-λ$^4$-sulphanylidene]amino]-4-quinolinyl]amino]phenol;

3-[[6-[(dimethyloxido-λ$^4$-sulphanylidene)amino]-4-quinolinyl]amino]-4-methylphenol;

3-methoxy-5-[[6-[[(R)-methyloxidophenyl-λ$^4$-sulphanylidene]amino]-4-quinolinyl]amino]phenol;

3-methoxy-5-[[6-[[(S)-methyloxidophenyl-λ$^4$-sulphanylidene]amino]-4-quinolinyl]amino]phenol;

3-[[6-[(dimethyloxido-λ$^4$-sulphanylidene)amino]-4-quinolinyl]amino]-5-methoxyphenol;

3-methoxy-5-[(6-{[oxido(diphenyl)-λ$^4$-sulphanylidene]amino}quinolin-4-yl)amino]phenol;

3-[(6-{[(dimethyl(oxido)-λ$^4$-sulphanylidene]amino}quinolin-4-yl)amino]-4-methylphenol;

4-chloro-3-[(6-{[dimethyl(oxido)-λ$^4$-sulphanylidene]amino}quinolin-4-yl)amino]phenol;

4-chloro-3-[(6-{[(R)-methyl(oxido)phenol-λ$^4$-sulphanylidene]amino}quinolin-4-yl)amino]phenol;

4-methyl-3-[(6-{[oxido(diphenyl)-λ$^4$-sulphanylidene]amino}quinolin-4-yl)amino]phenol;

3-[(6-{[diethyl(oxido)-λ$^4$-sulphanylidene]amino}quinolin-4-yl)amino]-5-methoxyphenol;

3-[(6-{[ethyl(methyl)oxido-λ$^4$-sulphanylidene]amino}quinolin-4-yl)amino]-5-methoxyphenol;

3-methoxy-5-[(6-{[oxido(dipropyl)-λ$^4$-sulphanylidene]amino}quinolin-4-yl)amino]phenol;

3-[(6-{[cyclohexyl(methyl)oxido-λ$^4$-sulphanylidene]amino}quinolin-4-yl)amino]-5-methoxyphenol;

3-methoxy-5-({6-[(1-oxidotetrahydro-1H-1λ$^4$-thiophen-1-ylidene)amino]quinolin-4-yl}amino)phenol;

3-[(6-{[ethyl(oxido)phenyl-λ$^4$-sulphanylidene]amino}quinolin-4-yl)amino]-5-methoxyphenol;

3-[(6-{[(2-fluorophenyl)(methyl)oxido-λ$^4$-sulphanylidene]amino}quinolin-4-yl)amino]-5-methoxyphenol;

3-[(6-{[(4-fluorophenyl)(methyl)oxido-λ$^4$-sulphanylidene]amino}quinolin-4-yl)amino]-5-methoxyphenol;

3-[(6-{[(4-chlorophenyl)(methyl)oxido-λ⁴-sulpha-nylidene]amino}quinolin-4-yl)amino]-5-methoxyphenol;

3-[(6-{[(4-methylphenyl)(methyl)oxido-λ⁴-sulpha-nylidene]amino}quinolin-4-yl)amino]-5-methoxyphenol;

3-[(6-{[(3-methylphenyl)(methyl)oxido-λ⁴-sulpha-nylidene]amino}quinolin-4-yl)amino]-5-methoxyphenol;

3-[(6-{[(4-methoxyphenyl)(methyl)oxido-λ⁴-sulpha-nylidene]amino}quinolin-4-yl)amino]-5-methoxyphenol;

3-methoxy-5-{[6-({methyl[4-(1-methylethyl)phenyl]oxido-λ⁴-sulphanylidene}amino]quinolin-4-yl}amino)phenol;

3-[(6-{[(2,4-dimethylphenyl)(methyl)oxido-λ⁴-sulpha-nylidene]amino}quinolin-4-yl)amino]-5-methoxyphenol;

3-methoxy-5-[(6-{[methyl(naphthalene-2-yl)oxido-λ⁴-sulphanylidene]amino}quinolin-4-yl)amino]phenol;

N-[3-(N-{4-[(3-hydroxy-5-methoxyphenyl)amino]quinolin-6-yl}-S-methylsulphonimidoyl)phenyl]acetamide;

3-[(6-{[tert-butyl(methyl)oxido-λ⁴-sulphanylidene]amino}quinolin-4-yl)amino]-5-methoxyphenol;

3-methoxy-5-[(6-{[methyl(naphthalen-1-yl)oxido-λ⁴-sulphanylidene]amino}quinolin-4-yl)amino]phenol;

3-bromo-5-[[6-[[(R)-methyloxidophenyl-λ⁴-sulpha-nylidene]amino]quinolin-4-yl]amino]phenol;

3-methyl-5-[[6-[[(R)-methyloxidophenyl-λ⁴-sulpha-nylidene]amino]quinolin-4-yl]amino]phenol;

3-[(6-{[(R)-methyl(oxido)phenyl-λ⁴-sulphanylidene]amino}quinolin-4-yl)amino]-5-(trifluoromethyl)phenol;

N-(6-chloro-1H-indazol-4-yl)-6-{[(R)-methyl(oxido)phenyl-λ⁴-sulphanylidene]amino}quinolin-4-amine;

3-[(6-{[dimethyl(oxido)-λ⁴-sulphanylidene]amino}quinolin-4-yl)oxy]-5-methoxyphenol; and physiologically tolerated salts thereof.

7. A process for preparing a compound according to claim 1, said process comprising:

reacting an intermediate of formula II:

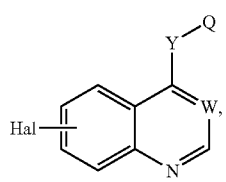

(II)

in which Hal is chloride, bromide or iodide, with a reagent of formula III:

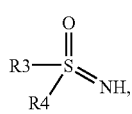

(III)

to give a compound of formula (A):

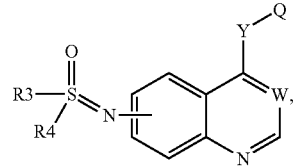

(A)

8. A compound according to claim 1, wherein said compound is a compound of the formula:

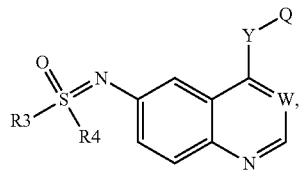

or an N-oxide, stereoisomer, diastereomer, enantiomer, or physiologically tolerated salt thereof.

9. A compound according to claim 8, wherein Y-Q is $NR^1R^2$.

10. A compound according to claim 9, wherein $R^1$ is hydrogen and $R^2$ is selected from $—C_1-C_6$-alkyl, $—C_6-C_{12}$-aryl, and $—C_5-C_{18}$-heteroaryl, which in each case is unsubstituted or substituted one or more times independently of one another by hydroxy, halogen, nitro, cyano, $—C_1-C_6$-alkyl, $—C_1-C_6$-haloalkyl, $—NR^5R^6$, $—C(O)NR^5R^6$, $—S(O)_2NR^5R^6$, $—NR^5S(O)_2R^6$, $—NR^5C(O)R^6$, $—SR^5$, $—R^5$, or $—OR^5$.

11. A compound according to claim 10, wherein $R^1$ is hydrogen and $R^2$ is selected from $—C_1-C_6$-alkyl, $—C_6-C_{12}$-aryl, and $—C_5-C_{18}$-heteroaryl, which in each case is unsubstituted or substituted one or more times independently of one another by hydroxy, halogen, $—C_1-C_6$-alkyl, $—C_1-C_6$-haloalkyl, -or $—OR^5$, and $R^5$ is $—C_1-C_{10}$-alkyl.

12. A compound according to claim 9, wherein $R^1$ is hydrogen and $R^2$ is selected from $—C_1-C_6$-alkyl, -phenyl, and quinolinyl, which in each case is unsubstituted or substituted one or more times independently of one another by hydroxy, halogen, nitro, cyano, $—C_1-C_6$-alkyl, $—C_1-C_6$-haloalkyl, $—NR^5R^6$, $—C(O)NR^5R^6$, $—S(O)_2NR^5R^6$, $—NR^5S(O)_2R^6$, $—NR^5C(O)R^6$, $—SR^5$, $—R^5$, or $—OR^5$.

13. A compound according to claim 9, wherein $R^1$ is hydrogen and $R^2$ is selected from $—C_1-C_6$-alkyl, -phenyl, and quinolinyl, which in each case is unsubstituted or substituted one or more times independently of one another by hydroxy, halogen, $—C_1-C_6$-alkyl, $—C_1-C_6$-haloalkyl, -or $—OR^5$, and $R^5$ is $—C_1-C_{10}$-alkyl.

14. A compound according to claim 9, wherein $R^3$ and $R^4$ are each independently $—C_1-C_{10}$-alkyl, $—C_3-C_{10}$-cycloalkyl, or $—C_6-C_{12}$-aryl, which in each case is unsubstituted or substituted one or more times independently of one another by hydroxy, halogen, nitro, cyano, phenyl, $—R^5R^6$, $—C_1-C_{10}$-alkyl, $—SR^5$, or $—OR^5$.

15. A compound according to claim 14, wherein $R^3$ and $R^4$ are each independently methyl, ethyl, propyl, cyclohexyl, phenyl, or naphthyl, which in each case is unsubstituted or substituted one or more times independently of one another by hydroxy, halogen, nitro, cyano, phenyl, $—R^5R^6$, $—C_1-C_{10}$-alkyl, $—SR^5$, or $—OR^5$.

16. A compound according to claim 10, wherein $R^3$ and $R^4$ are each independently —$C_1$-$C_{10}$-alkyl, —$C_3$-$C_{10}$-cycloalkyl, or —$C_6$-$C_{12}$-aryl, which in each case is unsubstituted or substituted one or more times independently of one another by hydroxy, halogen, nitro, cyano, phenyl, —$R^5R^6$, —$C_1$-$C_{10}$-alkyl, —$SR^5$, or —$OR^5$.

17. A compound according to claim 12, wherein $R^3$ and $R^4$ are each independently methyl, ethyl, propyl, cyclohexyl, phenyl, or naphthyl, which in each case is unsubstituted or substituted one or more times independently of one another by hydroxy, halogen, nitro, cyano, phenyl, —$R^5R^6$, —$C_1$-$C_{10}$-alkyl, —$SR^5$, or —$OR^5$.

18. A compound according to claim 1, wherein

Y-Q is $NR^1R^2$;

$R^1$ and $R^2$ are identical or different and are selected one or more times independently of one another from hydrogen, —$C_1$-$C_6$-alkyl, —$C_1$-$C_4$-hydroxyalkyl, —$C_2$-$C_6$-alkenyl, —$C_2$-$C_6$-alkynyl, —$C_3$-$C_{10}$-cycloalkyl, —$C_3$-$C_{12}$-heterocycloalkyl, —$C_6$-$C_{12}$-aryl, —$C_5$-$C_{18}$-heteroaryl, —$C_1$-$C_6$-alkoxy, —$C_1$-$C_6$-alkoxy-$C_1$-$C_6$-alkoxy, —$C_1$-$C_6$-alkoxy-$C_1$-$C_6$-alkyl, —$C_1$-$C_6$-alkoxy-$C_1$-$C_6$-alkoxy-$C_1$-$C_6$-alkyl, —$(CH_2)_n$—$C_6$-$C_{12}$-aryl, —$(CH_2)_n$—$C_5$-$C_{18}$-heteroaryl, —$(CH_2)_n$—$C_3$-$C_{10}$-cycloalkyl, —$(CH_2)_n$—$C_3$-$C_{12}$-heterocycloalkyl, -phenylene-$(CH_2)_p$—$R^6$, —$(CH_2)_p$—$NR^5R^6$, —$(CH_2)_p$—$NR^4COR^5$, —$(CH_2)_p$—$NR^4CSR^5$, —$(CH_2)_p$—$NR^4S(O)R^5$, —$(CH_2)_p$—$NR^4S(O)_2R^5$, —$(CH_2)_p$—$NR^4CONR^5R^6$, —$(CH_2)_p$—$NR^4COOR^5$, —$(CH_2)_p$—$NR^4C(NH)NR^5R^6$, —$(CH_2)_p$—$NR^4CSNR^5R^6$, —$(CH_2)_p$—$NR^4S(O)NR^5R^6$, —$(CH_2)_p$—$NR^4S(O)_2NR^5R^6$, —$(CH_2)_p$—$COR^5$, —$(CH_2)_p$—$CSR^5$, —$(CH_2)_p$—$S(O)R^5$, —$(CH_2)_p$—$S(O)(NH)R^5$, —$(CH_2)_p$—$S(O)_2R^5$, —$(CH_2)_p$—$S(O)_2NR^5R^6$, —$(CH_2)_p$—$SO_2OR^5$, —$(CH_2)_p$—$CO_2R^5$, —$(CH_2)_p$—$CONR^5R^6$, —$(CH_2)_p$—$CSNR^5R^6$, —$OR^5$, —$CHR^5R^6$, —$(CH_2)_p$—$SR^5$, and —$CR^5(OH)$—$R^6$, wherein —$C_1$-$C_6$-alkyl, —$C_2$-$C_6$-alkenyl, —$C_2$-$C_6$-alkynyl, —$C_3$-$C_{10}$-cycloalkyl, —$C_3$-$C_{12}$-heterocycloalkyl, —$C_6$-$C_{12}$-aryl, —$C_5$-$C_{18}$-heteroaryl, and —$C_1$-$C_6$-alkoxy are each unsubstituted or are substituted one or more times independently of one another by hydroxy, halogen, nitro, cyano, —$NR^5R^6$, —$C(O)NR^5R^6$, —$S(O)_2NR^5R^6$, —$NR^5S(O)_2R^6$, —$NR^5C(O)R^6$, —$SR^5$, —$R^5$ or —$OR^5$, wherein the carbon framework of the —$C_3$-$C_{10}$-cycloalkyl and of the —$C_1$-$C_{10}$-alkyl optionally comprise one or more times independently of one another nitrogen, oxygen, sulphur atoms, —$NR^4$ or C=O groups, or one or more double bonds, or $R^1$ and $R^2$ optionally together form a bridge of 3-10 methylene units, wherein up to two methylene units are each optionally replaced by O, S or —$NR^4$;

$R^3$ and $R^4$ are selected independently of one another from hydrogen, —$C_1$-$C_{10}$-alkyl, —$C_2$-$C_6$-alkenyl, —$C_2$-$C_6$-alkynyl, —$C_3$-$C_{10}$-cycloalkyl, —$C_3$-$C_{12}$-heterocycloalkyl, and —$C_1$-$C_{10}$-alkanoyl, where —$C_1$-$C_{10}$-alkyl, —$C_2$-$C_6$-alkenyl, —$C_2$-$C_6$-alkynyl, —$C_3$-$C_{10}$-cycloalkyl, —$C_3$-$C_{12}$-heterocycloalkyl, and —$C_1$-$C_{10}$-alkanoyl are each unsubstituted or is substituted one or more times independently of one another by hydroxy, halogen, nitro, cyano, phenyl, —$NR^5R^6$, alkyl, —$SR^5$ or —$OR^5$, $R^5$ and $R^6$ are identical or different and are selected independently of one another from hydrogen, —$C_1$-$C_{10}$-alkyl, —$C_2$-$C_{10}$-alkenyl, —$C_2$-$C_{10}$-alkynyl, —$C_1$-$C_6$-alkoxy, —$C_3$-$C_{10}$-cycloalkyl, —$C_3$-$C_{12}$-heterocycloalkyl, —$C_6$-$C_{12}$-aryl, and —$C_5$-$C_{18}$-heteroaryl, wherein —$C_1$-$C_{10}$-alkyl, —$C_2$-$C_{10}$-alkenyl, —$C_2$-$C_{10}$-alkynyl, —$C_1$-$C_6$-alkoxy, —$C_3$-$C_{10}$-cycloalkyl, —$C_3$-$C_{12}$-heterocycloalkyl, —$C_6$-$C_{12}$-aryl, and —$C_5$-$C_{18}$-heteroaryl are each unsubstituted or are substituted one or more times independently of one another by hydroxy, halogen, cyano, nitro, —$OR^7$, —$NR^7R^8$, —$C(O)NR^7R^8$, —$C(O)OR^7$ or —$C_1$-$C_6$-alkyl, wherein —$C_1$-$C_6$-alkyl is unsubstituted or is substituted one or more times independently of one another by halogen, hydroxy, cyano, —$NR^7R^8$, —$OR^7$ or phenyl; or $R^5$ and $R^6$ optionally together form a bridge of 3-10 methylene units, where up to two methylene units are each optionally replaced by O, S or $NR^4$;

$R^7$, $R^8$ are identical or different and are selected independently of one another from t hydrogen, —$C_1$-$C_4$-alkyl, —$C_6$-$C_{12}$-aryl, and —$C_5$-$C_{18}$-heteroaryl, where alkyl, aryl, and heteroaryl are each unsubstituted or is substituted one or more times independently of one another by halogen or alkoxy, or $R^7$ and $R^8$ optionally together form a bridge of 3-10 methylene units, where up to two methylene units are each optionally replaced by O, S or —$NR^4$;

n=1, 2, 3, 4, 5, or 6;

p=0, 1, 2, 3, 4, 5, or 6; and or an N-oxide, stereoisomer, diastereomer, enantiomer, or physiologically tolerated salt thereof.

19. A compound according to claim 1, wherein

Y-Q is $NR^1R^2$;

$R^1$ is a hydrogen atom;

$R^2$ is selected from hydrogen, —$C_1$-$C_6$-alkyl, —$C_1$-$C_4$-hydroxyalkyl, —$C_2$-$C_6$-alkenyl, —$C_2$-$C_6$-alkynyl, —$C_3$-$C_{10}$-cycloalkyl, —$C_3$-$C_{12}$-heterocycloalkyl, —$C_6$-$C_{12}$-aryl, —$C_5$-$C_{18}$-heteroaryl, —$C_1$-$C_6$-alkoxy, —$C_1$-$C_6$-alkoxy-$C_1$-$C_6$-alkoxy, —$C_1$-$C_6$-alkoxy-$C_1$-$C_6$-alkyl, —$C_1$-$C_6$-alkoxy-$C_1$-$C_6$-alkoxy-$C_1$-$C_6$-alkyl, —$(CH_2)_p$—$C_6$-$C_{12}$-aryl, —$(CH_2)_n$—$C_5$-$C_{18}$-heteroaryl, —$(CH_2)_n$—$C_3$-$C_{10}$-cycloalkyl, —$(CH_2)_n$—$C_3$-$C_{12}$-heterocycloalkyl, -phenylene-$(CH_2)_p$—$R^6$, —$(CH_2)_p$—$NR^5R^6$, —$(CH_2)_p$—$NR^4COR^5$, —$(CH_2)_p$—$NR^4CSR^5$, —$(CH_2)_p$—$NR^4S(O)R^5$, —$(CH_2)_p$—$NR^4S(O)_2R^5$, —$(CH_2)_p$—$NR^4CONR^5R^6$, —$(CH_2)_p$—$NR^4COOR^5$, —$(CH_2)_p$—$NR^4C(NH)NR^5R^6$, —$(CH_2)_p$—$NR^4CSNR^5R^6$, —$(CH_2)_p$—$NR^4S(O)NR^5R^6$, —$(CH_2)_p$—$NR^4S(O)_2NR^5R^6$, —$(CH_2)_p$—$COR^5$, —$(CH_2)_p$—$CSR^5$, —$(CH_2)_p$—$S(O)R^5$, —$(CH_2)_p$—$S(O)(NH)R^5$, —$(CH_2)_p$—$S(O)_2R^5$, —$(CH_2)_p$—$S(O)_2NR^5R^6$, —$(CH_2)_p$—$SO_2OR^5$, —$(CH_2)_p$—$CO_2R^5$, —$(CH_2)_p$—$CONR^5R^6$, —$(CH_2)_p$—$CSNR^5R^6$, —$OR^5$, —$CHR^5R^6$, —$(CH_2)_p$—$SR^5$ and —$CR^5(OH)$—$R^6$, wherein —$C_1$-$C_6$-alkyl, —$C_2$-$C_6$-alkenyl, —$C_2$-$C_6$-alkynyl, —$C_3$-$C_{10}$-cycloalkyl, —$C_3$-$C_{12}$-heterocycloalkyl, —$C_6$-$C_{12}$-aryl, —$C_5$-$C_{18}$-heteroaryl, and —$C_1$-$C_6$-alkoxy are unsubstituted or are substituted one or more times independently of one another by hydroxy, halogen, nitro, cyano, —$NR^5R^6$, —$C(O)NR^5R^6$, —$S(O)_2NR^5R^6$, —$NR^5S(O)_2R^6$, —$NR^5C(O)R^6$, —$SR^5$, —$R^5$ or —$OR^5$, wherein the carbon framework of the —$C_3$-$C_{10}$-cycloalkyl and of the —$C_1$-$C_{10}$-alkyl optionally comprise one or more times independently of one another nitrogen, oxygen, sulphur atoms, —$NR^4$ or C=O groups, or one or more double bonds, or $R^1$ and $R^2$ optionally together form a bridge of 3-10 methylene units, where up to two methylene units are each optionally replaced by O, S or —$NR^4$;

$R^3$ and $R^4$ are selected independently of one another from hydrogen, —$C_1$-$C_{10}$-alkyl, —$C_2$-$C_6$-alkenyl, —$C_2$-$C_6$-alkynyl, —$C_3$-$C_{10}$-cycloalkyl, —$C_3$-$C_{12}$-heterocycloalkyl, and —$C_1$-$C_{10}$-alkanoyl, where —$C_1$-$C_{10}$- alkyl, —$C_2$-$C_6$-alkenyl, —$C_2$-$C_6$-alkynyl, —$C_3$-$C_{10}$-cycloalkyl, —$C_3$-$C_{12}$-heterocycloalkyl, and —$C_1$-$C_{10}$-alkanoyl are each unsubstituted or is substituted one or more times independently of one another by hydroxy, halogen, nitro, cyano, phenyl, —$NR^5R^6$, alkyl, —$SR^5$ or —$OR^5$, $R^5$ and $R^6$ are identical or different and are selected independently of one another from hydrogen, —$C_1$-$C_{10}$-alkyl, —$C_2$-$C_{10}$-alkenyl, —$C_2$-$C_{10}$-alkynyl, —$C_1$-$C_6$-alkoxy, —$C_3$-$C_{10}$-cycloalkyl, —$C_3$-$C_{12}$-heterocycloalkyl, —$C_6$-$C_{12}$-aryl, and —$C_5$-$C_{18}$-heteroaryl, wherein —$C_1$-$C_{10}$-alkyl, —$C_2$-$C_{10}$-alkenyl, —$C_2$-$C_{10}$-alkynyl, —$C_1$-$C_6$-alkoxy, —$C_3$-$C_{10}$-cycloalkyl, —$C_3$-$C_{12}$-heterocycloalkyl, —$C_6$-$C_{12}$-aryl, and —$C_5$-$C_{18}$-heteroaryl are each unsubstituted or are substituted one or more times independently of one another by hydroxy, halogen, cyano, nitro, —$OR^7$, —$NR^7R^8$, —$C(O)NR^7R^8$, —$C(O)OR^7$ or —$C_1$-$C_6$-alkyl, wherein —$C_1$-$C_6$-alkyl is unsubstituted or is substituted one or more times independently of one another by halogen, hydroxy, cyano, —$NR^7R^8$, —$OR^7$ or phenyl; or $R^5$ and $R^6$ optionally together form a bridge of 3-10 methylene units, where up to two methylene units are each optionally replaced by O, S or $NR^4$;

$R^7$, $R^8$ are identical or different and are selected independently of one another from hydrogen, —$C_1$-$C_4$-alkyl, —$C_6$-$C_{12}$-aryl, and —$C_5$-$C_{18}$-heteroaryl, wherein alkyl, aryl, and heteroaryl are each unsubstituted or is substituted one or more times independently of one another by halogen or alkoxy, or $R^7$ and $R^8$ optionally together form a bridge of 3-10 methylene units, where up to two methylene units are each optionally replaced by 0, S or —$NR^4$;

n=1, 2, 3, 4, 5, or 6;
p=0, 1, 2, 3, 4, 5, or 6; and
or an N-oxide, stereoisomer, diastereomer, enantiomer, or physiologically tolerated salt thereof.

20. A compound according to claim 1,
wherein
Y-Q is $NR^1R^2$;
$R^1$ is a hydrogen atom;
$R^2$ is selected from hydrogen, —$C_1$-$C_6$-alkyl, —$C_1$-$C_4$-hydroxyalkyl, —$C_2$-$C_6$-alkenyl, —$C_2$-$C_6$-alkynyl, —$C_3$-$C_{10}$-cycloalkyl, —$C_3$-$C_{12}$-heterocycloalkyl, —$C_6$-$C_{12}$-aryl, —$C_5$-$C_{18}$-heteroaryl, —$C_1$-$C_6$-alkoxy, —$C_1$-$C_6$-alkoxy-$C_1$-$C_6$-alkoxy, —$C_1$-$C_6$-alkoxy-$C_1$-$C_6$-alkyl, —$C_1$-$C_6$-alkoxy-$C_1$-$C_6$-alkoxy-$C_1$-$C_6$-alkyl, —$(CH_2)_n$—$C_6$-$C_{12}$-aryl, —$(CH_2)_n$—$C_5$-$C_{18}$-heteroaryl, —$(CH_2)_n$—$C_3$-$C_{10}$-cycloalkyl, —$(CH_2)_n$—$C_3$-$C_{12}$-heterocycloalkyl, -phenylene-$(CH_2)_p$—$R^6$, —$(CH_2)_p$—$NR^5R^6$, —$(CH_2)_p$—$NR^4COR^5$, —$(CH_2)_p$—$NR^4CSR^5$, —$(CH_2)_p$—$NR^4S(O)R^5$, —$(CH_2)_p$—$NR^4S(O)_2R^5$, —$(CH_2)_p$—$NR^4CONR^5R^6$, —$(CH_2)_p$—$NR^4COOR^5$, —$(CH_2)_p$—$NR^4C(NH)NR^5R^6$, —$(CH_2)_p$—$NR^4CSNR^5R^6$, —$(CH_2)_p$—$NR^4S(O)NR^5R^6$, —$(CH_2)_p$—$NR^4S(O)_2NR^5R^6$, —$(CH_2)_p$—$COR^5$, —$(CH_2)_p$—$CSR^5$, —$(CH_2)_p$—$S(O)R^5$, —$(CH_2)_p$—$S(O)(NH)R^5$, —$(CH_2)_p$—$S(O)_2R^5$, —$(CH_2)_p$—$S(O)_2NR^5R^6$, —$(CH_2)_p$—$SO_2OR^5$, —$(CH_2)_p$—$CO_2R^5$, —$(CH_2)_p$—$CONR^5R^6$, —$(CH_2)_p$—$CSNR^5R^6$, —$OR^5$, —$CHR^5R^6$, —$(CH_2)_p$—$SR^5$, and —$CR^5(OH)$—$R^6$, wherein —$C_1$-$C_6$-alkyl, —$C_2$-$C_6$-alkenyl, —$C_2$-$C_6$-alkynyl, —$C_3$-$C_{10}$-cycloalkyl, —$C_3$-$C_{12}$-heterocycloalkyl, —$C_6$-$C_{12}$-aryl, —$C_5$-$C_{18}$-heteroaryl, and —$C_1$-$C_6$-alkoxy are each unsubstituted or are substituted one or more times independently of one another by hydroxy, halogen, nitro, cyano, —$NR^5R^6$, —$C(O)NR^5R^6$, —$S(O)_2NR^5R^6$, —$NR^5S(O)_2R^6$, —$NR^5C(O)R^6$, —$SR^5$, —$R^5$ or —$OR^5$, wherein the carbon framework of the —$C_3$-$C_{10}$-cycloalkyl and of the —$C_1$-$C_{10}$-alkyl optionally comprise one or more times independently of one another nitrogen, oxygen, sulphur atoms, —$NR^4$ or C=O groups, or one or more double bonds, or $R^1$ and $R^2$ optionally together form a bridge of 3-10 methylene units, where up to two methylene units are each optionally replaced by 0, S or —$NR^4$;

$R^3$ is —$C_1$-$C_{10}$-alkyl;
$R^4$ is selected from hydrogen, —$C_1$-$C_{10}$-alkyl, —$C_2$-$C_6$-alkenyl, —$C_2$-$C_6$-alkynyl, —$C_3$-$C_{10}$-cycloalkyl, —$C_3$-$C_{12}$-heterocycloalkyl, and —$C_1$-$C_{10}$-alkanoyl, wherein —$C_1$-$C_{10}$-alkyl, —$C_2$-$C_6$-alkenyl, —$C_2$-$C_6$-alkynyl, —$C_3$-$C_{10}$-cycloalkyl, —$C_3$-$C_{12}$-heterocycloalkyl, and —$C_1$-$C_{10}$-alkanoyl is unsubstituted or is substituted one or more times independently of one another by hydroxy, halogen, nitro, cyano, phenyl, —$NR^5R^6$, alkyl, —$SR^5$ or —$OR^5$, $R^5$ and $R^6$ are identical or different and are selected independently of one another from hydrogen, —$C_1$-$C_{10}$-alkyl, —$C_2$-$C_{10}$-alkenyl, —$C_2$-$C_{10}$-alkynyl, —$C_1$-$C_6$-alkoxy, —$C_3$-$C_{10}$-cycloalkyl, —$C_3$-$C_{12}$-heterocycloalkyl, —$C_6$-$C_{12}$-aryl, and —$C_5$-$C_{18}$-heteroaryl, wherein —$C_1$-$C_{10}$-alkyl, —$C_2$-$C_{10}$-alkenyl, —$C_2$-$C_{10}$-alkynyl, —$C_1$-$C_6$-alkoxy, —$C_3$-$C_{10}$-cycloalkyl, —$C_3$-$C_{12}$-heterocycloalkyl, —$C_6$-$C_{12}$-aryl, and —$C_5$-$C_{18}$-heteroaryl are each unsubstituted or are substituted one or more times independently of one another by hydroxy, halogen, cyano, nitro, —$OR^7$, —$NR^7R^8$, —$C(O)NR^7R^8$, —$C(O)OR^7$ or —$C_1$-$C_6$-alkyl, wherein —$C_1$-$C_6$-alkyl is unsubstituted or is substituted one or more times independently of one another by halogen, hydroxy, cyano, —$NR^7R^8$, —$OR^7$ or phenyl; or $R^5$ and $R^6$ optionally together form a bridge of 3-10 methylene units, where up to two methylene units are each optionally replaced by O, S or $NR^4$;

$R^7$, $R^8$ are identical or different and are selected independently of one another from t hydrogen, —$C_1$-$C_4$-alkyl, —$C_6$-$C_{12}$-aryl, and —$C_5$-$C_{18}$-heteroaryl, wherein alkyl, aryl, and heteroaryl are each unsubstituted or is substituted one or more times independently of one another by halogen or alkoxy, or $R^7$ and $R^8$ optionally together form a bridge of 3-10 methylene units, where up to two methylene units are each optionally replaced by O, S or —$NR^4$;

n=1, 2, 3, 4, 5, or 6;
p=0, 1, 2, 3, 4, 5, or 6; and
or an N-oxide, stereoisomer, diastereomer, enantiomer, or physiologically tolerated salt thereof.

21. A compound according to claim 1, wherein said compound is selected from:
4-methyl-3-[[6-[[(R)-methyloxidophenyl-$\lambda^4$-sulphanylidene]amino]-4-quinolinyl]amino]phenol;
4-methyl-3-[[6-[[(S)-methyloxidophenyl-$\lambda^4$-sulphanylidene]amino]-4-quinolinyl]amino]phenol;
3-[[6-[[(R)-methyloxidophenyl-$\lambda^4$-sulphanylidene]amino]-4-quinolinyl]amino]phenol;
3-[[6-[[(S)-methyloxidophenyl-$\lambda^4$-sulphanylidene]amino]-4-quinolinyl]amino]phenol;
3-[[6-[(dimethyloxido-$\lambda^4$-sulphanylidene)amino]-4-quinolinyl]amino]-4-methyl-phenol;
3-methoxy-5-[[6-[[(R)-methyloxidophenyl-$\lambda^4$-sulphanylidene]amino]-4-quinolinyl]amino]phenol;
3-methoxy-5-[[6-[[(S)-methyloxidophenyl-$\lambda^4$-sulphanylidene]amino]-4-quinolinyl]amino]phenol; and
3-[[6-[(dimethyloxido-$\lambda^4$-sulphanylidene)amino]-4-quinolinyl]amino]-5-methoxyphenol.

* * * * *

UNITED STATES PATENT AND TRADEMARK OFFICE
CERTIFICATE OF CORRECTION

PATENT NO. : 8,003,787 B2
APPLICATION NO. : 12/126437
DATED : August 23, 2011
INVENTOR(S) : Knut Eis et al.

Page 1 of 1

It is certified that error appears in the above-identified patent and that said Letters Patent is hereby corrected as shown below:

Column 68, Line 34 reads: "-$(CH_2)_p$-$C_6$-$C_{12}$-aryl, -$(CH_2)_n$-$C_5$-$C_{18}$-het-" should read --"-$(CH_2)_n$-$C_6$-$C_{12}$-aryl, -$(CH_2)_n$-$C_5$-$C_{18}$-het-"--

Signed and Sealed this
Third Day of January, 2012

David J. Kappos
*Director of the United States Patent and Trademark Office*